(12) United States Patent
Low et al.

(10) Patent No.: US 12,319,721 B2
(45) Date of Patent: Jun. 3, 2025

(54) TARGETING ANABOLIC DRUGS FOR ACCELERATED FRACTURE REPAIR

(71) Applicant: Purdue Research Foundation, West Lafayette, IN (US)

(72) Inventors: Philip Stewart Low, West Lafayette, IN (US); Stewart A. Low, West Lafayette, IN (US); Jeffery Jay Howard Nielsen, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 18/074,275

(22) Filed: Dec. 2, 2022

(65) Prior Publication Data
US 2023/0279068 A1  Sep. 7, 2023

Related U.S. Application Data

(63) Continuation of application No. 17/058,884, filed on Nov. 25, 2020, now abandoned, which is a continuation of application No. PCT/US2019/034759, filed on May 30, 2019.

(60) Provisional application No. 62/678,016, filed on May 30, 2018.

(51) Int. Cl.
| | | |
|---|---|---|
| C07K 14/00 | (2006.01) |
| A61K 38/18 | (2006.01) |
| A61K 47/60 | (2017.01) |
| A61K 47/64 | (2017.01) |
| C07K 14/47 | (2006.01) |
| C07K 14/49 | (2006.01) |
| C07K 14/50 | (2006.01) |
| C07K 14/51 | (2006.01) |
| C07K 14/575 | (2006.01) |
| C07K 14/65 | (2006.01) |
| C07K 14/78 | (2006.01) |
| C07K 14/79 | (2006.01) |
| C12N 9/12 | (2006.01) |
| C12N 9/54 | (2006.01) |
| C12N 9/74 | (2006.01) |
| A61K 38/00 | (2006.01) |

(52) U.S. Cl.
CPC .......... *C07K 14/51* (2013.01); *A61K 38/1875* (2013.01); *A61K 47/60* (2017.08); *A61K 47/6435* (2017.08); *A61K 47/645* (2017.08); *C07K 14/47* (2013.01); *C07K 14/4721* (2013.01); *C07K 14/49* (2013.01); *C07K 14/50* (2013.01); *C07K 14/575* (2013.01); *C07K 14/65* (2013.01); *C07K 14/78* (2013.01); *C07K 14/79* (2013.01); *C12N 9/12* (2013.01); *C12N 9/54* (2013.01); *C12N 9/6429* (2013.01); *A61K 38/00* (2013.01); *C07K 2319/02* (2013.01)

(58) Field of Classification Search
CPC .... A61K 38/125; A61K 47/645; A61K 47/65; A61K 38/1875; A61K 47/6435; C07K 14/50; C07K 14/501; C07K 14/51
See application file for complete search history.

(56) References Cited

U.S. PATENT DOCUMENTS

| | | |
|---|---|---|
| 7,803,770 B2 | 9/2010 | Dey et al. |
| 7,981,862 B2 | 7/2011 | Zamora et al. |
| 8,748,382 B2 | 6/2014 | Dey et al. |
| 10,960,054 B2 | 3/2021 | Low et al. |
| 2002/0019351 A1 | 2/2002 | Ke et al. |
| 2004/0014658 A1 | 1/2004 | Bogin et al. |
| 2006/0199765 A1 | 9/2006 | Gardella et al. |
| 2008/0181880 A1 | 7/2008 | Vignery et al. |
| 2009/0253630 A1 | 10/2009 | Brown-Augsburger et al. |
| 2010/0048462 A1 | 2/2010 | Ryge et al. |
| 2011/0046059 A1 | 2/2011 | Merutka et al. |
| 2011/0142764 A1 | 6/2011 | Satchi-Fainaro et al. |
| 2011/0269687 A1 | 11/2011 | Beyer, Jr. et al. |
| 2012/0270787 A1 | 10/2012 | Doschak et al. |
| 2013/0029901 A1 | 1/2013 | Pierce, Jr. et al. |
| 2013/0157955 A1 | 6/2013 | Dey et al. |
| 2014/0378382 A1 | 12/2014 | Gellman et al. |
| 2015/0246957 A1 | 9/2015 | Doschak et al. |
| 2015/0307550 A1 | 10/2015 | Nestor |
| 2016/0052968 A1 | 2/2016 | Crine et al. |
| 2017/0065682 A1 | 3/2017 | Hattersley |
| 2017/0101683 A1 | 4/2017 | Gomis et al. |
| 2018/0208650 A1 | 7/2018 | Qiu et al. |
| 2018/0214459 A1 | 8/2018 | Downing et al. |
| 2020/0316174 A1 | 10/2020 | Low et al. |
| 2020/0317745 A1 | 10/2020 | Low et al. |
| 2021/0206820 A1 | 7/2021 | Low et al. |

(Continued)

FOREIGN PATENT DOCUMENTS

| | | |
|---|---|---|
| CN | 102824647 A | 12/2012 |
| CN | 106039316 A | 10/2016 |

(Continued)

OTHER PUBLICATIONS

Agrawal et al. Recruitment of Progenitor Cells by an Extracellular Matrix Cryptic Peptide in a Mouse Model of Digit Amputation. Tissue Engineering 17(19-20):2435-2443 (2011).
Altschul et al. Basic Local Alignment Search Tool. J. Mol. Biol. 215:403-410 (1990).
Amso et al. Short Anabolic Peptides for Bone Growth. Med. Res. Rev. 36(4):579-640 (2016).
Aoki et al. Peptide-based delivery to bone. Advanced Drug Delivery Reviews 64(12):1220-1238 (2012).

(Continued)

*Primary Examiner* — Jeanette M Lieb
(74) *Attorney, Agent, or Firm* — Reichel Stohry Dean LLP; Natalie J. Dean

(57) ABSTRACT

The targeted delivery of growth factors, vasoactive peptides and other representative anabolic peptide drugs from different signaling cascades to bone fracture for accelerated healing is disclosed herein.

16 Claims, 79 Drawing Sheets

Specification includes a Sequence Listing.

(56) References Cited

U.S. PATENT DOCUMENTS

| | | |
|---|---|---|
| 2021/0213135 A1 | 7/2021 | Low et al. |
| 2021/0214408 A1 | 7/2021 | Low et al. |
| 2021/0283227 A1 | 9/2021 | Low et al. |

FOREIGN PATENT DOCUMENTS

| | | |
|---|---|---|
| JP | 2000327583 A | 11/2000 |
| JP | 2007533669 A | 11/2007 |
| JP | 2008501307 A | 1/2008 |
| JP | 2010505835 A | 2/2010 |
| JP | 2010523671 A | 7/2010 |
| JP | 2010526543 A | 8/2010 |
| JP | 2014517825 A | 7/2014 |
| RU | 2422172 C2 | 6/2011 |
| WO | WO-9220371 A1 | 11/1992 |
| WO | WO-2005095443 A1 | 10/2005 |
| WO | WO-2005103263 A1 | 11/2005 |
| WO | WO-2005121344 A1 | 12/2005 |
| WO | WO-2008063279 A2 | 5/2008 |
| WO | WO-2008124166 A2 | 10/2008 |
| WO | WO-2008138131 A1 | 11/2008 |
| WO | 2010015938 A2 | 2/2010 |
| WO | WO-2012111852 A1 | 8/2012 |
| WO | WO-2012145665 A2 | 10/2012 |
| WO | WO-2015113012 A1 | 7/2015 |
| WO | WO-2016196400 A1 | 12/2016 |
| WO | WO-2017160855 A1 | 9/2017 |
| WO | WO-2018102616 A1 | 6/2018 |
| WO | WO-2019232280 A1 | 12/2019 |
| WO | WO-2019232283 A1 | 12/2019 |
| WO | WO-2019232285 A1 | 12/2019 |
| WO | WO-2022093373 A1 | 5/2022 |
| WO | WO-2022093374 A1 | 5/2022 |

OTHER PUBLICATIONS

Arrighi et al., Bone healing induced by local delivery of an engineered parathyroid hormone prodrug. Biomaterials 30(9):1763-1771 (2009).
Berge et al. Pharmaceutical Salts. Journal of Pharmaceutical Sciences 66(1):1-19 (Jan. 1977).
Bhattacharya et al. Impact of genetic variation on three dimensional structure and function of proteins. PLoS One 12(3):e0171355 (2017).
Culpepper et al., Enhancement of Peptide Coupling Hydroxyapatite and Implant Osseointegration through 3ollagen Mimetic Peptide Modified with a Polyglutamate Domain. Biomaterials 31:9586-9594 (2010).
Culpepper et al., Polyglutamate directed coupling of bioactive peptides for the delivery of osteoinductive signals on allograft bone. Biomaterials 34(5):1506-1513 (2012).
Di Stasi et al. VEGFR Recognition Interface of a Proangiogenic VEGF-Mimetic Peptide Determined In Vitro and in the Presence of Endothelial Cells by NMR Spectroscopy. Chem. A Eur. J. 24:11461-6 (2018).
Fromigue et al. Peptide-based activation of alpha5 integrin for promoting osteogenesis. J Cell Biochem 113(9):3029-3038 (2012).
Gomar et al. P-15 small peptide bone graft substitute in the treatment of non-unions and delayed union. A pilot clinical trial. Int Orthop 31(1):93-99 (2006).
Hattori et al. Sequence specificity of the PHSRN peptide from fibronectin on corneal epithelial migration. Biochem Biophys Res Commun 379(2):346-50 (2009).
Haynes et al. Occurrence of pharmaceutically acceptable anions and cations in the Cambridge Structural Database. J Pharm Sci 94(10):2111-2120 (2005).
Hediger. Glutamate transporters in kidney and brain. Am. J. Physiol. 277:F487-F492 (1999).
Jiang et al., Poly aspartic acid peptide-linked PLGA based nanoscale particles: Potential for bone-targeting drug delivery application. International Journal of Pharmaceutics, 475:547-557 (Sep. 4, 2014).
Jung et al. Co-assembling peptides as defined matrices for endothelial cells. Biomaterials 30(12):2400-2410 (2009).
Kanai et al. Primary structure and functional characterization of a high-affinity glutamate transporter. Nature 360:467-471 (1992).
Kanai et al. The glutamate and neutral amino acid transporter family: physiological and pharmacological implications. Eur. J. Pharmacol. 479:237-247 (2003).
Kang et al. The effect of the DLTIDDSYWYRI motif of the human laminin a2 chain on implant osseointegration. Biomaterials 34(16):4027-37 (2013).
Leamon et al., Synthesis and biological evaluation of EC20: A new folate-derived, 99mTc-based radiopharmaceutical. Bioconjug. Chem. 13:1200-1210 (2002).
Low et al., Targeting polymer therapeutics to bone. Advanced Drug Delivery Reviews (64):1189-1204 (2012).
Martin. Parathyroid hormone-related protein, its regulation of cartilage and bone development, and role in treating bone diseases. Physiol. Rev. 96(3):831-71 (2016).
Morita et al. Enhanced initial bone regeneration with inorganic polyphosphate-adsorbed hydroxyapatite. Acta Biomater 6(7):2808-2815 (2010).
Nielsen et al. Analysis of the bone fracture targeting properties of osteotropic ligands. J Control Release 329:570-584 (2021).
Ong et al., Off-label use of bone morphogenetic proteins in the United States using administrative data. Spine 35:1794-1800 (2010).
PCT/US2017/064081 International Search Report and Written Opinion dated Apr. 12, 2018.
PCT/US2019/034759 International Search Report and Written Opinion dated Aug. 9, 2019.
PCT/US2019/034764 International Search Report and Written Opinion dated Aug. 22, 2019.
PCT/US2019/034767 International Search Report and Written Opinion dated Aug. 30, 2019.
PCT/US2021/047824 International Search Report and Written Opinion dated Feb. 4, 2022.
PCT/US2021/047824 Invitation to Pay Additional Fees dated Nov. 18, 2021.
Santulli et al. In vivo properties of the proangiogenic peptide QK. J. Transl. Med. 7:41 (2009).
Savoie et al., Studies on mono- and diiodohistidine. I. The identification of iodohistidines from thyroidal iodoproteins and their peripheral metabolism in the normal man and rat. J. Clin. Invest. 52:106-115 (1973).
Sawyer et al. The effect of the addition of a polyglutamate motif to RGD on peptide tethering to hydroxyapatite and the promotion of mesenchymal stem cell adhesion. Biomaterials 26(34):7046-7056 (2005).
Sekido et al., Novel drug delivery system to bone using acidic oligopeptide: pharmacokinetic characteristics and pharmacological potential. J Drug Target 9(2):111-1121 (2001).
Soltero et al., Chapter 10: Oral protein and peptide drug delivery. Drug Deliver: Principles and Applications. pp. 189-200 (2005) (citation in spec was incorrect).
Srouji et al. Lentiviral-Mediated Integrin [alpha]5 Expression in Human Adult Mesenchymal Stromal Cells Promotes Bone Repair in Mouse Cranial and Long-Bone Defects. Human Gene Therapy 23(2):167-172 (2012).
Tokuriki et al. Stability effects of mutations and protein evolvability. Curr. Opin. Struc. Biol. 19:596-604 (2009).
U.S. Appl. No. 16/464,164 Office Action dated Oct. 26, 2021.
U.S. Appl. No. 16/464,164 Restriction Requirement dated May 3, 2021.
U.S. Appl. No. 16/836,366 Office Action dated Jul. 15, 2020.
U.S. Appl. No. 17/058,884 Office Action dated Aug. 4, 2022.
U.S. Appl. No. 17/058,884 Office Action dated Mar. 8, 2022.
Wang et al. Synthesis and Evaluation of Water-Soluble Polymeric Bone-Targeted Drug Delivery Systems. Bioconjugate Chemistry 14(5):853-859 (2003).
Wu et al. Effect of IKVAV peptide nanofiber on proliferation, adhesion and differentiation into neurocytes of bone marrow stromal cells, J. Huazhong Univ. Sci. Technol. [Med Sci.] 30(2):178-182 (2010).

(56) References Cited

OTHER PUBLICATIONS

Yeo et al. Adhesion and spreading of osteoblast-like cells on surfaces coated with laminin-derived bioactive core peptides. Data Br. Elsevier 5:411-5 (2015).

Yokogawa et al., Selective delivery of estradiol to bone by aspartic acid oligopeptide and its effects on ovariectomized mice. Endocrinology 142:1228-1233 (2001).

Gandavarapu, et al., "Osteogenic Differentiation of Human Mesenchymal Stem Cells on α5 Integrin Binding Peptide Hydrogels is Dependent on Substrate Elasticity." Biomaterials Science, vol. 2(3), pp. 352-361 (Mar. 2014).

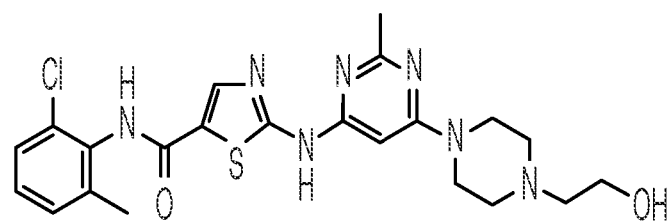
Dasatinib
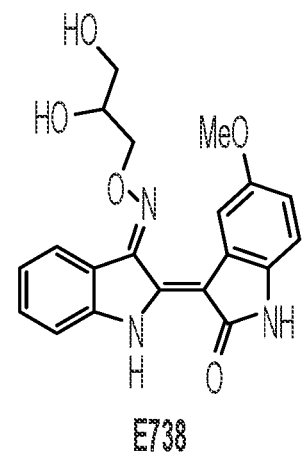
E738
FIG. 3

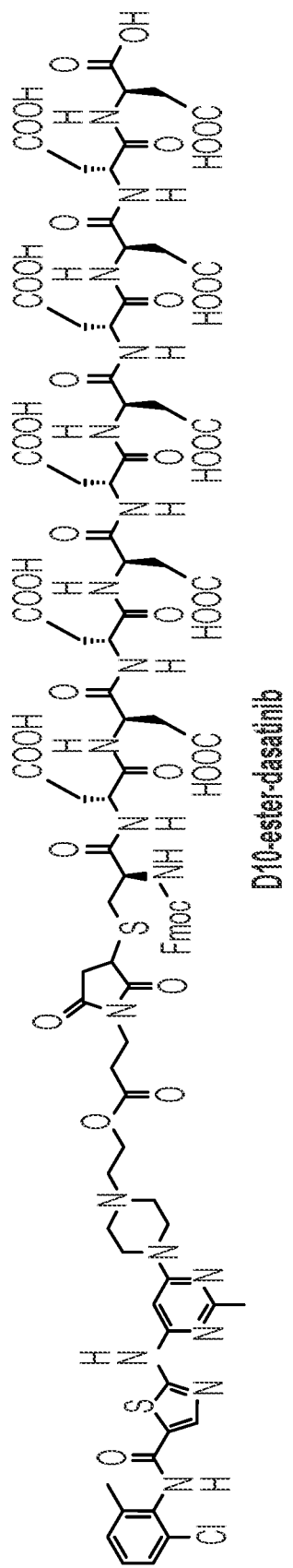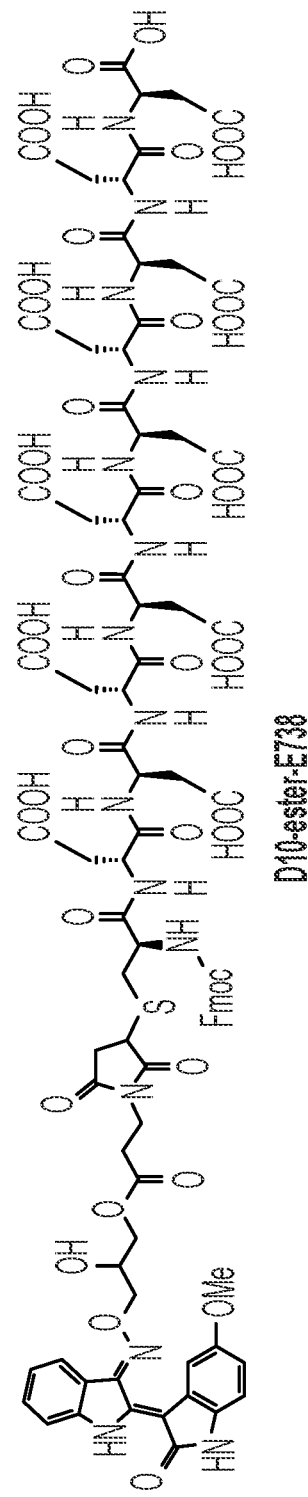
FIG. 4

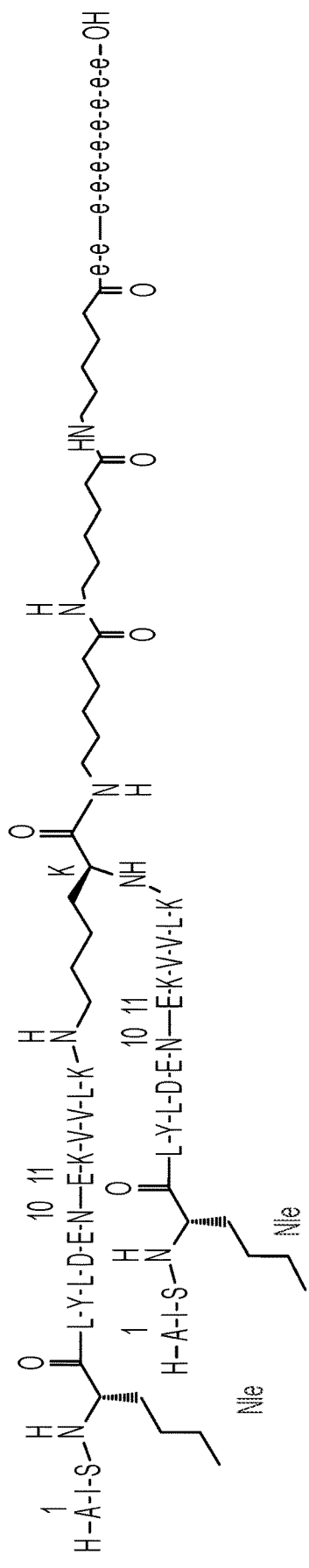

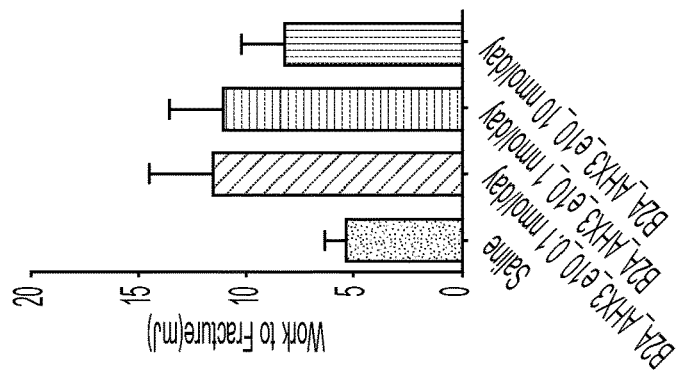
FIG. 39
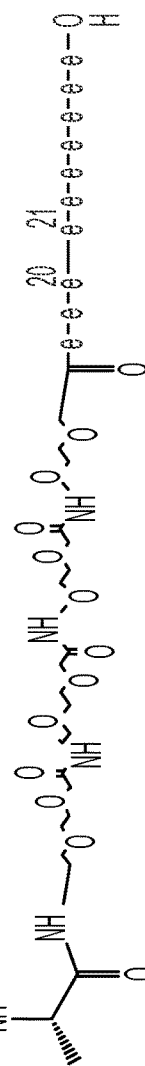
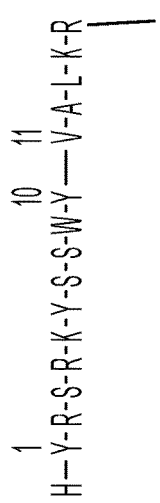
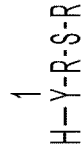
FIG. 40

TARGETING ANABOLIC DRUGS FOR ACCELERATED FRACTURE REPAIR

CROSS-REFERENCE TO RELATED APPLICATIONS

This application is a continuation application of U.S. patent application Ser. No. 17/058,884, filed Nov. 25, 2020, which is a 35 U.S.C. § 371 national stage application of International Application No. PCT/US2019/034759, filed May 30, 2019, which claims priority to U.S. Provisional Patent Application No. 62/678,016, filed on May 30, 2018, which are incorporated herein by reference in their entireties.

SEQUENCE LISTING

The instant application contains a Sequence Listing which has been submitted electronically in computer readable form in a Sequence Listing XML file (file entitled "68304-10SequenceListing_10JAN2025"; file size=53,686 bytes; date created Jan. 10, 2025) which is hereby incorporated by reference in its entirety. The information recorded in computer readable form is identical to the written Sequence Listing provided herein, pursuant to 37 C.F.R. § 1.821(f).

FIELD OF THE INVENTION

Aspects of the present disclosure relate to the materials and methods for treating bone fractures and bone defects.

BACKGROUND

Src tyrosine kinase plays a crucial role in bone metabolism: despite its ubiquitous expression profile, the only apparent phenotypical abnormality in a Sarcoma-knockout (Src-KO) mouse strain was osteopetrosis. Although Src inhibitors inhibit both the formation and activity of osteoblasts (OBs) in vitro, the number of osteoclasts (OCs) derived from Src-KO mice were actually elevated in Src-KO mice, measuring more than twice that in wild-type (WT) mice. Also, a marked increase in both osteoblast number and activity was observed in vivo in Src-KO mice. These results confirm that the osteopetrosis phenotype of Src-KO mice was not a result of reduced osteoclast formation, but rather of boosted osteoblast activity as well as reduced osteoclast function. Moreover, osteoblasts derived from Src-KO mice demonstrated unremarkable morphological features compared to those harvested from WT mice, and were able to fully regulate normal osteoclast differentiation via the receptor activator of nuclear factor kappa-B ligand/receptor activator of nuclear factor kappa-B/osteoprotegerin (RANKL/RANK/OPG) pathway. Thus, this bone-resorption defect should be easily alleviated by restoring normal Src functionality in osteoclasts, reducing potential risks on the musculoskeletal system involved in long-term use of Src inhibitors for fracture healing.

Broadly, peptide anabolic drugs include different categories of protein or the fragments thereof. They are represented by bone morphogenetic protein pathway signaling peptides including P4, bone forming peptide (BFP) and peptide from Bone morphogenetic protein 9 (pBMP9); insulin-like growth factor (IGF) derived peptides including mechanogrowth factor (MGF) and Preptin; bone stimulatory neuropeptides including Substance P and vasoactive intestinal peptide (VIP); and peptides enhancing vascular functions, including C-type Natriuretic peptide (CNP), thrombin fragment or targeted prothrombin peptide (TP508) and VIP. Each of these peptides may have its own unique mechanism working to regulate bone growth, as will be outlined in the detailed description.

Current clinical treatment of fractures generally does not include the use of site-specific anabolic drugs. In fact, the only drugs approved for clinical use on such fractures are bone morphogenic protein (BMP)-2 (approved for use only in tibial trauma) and BMP-7 (discontinued), which are applied locally and generally used in the treatment of open long bone fractures and spinal fusions. The need for broader application of anabolic drugs to treat bone maladies such as osteoporotic fractures with efficacy is evident.

Therefore, it is desirable to have a fracture treatment drug that is administered systemically yet targets the fracture site with evident efficacy.

SUMMARY

A first aspect of the present disclosure includes at least one compound of the formula X-Y-Z, or a pharmaceutically acceptable salt thereof, or a metabolite thereof, wherein X is at least one agent that improves bone density, mechanical strength, bone deposition, or quality; Z is at least one bone-targeting molecule; and Y is a linker that joins and/or links X and Z. In some aspects, X is at least one agent that enhances the activity or one agent that improves bone density, mechanical strength, bone deposition or otherwise promotes bone healing and/or growth. Consistent with some of these aspects, Z is at least one negatively charged oligopeptide or an equivalent thereof that binds to hydroxyapatite and/or raw bone.

The second aspect includes the compound according to the first aspect, wherein when X is a polypeptide, any polypeptide having at least about 80%, 81%, 82%, 83%, 84%, 85%, 86%, 87%, 88%, 89%, 90%, 91%, 92%, 93%, 94%, 95%, 96%, 97%, 98%, 99%, and/or 100% identity to X can be used to practice the invention.

In some aspects, Y is at least one polypeptide comprising at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence identity to amino acid residues 35-40, 35-41, 35-42, 35-43, 35-44, 35-45, 35-46, 35-47, 35-48, 35-49, 35-50, 35-51, 35-52, 35-55, 35-84, 41-44, 41-45, 41-46, 41-47, 41-48, 41-49, 41-50, and/or 41-84 of a full length parathyroid hormone related peptide or parathyroid hormone, and/or at least one Cathepsin K sensitive polypeptide.

In some aspects, Z is at least one polypeptide comprising about 4 or more, from about 4 to about 100, from about 4 to about 50, from about 4 to about 20, from about 4 to about 15, from about 4 to about 10 acidic amino acid residues, polyphosphate, 2-aminohexanedioic (aminoadipic) acid or derivatives thereof, and/or alendronate or derivatives thereof. In some aspects, Z is at least one polypeptide comprising about 4, 5, 6, 7, 8, 9, 10, 11, 12, 13, 14, 15, 16, 17, 18, 19, 20, 21, 22, 23, 24, 25, 26, 27, 28, 29, and/or 30 acidic amino acid residues, polyphosphate, 2-aminohexanedioic acid or derivatives thereof, and/or alendronate or derivatives thereof. In some aspects, Z is at least one negatively charged oligopeptide or an equivalent thereof that binds to hydroxyapatite and/or raw bone.

The targeted delivery strategy recited in some aspects of the invention enable the delivery of Src inhibitors specifically to bone fracture surfaces thereby facilitating fracture healing. This in vivo efficacy is shown by the acceleration of fracture healing observed using the Src inhibitors Dasatinib and E738.

In addition to Src inhibitors, a group of peptides targeted specifically to the fracture surfaces also demonstrates an enhanced ability to facilitate fracture healing. These peptides include osteopontin derived fragments such as osteopontin-derived peptide (ODP), collagen binding motif (CBM); BMP fragments such as P4, BFP, pBMP7; IGF fragments such as MGF and Preptin; neuropeptides such as Substance P and VIP; Vasoconstrictive fragments such as CNP, TP508 and VIP; and other anabolic drugs such as osteogenic growth peptide (OGP).

The in vivo efficacy of these peptides for accelerated fracture healing are demonstrated herein. All peptide conjugates are produced by solid phase synthesis.

Some aspects of this disclosure include compounds comprising: a compound of the formula X-Y-Z, wherein X is at least one agent that modulates bone growth, such as activity of Src tyrosine kinase; Z is at least one bone-targeting molecule; and Y is a linker that joins and/or links X and Z; or a pharmaceutically acceptable salt thereof, or a metabolite thereof. In some aspects, Z is at least one polypeptide comprising 6, 7, 8, 9, 10, 11, 12, 13, 14, 15, 16, 17, 18, 19 and/or 20 acidic amino acid residues. In some aspects, X is selected from the group consisting of Dasatinib and E738. In some aspects, Y is a releasable linker selected from disulfide; ester; or protease specific amide bond. In some aspects, Y is a nonreleasable bond selected from carbon-carbon bond; or amide bond.

In some aspects, this disclosure includes a compound of the formula X-Y-Z, wherein X is at least one peptide or a fragment thereof that modulates activity of bone and cartilage formation; Z is at least one bone-targeting molecule; and Y is a linker that joins and/or links X and Z; or a pharmaceutically acceptable salt thereof, or a metabolite thereof. In some aspects, Y is a releasable linker selected from disulfide; ester; or protease specific amide bond. In some aspects, Y is a nonreleasable bond selected from carbon-carbon bond; or amide bond. In some aspects, Y is a peptide belonging to the natural sequence of Z. In some aspects, Y is a polyethylene glycol (PEG) linker. In some aspects Y is a PEG linker comprised of 2-8 oxyethylene units. In some aspects, Z comprises at least 10 aspartic or glutamic acids conjugated to X. In some aspects, Z comprises at least 20 aspartic or glutamic acids conjugated to X. In some aspects, the compound may be produced by solid phase synthesis.

In some aspects, X is a bone anabolic peptide derived from BMP. In some aspects, X is a bone anabolic peptide derived from IGF. In some aspects, X is a bone anabolic peptide derived from a neuropeptide. In some aspects, X is a bone anabolic peptide that improves vascular function and/or vascularization. In some aspects, X is osteogenic growth peptide (OGP). In some aspects, the peptide is BFP, P4, or pBMP9. In some aspects, the peptide is MGF or Preptin. In some aspects, the peptide is Substance P or VIP. In some aspects, the peptide is TP508, VIP, or CNP. Unless indicated otherwise, the invention may be practiced by combining any X with any Z and optionally any suitable linking group Y.

1. A compound comprising:
a compound of the formula X-Y-Z, wherein
X is at least one agent that modulates activity selected from the group consisting of: Bone Morphogenic Protein(s) BMP, Insulin Like Growth Factors (IGF), fibroblast growth factors, peptide, hormones, hormone releasing agents, lactoferrin, Ghrelin, c-Jun N-terminal kinase 3 agonists (JNK3 agonists), vasoactive peptide(s), any growth factor, and any active portion of any growth factor;
Z is at least one bone-targeting molecule; and
Y is an optional linker that joins and/or links X and Z;
or a pharmaceutically acceptable salt thereof, or a metabolite thereof.

2. The compound according to claim 1, wherein Z is at least one polypeptide comprising 6, 7, 8, 9, 10, 11, 12, 13, 14, 15, 16, 17, 18, 19 and/or 20 acidic amino acid residues.

3. The compound according to claims 1-2 wherein Z includes multiple aspartates and/or multiple glutamates.

4. The compound according to claim 3, wherein Z is comprised of at least one polypeptide selected from the group consisting of: at least 5 aspartic acids (SEQ ID NO: 38), at least 5 glutamic acids (SEQ ID NO: 39), at least 10 aspartic acids (SEQ ID NO: 30), at least 10 glutamic acids (SEQ ID NO: 31), at least 20 aspartic acids (SEQ ID NO: 40), at least 20 glutamic acids (SEQ ID NO: 41).

5. The compounds according to claims 1-4, wherein Z is selected from the group consisting of: a polypeptide comprising 10 aspartic acid residues (SEQ ID NO. 30) and a polypeptide comprising 10 glutamic acid residues (SEQ ID NO. 31).

6. The compound according to claims 1-4, wherein Z is selected from the group consisting of: 4 or more acidic amino acid residues, polyphosphate, aminohexanedioic acid or derivatives thereof, and/or alendronate or derivatives thereof.

7. The compound according to claims 1-6, wherein Y is selected from the group consisting of: releasable linkers and non-releasable linkers.

8. The compound according to claim 7, wherein the releasable linker includes at least of the following groups: a disulphide, an ester, or a Protease specific amide bond.

9. The compound according to claim 7, the non-releasable linker includes at least one of the following groups: a carbon-carbon bond, or an amide.

10. The compound according to claims 1-6, wherein Y is polyethylene glycol (PEG).

11. The compound according to claim 10, wherein the PEG linker is comprised of 2-8 oxyethylene units.

12. The compound according to claims 1-6, wherein Y is a peptide belonging to the natural sequence of Z.

13. The compound according to claims 1-9, wherein the BMP is at least one compound selected from the group consisting of: P4 (BMP2), BFP (BMP7), pBMP9 (BMP9), and B2A (BMP2/TGF beta).

14. The compound according to claims 1-9, wherein the Insulin Like Growth Factor is at least one compound selected from the group consisting of: Prep-tin (IGF-II), and Mechano Growth Factor (MGF) (IGF-1).

15. The compound according to claims 1-9, wherein the Fibroblast Growth Factor is at least one compound selected from the group consisting of: Fibroblast Growth Factor 2 (F119) and F2A.

16. The compound according to claims 1-9, wherein the Osteogenic peptide is histone h4.

17. The compound according to claims 1-9, wherein X is selected from the group consisting of: parathyroid hormone-related protein (PTHrP) [107-139], and Osteogenic peptide.

18. The compound according to claims 1-9, wherein the JNK3 agonist is JNK3 or Annexin 1.

19. The compound according to claims 1-9, wherein the Vasoactive peptide is at least one compound selected from the group consisting of: C-Type Natriuretic peptide (CNP), Thrombin peptide (TP508), VEGF mimetic (QK) and platelet derived growth factor 2A (P2A).

20. Use of a compound according to any of claims 1-19, for the manufacture of a medicament for therapeutic application.

21. A method of treating a patient, comprising the step of administering at least one dose of a compound according to claims 1-9.

These and other features, aspects and advantages of the present disclosure will become better understood with reference to the following figures, associated descriptions and claims.

BRIEF DESCRIPTION OF THE DRAWINGS

FIG. 3 depicts structures for Dasatinib and E738.

FIG. 4 depicts structures for targeted conjugates of Dasatinib and E738 comprising D10 (SEQ ID NO: 30).

FIG. 29 depicts the structure for Preptin D10 (SEQ ID NO: 3).

FIG. 31 depicts the structure for VIP D10 (SEQ ID NO: 17).

FIG. 33 depicts the structure for CBM D10 (SEQ ID NO: 9).

FIG. 34 depicts the structure for ODP D10 (SEQ ID NO: 13).

FIG. 35 depicts the structure of B2A_AHX3_e10 (SEQ ID NO: 19) comprising two amino acid branches of SEQ ID NO: 44 conjugated to e10 (SEQ ID NO: 45).

FIG. 39. Work to Fracture (mJ) measured after treatment with saline, or 0.1 nmol/day, 1 nmol/day or 10 nmol/day of B2A_AHX_e10.

FIG. 40. Structure of F2A_mp4_e10 (SEQ ID NOS: 28, 32, and 45).

BRIEF DESCRIPTION OF THE SEQUENCES

Figure 1:
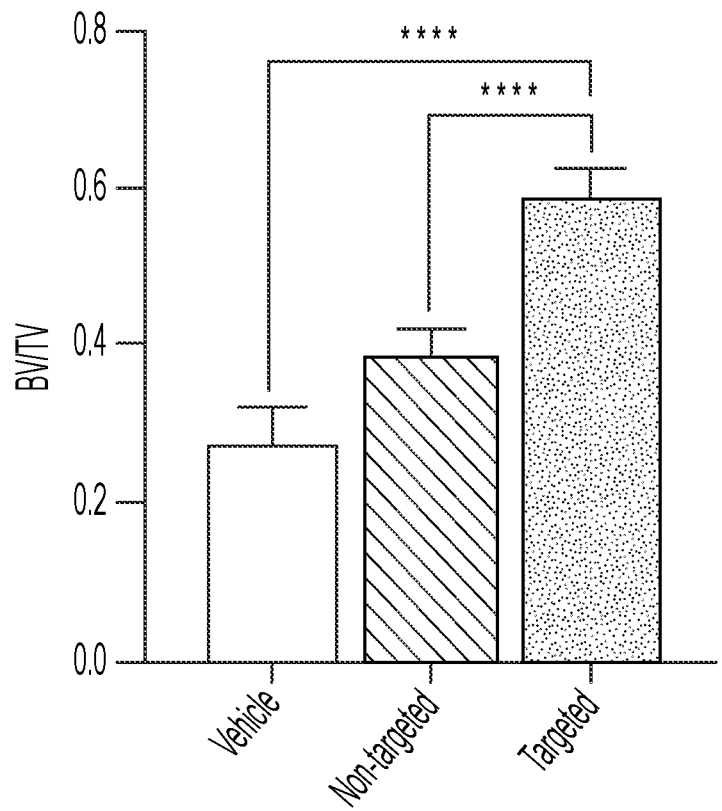
FIG. 1 depicts the bone volume divided by total volume of the 100 thickest micro computed tomography (CT) slices of the fracture callus bone density ("BV/TV") using a Dasatinib and targeted Dasatinib conjugate (both 10 µmol/kg). Both were subcutaneously dosed daily to fracture-bearing Notre Dame breed (ND4) of Swiss Webster mice. Bone density of the fracture callus from the targeted Dasatinib group is twice as dense as the saline group, and 50% denser than the free Dasatinib group.

SEQ ID NO: 1: forming peptide conjugated with 10 aspartate acids (BFP D10).

SEQ ID NO: 2: osteogenic growth peptide conjugated with 10 aspartate acids (OGP D10).

SEQ ID NO: 3: Preptin conjugated with 10 aspartate acids (Preptin D10).

SEQ ID NO: 4: substance P with 4 mini PEG linker and conjugated with 10 aspartate acids (substance P 4 mini PEG D10).

SEQ ID NO: 5: Ghrelin D10 with Ser-3 replaced with diaminopropinoic acid modified with an octanoyl group sidechain.

SEQ ID NO: 6: BMP9 D10.

SEQ ID NO: 7: C-type Natriuretic peptide (CNP) conjugated with 10 aspartate acids (CNP 10).

SEQ ID NO: 8: Vasoactive intestinal peptide conjugated with D10.

SEQ ID NO: 9: collagen binding motif conjugated with 10 aspartate acids (CBM D10).

SEQ ID NO: 10: P4 conjugated with 10 aspartate acids (P4 D10).

SEQ ID NO: 10: P4 conjugated with 10 aspartate acids (P4 D10).

SEQ ID NO: 11: Mechano-growth factor conjugated with 10 aspartate acids (MGF D10).

SEQ ID NO: 12: Thrombin fragment TP508 con-jugated with 10 aspartate acids (TP 508 D10).

SEQ ID NO: 13: Osteopontin-derived peptide con-jugated with 10 aspartate acids via 4 mini PEG (ODP D10).

SEQ ID NO: 14: BMP9 with 10 aspartate acids (BMP9).

SEQ ID NO: 15: Ghrelin with 10 aspartate acids (Ghrelin D10).

SEQ ID NO: 16: CNP with 10 aspartate acids (CNP-D10).

SEQ ID NO: 17: VIP with 10 aspartate acids (VIP D10).

SEQ ID NO: 18: 4 mini PEG D10.

SEQ ID NO: 19: B2A_AHX3 with 10 glutamic acids (B2A_AHX3_e10).

SEQ ID NO: 20: F119 with 10 glutamic (F119).

SEQ ID NO: 21: JNK with 10 glutamic (JNK3_mp4_e10).

SEQ ID NO: 22: Lactoferrin with 10 glutamic acids (Lactoferrin_mp4_e10).

SEQ ID NO: 23: Osteostatin with 10 glutamic acids (Osteostatin_mp4_(D)E$_{10}$).

SEQ ID NO: 24: Preptin with 10 glutamic acids (Preptin (1-34)_mp4_e10).

SEQ ID NO: 25: QK with 10 glutamic acids (QK_mp4_e10).

SEQ ID NO: 26: Annexin 1 with 10 glutamic acids (QK_mp4_e10).

SEQ ID NO: 28: F2A with 10 glutamic acids (F2A_mp4_e10).

SEQ ID NO: 29: P2A with 10 glutamic acids (P2A-mp4_e10).

SEQ ID NO: 30: Targeting group consisting of a polypeptide, DDDDDDDDDD.

SEQ ID NO: 31: Targeting group consisting of a polypeptide, EEEEEEEEEE.

SEQ ID NO: 32: F2A with 10 glutamic acids (F2A_mp4_e10).

SEQ ID NO: 33: P2A with 10 glutamic (P2A-mp4_e10).

SEQ ID NO: 34: F119 with 10 glutamic acids (F1119).

SEQ ID NO: 35: Targeting group consisting of a polypeptide, EEEEEEEEEE.

SEQ ID NO: 36: P2A with 10 glutamic acids (P2A-mp4_e10).

SEQ ID NO: 37: Targeting group consisting of a polypeptide, EEEEEEEEEE.

SEQ ID NO: 38: Targeting group consisting of a polypeptide, DDDDD.

SEQ ID NO: 39: Targeting group consisting of a polypeptide, EEEEE.

SEQ ID NO: 40: Targeting group consisting of a polypeptide, DDDDDDDDDDDDDDDDDDDD.

SEQ ID NO: 41: Targeting group consisting of a polypeptide, EEEEEEEEEEEEEEEEEEEE.

SEQ ID NO: 42: A targeting sequence for F2A's receptor, YRSRKYSSWYVALKR.

SEQ ID NO: 43: Substance P with 4 mini PEG conjugated to D10 (SEQ ID NO: 18).

SEQ ID NO: 44: Single branch of B2A.

SEQ ID NO: 45: Targeting group consisting of a polypeptide, eeeeeeeeee, wherein each residue is a D-glutamic acid.

DETAILED DESCRIPTION

While the concepts of the present disclosure are illustrated and described in detail in the figures and the description herein, results in the figures and their description are to be considered as examples and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Aspects of the fracture targeted technology disclosed herein can help both civilians and military personnel. Bone fractures occur at an annual rate of 2.4 per 100 people and cost the US healthcare system approximately $28 billion per year. Of the 6.3 million bone fractures that occur annually in the US, 300,000 result in delayed union or non-union healing. Approximately 887,679 hospitalizations result each year from fractures. Over half (57%) of fractures resulting in hospitalizations occur in persons aged 65 and over. Estimated health care costs are indicated in Table 1, below.

TABLE 1

| Fracture | Healing time | Cost without surgery | Cost with surgery |
| --- | --- | --- | --- |
| Leg | 10-12 weeks) | $2,500 | $16,000 |
| Hip | 12+ weeks | $11,500 | $66,500 |
| Vertebral | (8+ weeks) | $5,000-15,000 | $50,000-150,000 |
| Arm | 6-10 weeks | $2,500 | $16,000 |

Currently, a substantial fraction of national defense outlays is devoted to combat-related medical expenditures, with a significant proportion of these costs devoted to treatment of orthopedic injuries. Indeed, ~$_{65}$% of all wounds associated with military conflicts since World War I (WWI) have included orthopedic injuries, and 26% of all injuries to an extremity have involved one or more broken bones. Treatment of bone fractures not only removes a soldier from service for an extended period of time, but also requires the attention of multiple additional personnel to treat, monitor and rehabilitate the injured soldier. Unfortunately, some orthopedic injuries are so severe that resolution of the damage never occurs, and the armed services are then obligated to care for the damaged combatant in perpetuity.

Fractured bones are not only an adverse consequence of combat, they also constitute a prominent repercussion of military training exercises. During the course of a soldier's schooling, a female recruit will have a 3.4-21% chance of suffering a stress fracture, while a male recruit will have a 1-7.9% probability of experiencing the same injury. While such maladies may at first seem trivial, statistics reveal that they cost the military ~$34,000 per soldier which totals up to ~$100 million in aggregate per year. Not surprisingly, many affected recruits eventually leave the military as a consequence of their stress fracture, which results in further expenses arising from wasted recruiting and training efforts. Therapies for fractured bones both within and outside of the military rely almost exclusively on mechanical stabilization of the damaged bone (i.e. use of a cast, pin, rod, or plate, etc.). In fact, the only FDA-approved drug for enhancing fracture repair is a bone anabolic agent that must be applied topically to the fracture surface during surgery. Needless to say, such a therapy is inappropriate when the surgery is not otherwise indicated, can only be administered once (i.e. during the brief period when the fracture surface is exposed), cannot be easily adapted for treatment of multiple fractures, and is never used for therapy of stress fractures. What is critically needed is obviously a systemically administered bone anabolic agent (i.e. as drug that can stimulate rapid bone fracture healing) that will concentrate selectively on the bone fracture surface and induce accelerated bone formation only at the damaged site. Surprisingly, nothing of this sort has ever been described in the literature.

Recognizing the enormous need for a systemically administered bone fracture-targeted healing agent, peptides and other molecules with structures that home specifically to bone fracture surfaces following intravenous or subcutaneous administration were identified. A second group of bone anabolic agents (for example, both bone growth stimulating hormones and cytokines as well as various low molecular weight bone growth-inducing drugs, etc.), that when linked to one of our bone fracture-homing peptides, would promote accelerated fracture repair, were also identified.

Fortunately, several fracture-targeted bone anabolic drugs met all initial requirements for advancement into large animal studies. That is, the targeted conjugates were found to: i) reduce the time for fractured femur repair in mice by roughly half, ii) induce no detectable systemic toxicity at its effective dose, iii) cause no ectopic bone formation at either the injection site or elsewhere), iv) lead to regeneration of bone at the fracture site that was biomechanically stronger than the contralateral (unbroken) femur, and v) result in eventual remodeling of the fractured region into normal cortical bone.

All in vivo data included herein are from Swiss Webster mice. All mice received an osteotomy on their right femur and received subcutaneous drug administration daily for either 2, 3 or 4 weeks, as indicated, for each compound. 1×concentration represents 1 nmol/day, 10× represents 10 nmol/day, 100×represents 100 nmol/day and most studies have an n of 5.

Aspects of the disclosure include conjugates sometimes written in the form of X-Y-Z, wherein each conjugate includes at least one moiety (X) that has the ability to effect bone growth, development, and/or healing, for example, anabolic agents, and a targeting moiety (Z) which has an affinity for bone and helps to direct the conjugate to bone. In some of these conjugates, the X and Z portions are joined together by a linker region (Y).

Targeting moieties (Z), many of which are explicit or implicitly disclosed herein, have the potential to target bone anabolic agents to bone fractures, ostectomies, and osteotomy sites. The compounds described here are composed of molecules with high affinity towards hydroxyapatite and a bone anabolic agent. Although targeting has been exemplified primarily with acidic oligopeptides, all molecules with affinity towards hydroxyapatite could be attached to a bone anabolic agent to improve fracture repair. These molecules include but are not limited to ranelate, bisphosphonates, tetracyclines, polyphosphates, molecules with multiple carboxylic acids, calcium chelating molecules, metal chelators, acidic amino acid chains of either d or L chirality. Each of the previously listed targeting molecules can be single units, polymers, dendrimers or multiple units. Other molecules can also be substituted for the targeting agent. These include peptides, proteins and manmade molecules that intercalate, bind to, adsorb to, or hybridize with: collagen, the extracellular matrix, heparan sulfate, chondroitin sulfate, keratan sulfate, hyaluronic acid, elastin, fibronectin, laminin, proteoglycans, basement membrane, extracellular polymeric substances, integrins, blood clotting factors, fibrinogen, thrombin, fibrin, and other extracellular macromolecules. It is also possible to target using a combination of the listed targeting molecules.

Definitions

Unless defined otherwise, all technical and scientific terms used herein have the same meaning as is commonly understood by one of ordinary skill in the art to which this disclosure pertains.

The term "BV/TV" means the bone volume divided by total volume of the 100 thickest micro CT slices of the fracture callus.

The term "TbTh" means the trabecular thickness of the 100 thickest micro CT slices of the fracture callus.

The term "Bv" means the overall bone volume of the 100 thickest micro CT slices of the fracture callus.

The term "TbSp" means the spacing between the trabecula in the 100 thickest micro CT slices of the fracture callus.

The term "Peak Load" means a postmortem 4 point bend of the healed femur. Peak load represents the maximum force the healed femur withstood before it refractured.

The term "D10" at the end of any name represents that the peptide is targeted to bone by a chain of 10 aspartic acids. D10 can be at the N-terminus or C-terminus of the specified peptide.

The term "E10" or "(D)E10" at the end of any name represents that the peptide is targeted to bone by a chain of 10 (D) glutamic acids.

The term "P4" means a fragment that represents the knuckle epitope in hBMP-2.

The term "P-4" corresponds to residues 73-92 of BMP-2 in which Cys-78, Cys-79, and Met-89 are changed to Serine (Ser), Ser, and Threonine (Thr). BMPs are well known regulators of bone and cartilage formation. BMPs bind as dimers to type I and type II Ser/Thr receptor kinases, forming an oligomeric complex that activates intracellular Smad proteins leading to their translocation into the nucleus where they serve as transcription factors to activate different OB differentiation markers (such as Runx2 (transcription factor for osteoblast differentiation)), leading to osteoblastogenesis. BMPs have also been shown to stimulate mesenchymal stem cells (MSC) differentiation to OBs by promoting recruitment of osteoprogenitor cells.

The term "AHX" in the middle of any name represents that the therapeutic is linked to the targeting peptide via a polymer of 6-(amino)hexanoic acid.

The term "AHX3" in the middle of any name represents that the therapeutic is linked to the targeting peptide via a polymer of (6-(amino)hexanoic acid)$_3$.

The term "mp4" in the middle of any name represents that the therapeutic is linked to the targeting peptide via a polymer of 4 minipegs as known as 8-Amino-3,6-Dioxaoctanoic Acid.

The term "STB" at the end of any name represents that the compound represents a chemically more stable version of its natural version.

Compounds which effect bone growth and may be used to practice aspects of the present disclosure include but are not limited to the following: growth factors, fragments of growth factors, or synthetic peptides or small molecules that mimic the action of growth factors. Examples of which may include but are not limited to: transforming growth factors (alpha or beta), insulin, insulin-like growth factors, fibroblast growth factor (1-23), erythropoietin, epidermal growth factor, colony-stimulating factors (including macrophage colony-stimulating factor, granulocyte colony-stimulating factor, granulocyte macrophage colony-stimulating factor), bone morphogenetic proteins (BMP) (1-8a, 8b, 10, 11, 15), angiopoietin, vascular endothelial growth factor, megakaryocyte growth and development factor, adrenomedullin, autocrine motility factor, ciliary neurotrophic factor, leukemia inhibitory factor, interleukin(1-7), ephrins(A1-5, B1-3), Foetal Bovine Somatotrophin, glial cell line-derived neurotrophic factor, neurturin, persephin, artemin, growth differentiation factor-9, hepatocyte growth factor, hepatoma-derived growth factor, keratinocyte growth factor, migration-stimulating factor, macrophage-stimulating protein, myostatin, neuregulins(1-4), neurotrophins, brain-derived neurotrophic factor, nerve growth factor, neurotrophin-3, neurotrophin-4, placental growth factor, platelet-derived growth factor, renalase, T-cell growth factor, tumor necrosis factor-alpha, Wnt signaling activators, parathyroid hormone-related peptide, parathyroid hormone, growth differentiation factor, Growth Hormone (GH), thyroid hormone, calcitonin, vitamin D, Apelin, Annexin, Bmp fragments including: OPD (BMP2), P-1(Bmp2), P24(bmp2), P4(BMP) HBD(bmp4), Bone Forming Peptide (BFP), BFP-1 (BMP-7), BFP-2(BMP-7), BFP-4(BMP-7), BFP-7 derived peptide, (bmp7), peptide b(BMP-7), BMP-9-derived peptide(bmp-9), pBMP-9(BMP-9), SpBMP-9(BMP-9), BMP2-L51P (BMP2), BMP2 108(BMP2), mBMP (BMP2), osteopromotive domain (OPD) (BMP2), PEP7 (BMP2), AB204(BMP2/ACTIVIN A), AB204-1 103Y(BMP2/ACTIVIN A), AB21 1 (BMP2/ACTIVIN A), AB215((BMP2/ACTIVIN A), BMP2/BMP9 chimera BB29, BMP6/BMP7 chimera 80, BMP7-E60KBMP6, THR-123 (BMP7), MB109 (BMP9), GDFS-S94N, GDFS-N445K, GDFS-N445T, GDFS-V453/V456, BMP2/6, BMP2/7, BMP4/7, Casein kinase 2 (CK2), CK2. 1, CK2.2, CK2.3; Fibroblast growth factor 2 fragments: Fl 05, Fl 19, F36, F77; Glucagon like peptide, Exen-din 4, exenatide, liraglutide, lixisenatide, albiglutide, dula-glutide, semaglutide, taspoglutide, Preptin, E peptide, mechano growth factor, Cathelicidin, Endothelin-1, OGP (osteogenic growth peptide), cyclic OGPIO-14, OGPIO-14, Ostabolin, Ostabolin-C, ZP2307, TP-508 Chrysalin, PBA2-1 c, QK, Amylin, ghrelin, GHRP-6, hexarelin, ipamorelin, amylin, human c peptide, vessel dilator, CNP, BMN 11, Osteoblast activating peptide, fMLF, hepcidin, PSI, Epoxomicin, bortezomib, Carfizmib, oprzomib, Epiregulin, Beta-cellulin, amphiregulin, Neuregulin, Stem cell factor, Agrin, Ephrin, Glial cell line-derived neurotrophic factor, neurtu-rin, artemin, Angiopoietins SPARC-113, SPARC-118, Osteoactivin, or a molecule stimulates JNK3 upregulation: such as JNK3, and arrestin 3 fragments, or annexinl.

Still other compounds which effect bone growth and may be used to practice aspects of the present disclosure include but are not limited to an angiogenic factor or a vasoactive compound that either stimulates angiogenesis or hematopoiesis, effects hematopoiesis, is released by or affects cells of a hematopoietic lineage, such as red blood cells, leukocytes, platelets, monocytes, or endothelial cells, or is a protein, peptide or other small molecule release in response to injury to blood vessel, or the full protein, peptide or fragments of such molecules or synthetic or small molecules that mimic their actions. Examples of which may include but are not limited to: VEGF, QK, SPARC 113, VIP, PACAP, Dobutamine, dopamine, isoprenaline, endothelin 1, phenylphrine, adrenaline, terlipressin, Angeotensin II, Ace inhibitors, FGF2, PDGF, Angiopoietin, Hypoxia inducable factors, MMP2, metaloproteases, sokotrasterol sulfate, 0-sitosterol, oversulfated exopolysaccharide, IGFlfumagillin, Vatanib, Axtinib, Placental growth factor, neuropilin, VE-cadherin, Alpha-v beta 3, afibercept, HIFlA, cediranib, Shingosinel-phosphate, 2 methoxyesterdiol, vandetanib, semanib, ephrin, ramucirumab, TIEl, Platelet activating vactor, Thrombin, TP508, fibrin, fibrinogen, von Willebrand factor, protease-activated receptor, serotonin, platelet activating factor, ATP, ADP, Thromboxane A2, factor X, factor VII, Factor IX, Hangeman factor, factor I, Factor VIII, Vitamin K, platelet factor 4, endothelium derived hyperpolarizing factor, prostaglandins, leukotrienes, notchagonists, LIF, Jagged, and memaquinone.

Bone Growth Modifiers and Delivery Peptides

```
                                          (SEQ ID NO: 1)
BFP1D10  DDDDDDDDDDGQGFSYPYKA VFSTQ
```

BFP (bone forming Peptide) a fragment of immature BMP7 is a 15-amino acid peptide corresponding to residues 100-115 of the immature form of BMP-7 which like BMP2 is involved in osteogenic differentiation, proliferation, and formation of new bone. This short peptide also induces osteogenesis calcium content in MSCs.

BMP-9

Figure 27:
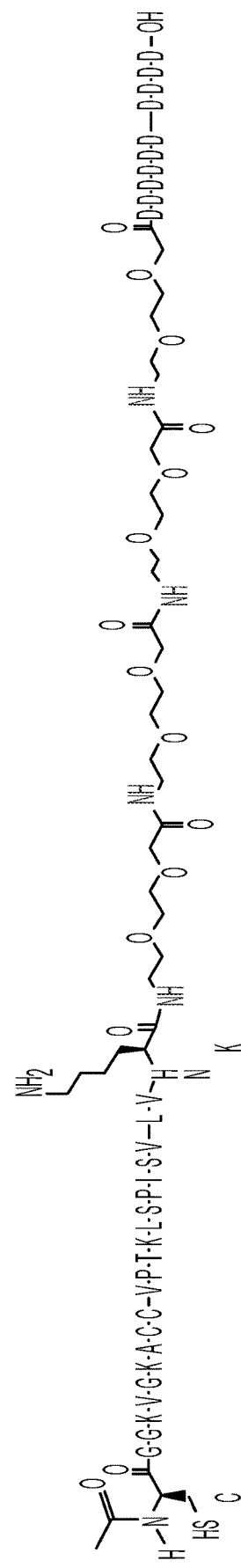
FIG. 27 depicts the structure for BMP9 (SEQ ID NO: 14) conjugated with D10 (SEQ ID NO: 30).

BMP-9 is also a potent regulator of osteogenesis and chondrogenesis and is a potent inducer of differentiation of osteoblasts. pBMP9 is a 23-residue peptide derived from residues 68-87 of the knuckle epitope of human BMP-9. The mechanism of action of this peptide is likely to involve the small mothers against decapentaplegic (Smad) pathway. The structure of BMP9 is depicted in FIG. 27.

Ghrelin D10

Figure 28:
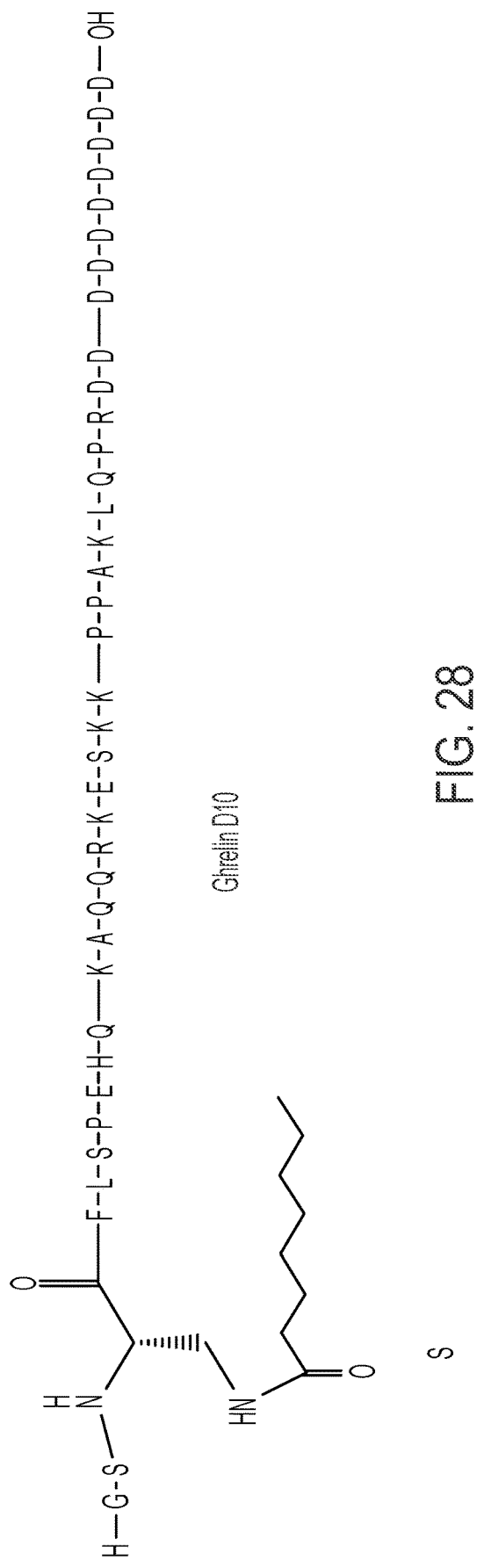
FIG. 28 depicts the structure for Ghrelin D10 where X at position 3 is diaminopropionic acid modified with an octanoyl group sidechain (SEQ ID NO: 5).

Ghrelin is a 28-residue peptide hormone synthesized primarily by the gastric fundus in response to fasting, and acts as a ligand of the growth hormone secretagogue (GHS) receptor (GHSR) to promote growth hormone release from the pituitary. Ghrelin stimulation at the GHSR leads to the proliferation of osteoblasts and prevents the apoptosis of osteoblasts through mitogen-activated protein kinase/extra-cellular signal-regulated kinases (MAPK/ERK) and phosphoinositide 3-kinase/protein kinase B (PKB) (PBK/AKT) pathways. Ghrelin also stimulates osteoprotegerin (OPG) gene expression, which inhibits the coupling between the osteoclasts and osteoblasts, leading to reduced osteoblast-related osteoclast differentiation. Increased OPG also and decreases osteoclast activity. Ghrelin is only active when the Ser-3 is acylated with octanoic acid. Our construct contains a stabilized version of this where Ser-3 was replaced with diaminopropionic acid. The structure of Ghrelin D10 as modified herein is depicted in FIG. 28.

Preptin D10

Figure 29:
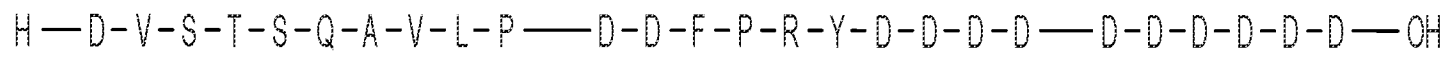

Preptin is a 34-residue peptide hormone that is secreted by the 13-cells of the pancreatic islets. This peptide corresponds to Asp-69 to Leu-102 of the E-peptide of proinsulin-like growth factor-II (pro-IGF-11). Preptin's anabolic effects on bone are exerted through its ability to stimulating osteoblasts s proliferation, differentiation, and promoting their survival. Preptin's proliferative effect is predicted to be facilitated through a G-protein-coupled receptor triggering phosphorylation of p42/44 MAP kinases. Some of preptin's anabolic effects are believed to be due to it stimulating an increase in a known bone anabolic connective tissue growth factor. While the native peptide effects glucose metabolism the first 16 amino acids are important for its anabolic effects and have no effects on glucose metabolism. The structure of Preptin D10 is depicted in FIG. 29.

CNP-D10 is a C-Type Natriuretic Peptide Targeted with D10

Figure 30:
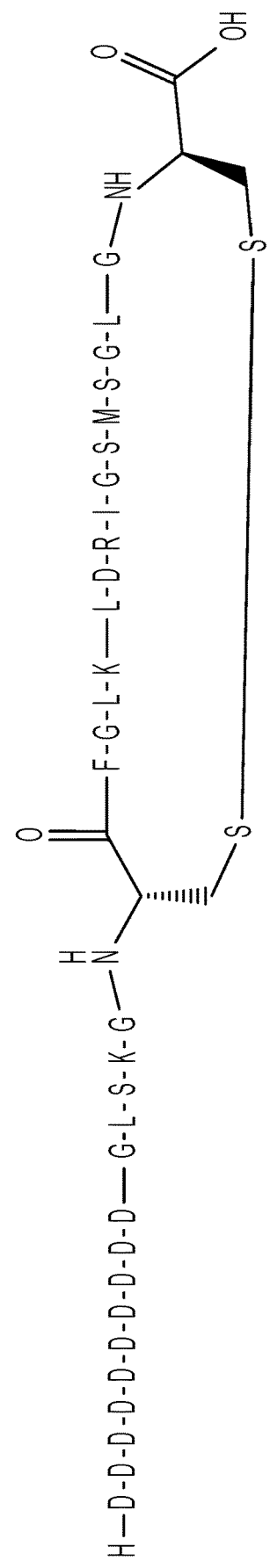
FIG. 30 depicts the structure for CNP-D10 (SEQ ID NO: 16).

C-Type Natriuretic Peptide (CNP) contains 22 residues stabilized by an intramolecular disulfide linkage between Cys-6 and Cys-22 it functions as a local regulator of vascular tone, possibly due to its strong vasorelaxant properties. CNP also acts on the differentiation and proliferation of OBs, OCs, and chondrocytes via an autocrine/paracrine process through binding to the natriuretic peptide receptor B (NPR-B). CNP activates bone turnover and remodeling. Endochondral ossification is another mechanism of bone formation affecting chondrocytes. It involves the conversion of an initial cartilage template into bone such as long bones and vertebrae. CNP has been shown to be an important anabolic regulator of endochondral ossification. The structure of CNP-D10 is depicted in FIG. 30.

VIP D10 is Vasoactive Intestinal Peptide Targeted with D10

Vasoactive intestinal peptide (VIP), a neuropeptide that consists of 28 amino acids and originally isolated from porcine intestine. VIP has several effects however its receptors are present on the nerves that rapidly innervate the fracture callus. It has been shown to be an important regulator of bone formation. VIP exerts its biological effects through the G-protein-coupled receptors (VPAC1, VPAC2, and PAC1). Signaling through these receptors also enhanced cell osteoblast differentiation and proliferation. It also increases expressions of collagen type I, osterix (OSX), and alkaline phosphatase (ALP) through signaling at the VPAC2 receptor by triggering an increase in intracellular calcium. VIP also increases the expressions of BMPs and the nuclear presence of Smad1 transcription factor, which can activate various bone-specific genes. VIP also enhances osteoblast proliferation and mineralization through increased gap junction intercellular communication (GJIC) between osteoblasts. VIP also affects the differentiation of osteoclasts thus leading to an increase in bone resorption. The structure of VIP D10 is depicted in FIG. 31.

Substance P with 4 Mini PEG Conjugated to D10

Figure 32:
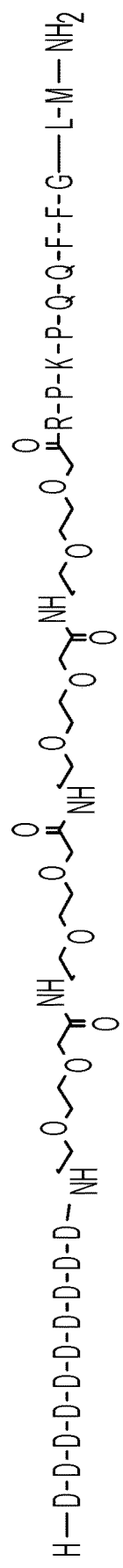
FIG. 32 depicts the structure for Substance P with 4 mini PEG conjugated to D10 (SEQ ID NO: 43).

Substance P is an I I-amino acid long pro-inflammatory neuropeptide belonging to the tachykinin family. Substance P improves mineralization of osteoblasts and the expression of osteogenic markers at late-stage bone formation, by activating neurokinin-1 receptor, a G-protein coupled receptor found in the central and peripheral nervous systems. Also, substance P reduces osteoclastogenesis and bone resorption. Substance P upregulates the expressions of collagen type 1, ALP, Runx2 and osteocalcin in osteoblasts this effect involves the activation of Wnt/I3-catenin signaling pathway. Substance P promotes differentiation and migration capability of rat bone marrow MSCs and activates BMP-2 expression in osteoblasts. Some of substance p's anabolic effects are attributed to in human to increases in osteoblast proliferation and mineralization through increased gap junction intercellular communication between osteoblasts. Gap junction intercellular communication has important roles in conveying the anabolic effects of hormones and growth factors and regulating transcription of osteogenic markers. The structure of Substance P with 4 mini PEG conjugated to D10 is depicted in FIG. 32.

CBMD10 is the Collagen Binding Motif of Osteopontin Targeted by D10

CBM collagen binding motif is the highly conserved 28-residue collagen binding motif (CBM) (residues 150-177) of human osteopontin. Osteopontin, a glycosylated phosphoprotein prominently localized in the extracellular matrix (ECM) of mineralized bone tissue to form a complex with collagen in bone tissue, thereby inducing mineralization of collagen fibrils. CBM enhances osteoblast differentiation of human MSC. CBM causes osteogenic differentiation of human bone marrow MSCs and increases mineralized of bone. CBM works in human MSCs by increasing extracellular Ca' influx, which leads to the activation of CaMKII and the subsequent phosphorylation of ERK1/2, ultimately influencing OB differentiation. The structure of VIP D10 is depicted in FIG. 33.

ODP D10

Osteopontin-derived peptide (ODP), a 15-residue peptide derived from rat osteopontin. ODP like CBM is a fragment of extracellular protein involved in the mineralization of collagen. ODP receptor mediated attachment and migration of osteoblasts and fibroblasts to the fracture site. ODP improves the proliferation and migration of osteoblasts. Though the signaling pathways are not completely elucidated for this molecule its believed that it works in a similar mechanism as CBM. The structure of ODP D10 is depicted in FIG. 34. DC-23, (SEQ ID NO: 2)
OGP-D10: DDDDDDDDDDALKRQGRTL YGFGG OGP-targeted Osteogenic growth peptide (OGP) is composed of a 14-AA residue identical to the C-terminus of histone 4 conjugated to an acidic oligopeptide at the N-terminus. Systemic administration of free OGP has been shown to improve fracture repair by improving the mineralization of cartilaginous fracture callus.

(SEQ ID NO: 11)
MGF-DDDDDDDDDDYQPPSTNKNTKSQRRKGSTFEEHK

Targeted mechano growth factor (MGF) E peptide is a splice variant of insulin-like growth factor I (IGF-I) with a targeting acidic oligopeptide on the N terminus. MGF causes osteoblast proliferation through the MAPK-ERK signaling pathway. Local injections (57 ug/kg) in rabbit bone defects 5 mm demonstrated accelerated healing through osteoblast proliferation.

(SEQ ID NO: 12)
TP508- DDDDDDDDDDAGYKPDEGKRGDACEGDSGGPFV

Targeted TP-508 is a prothrombin peptide that has been modified on the N-terminus with an acidic oligopep-tide. The anabolic portion of TP-508 has been used in clinical trials for repairing foot ulcers. Free TP-508 has a proliferative effect on osteoblasts. Local injections have demonstrated accelerated fracture repair in older rats.

B2A Peptide

B2A is a synthetic, multidomain peptide with two 19 amino acid branches derived from the region which is similar to the TGF-P/BMP-binding region of fetuin, a member of the cystatin family of protease inhibitors. The 19 amino acid branch acts as a BMP receptor ligand. BMP receptor activation is well known to osteogenic as BMP2 is currently approved to treat bone fractures. However existing strategies rely on the use of a full recombinant human protein. B2A is a dimer peptide that achieves similar levels of BMP receptor activation with a much mass. Bone morphogenetic protein receptor (BMPR) activation is canonically associated with activation of the small mothers against decapentaplegic (Smads) pathway BMPR ligands can, activate non smad signaling via p38, extracellular signal-regulated kinases 1 and 2 (ERK1/2), stress-activated protein kinase/c-Jun N-terminal kinase (SAPK/JNK), and protein kinase B (Akt/PKB). non smad signaling is key incell survival, nutation and metabolism and migration. B2A has the ability to bind both type I and II receptors for BMP. In the presence of BMP-2, B2A augments osteo-differentiation. In the absence of BMP-2, B2A-induced proliferation, aggrecan synthesis, and collagen accumulation in mesenchymal stem cells. Here by targeting B2A to the fracture, the osteogenic signal that locally applied BMP2 can be specifically localize to allow a much smaller much less invasive to apply form. The structure of B2A is depicted in FIG. 35.

F2A (Growth Factor)

F2A_mp4_e10 is made up of two copies of the fibroblast growth factor (FGF) receptor targeting sequence from FGF2 branching from a single lysine then 4 mini pegs to act a linker and spacer and 10 D glutamic acids to target to the bone. F2A's receptor targeting sequence is YRSRKYSS-WYVALKR (SEQ ID NO: 42) derived from derived from native FGF-2 (residues from 106 to 120). It has been shown to be nearly as potent as the full native protein at stimulating angiogenesis and osteogenesis in its dimer form. FGF2 is an anabolic growth factor heavily involved in wound healing and tissue repair. It Is both angiogenic and osteogenic. Fgf2 has shown promise as a protein treatment for wound healing. The advantage F2A e10 is its small size allows for better perfusion and the e10 allows it to chemically home to the damaged tissue site from a noninvasive injection at a distal site. The structure of F2A is depicted in FIG. 40.

F119 (Growth Factor)

Figure 84:
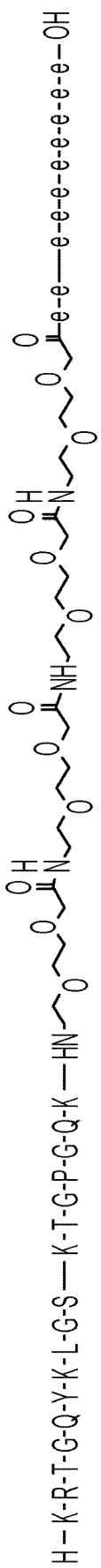
FIG. 84 depicts the structure for F119 (SEQ ID NOS: 20 and 45).

F119 is a heparin binding fragment from growth factor fibroblast growth factor 2. Fibroblast growth factor (FGF)-2 regulates a variety of cellular functions, such as proliferation and differentiation, by binding to cell surface FGF receptors (FGFRs) in the presence of heparin proteoglycans. F119 is a heparin binding site for fgf2 which corresponds to 119-135 of fgf2 (F119, KRTGQYKLG-SKTGPGQK (SEQ ID NO: 34). F119 interacts with cell-surface heparan sulfate proteoglycans. In addition, osteoblast differentiation, confirmed by ALPase activity and mineralization, is increased by F119. The structure of F119 is depicted in FIG. 84.

c-Jun NH2-terminal Protein Kinases (JNK3)

The c-Jun NH2-terminal protein kinases (JNKs) belong to the MAPK family. JNKs regulate normal physiological processes of cell proliferation, apoptosis, differentiation, and migration7.

Figure 49:
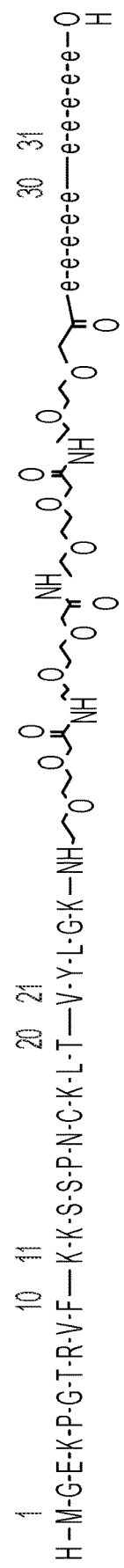
FIG. 49. Structure of JNK3_mp4_e10 (SEQ ID NOS: 21 and 45).

JNKs were also implicated in many diseases, from cancer to neurological and immunological disorders recently they were implicated as one of reasons adults bones don't have the same response to mechanical stimuli. It was found that increasing JNK3 activity stimulated more responsiveness to osteoinductive activity Arres-tin-3 facilitates INK activation in cells, and a short 25-residue arrestin-3 peptide was identified as the critical JNK3-binding element. It was demonstrated that this 25 residue peptide, JNK3, also binds mitogen-activated protein kinase 4 (MKK4), MKK7, and apoptosis signal-regulating kinase 1 (ASK1), which are upstream JNK3-activating kinases. This peptide is sufficient to enhance JNK3 activity in cells. The increases the responsiveness osteogenic signals that occur during bone fracture repair. Thus restoring the regenerative abilities of youth to adults. The structure of JNK3 is depicted in FIG. 49.

Lactoferrin

Lactoferrin is an iron-binding glycoprotein that belongs to the transferrin family. It is present in breast milk, in epithelial secretions, and in the secondary granules of neutrophils. In healthy subjects lactoferrin circulates at concentrations of 2-7×10-6 g/ml. Lactoferrin is a pleiotropic factor with potent antimicrobial and immunomodulatory activities. It has shown that lactoferrin can also promote bone growth. Lactoferrin is stimulatory towards osteoblasts and prevents osteoclastogensis. It has been shown that that lactoferrins interactions with osteoblast like cells is primarily through LRP1, a member of the family of low-density lipoprotein receptor-related proteins that are primarily known as endocytic receptors. Lactoferrin also induces activation of p42/44 MAPK signaling in primary osteo-blasts, but the two pathways seem to operate independently as activation of MAPK signaling, but not endocytosis, is necessary for the mitogenic effect of lactoferrin. Lactoferrin is too large to act as a good therapeutic. But several active fragments of lactoferrin have been identified. Lactoferricin which is a loop region from then terminus of Lactoferrin has been shown to have both antimicrobial and osteogenic effects.[4,5] Our targeted compound comes from residues 17-31 from the n terminus followed by a 4 minipeg spacer and linker and 10 D glutamic acids to home it to bone.

Figure 54:
FIG. 54. Structure of Lactoferrin_mp4_e10 (SEQ ID NOS: 22 and 45).

The structure of lactoferrin is depicted in FIG. 54.

Osteostatin (PTHrP [107-139])

Figure 59:
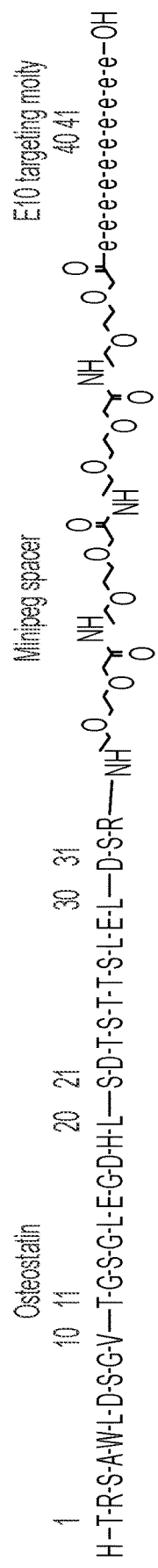
FIG. 59. Structure of Osteostatin_mp4_(D)E$_{10}$ (SEQ ID NOS: 23 and 45).

Osteostatin (PTHrP[107-139]) is a fragment of Parathyroid hormone related protein(PTHrP) that has been reported to be more anabolic than 1-34 of PTHrP. PTHrP is anabolic on bone both because of an inhibitory effect on osteoclast but mostly a stimulatory effect on osteoblasts. Some of its effect is believed to function like PTHrP though WNT signaling and also through interactions with the vascular endothelial growth factor (VEGF) receptor to increase survival of osteoblasts. The structure of osteostatin (PTHrP [107-139]) is depicted in FIG. 59.

P2A (Platelet-Derived Growth Factor (PDGF))

Figure 65:
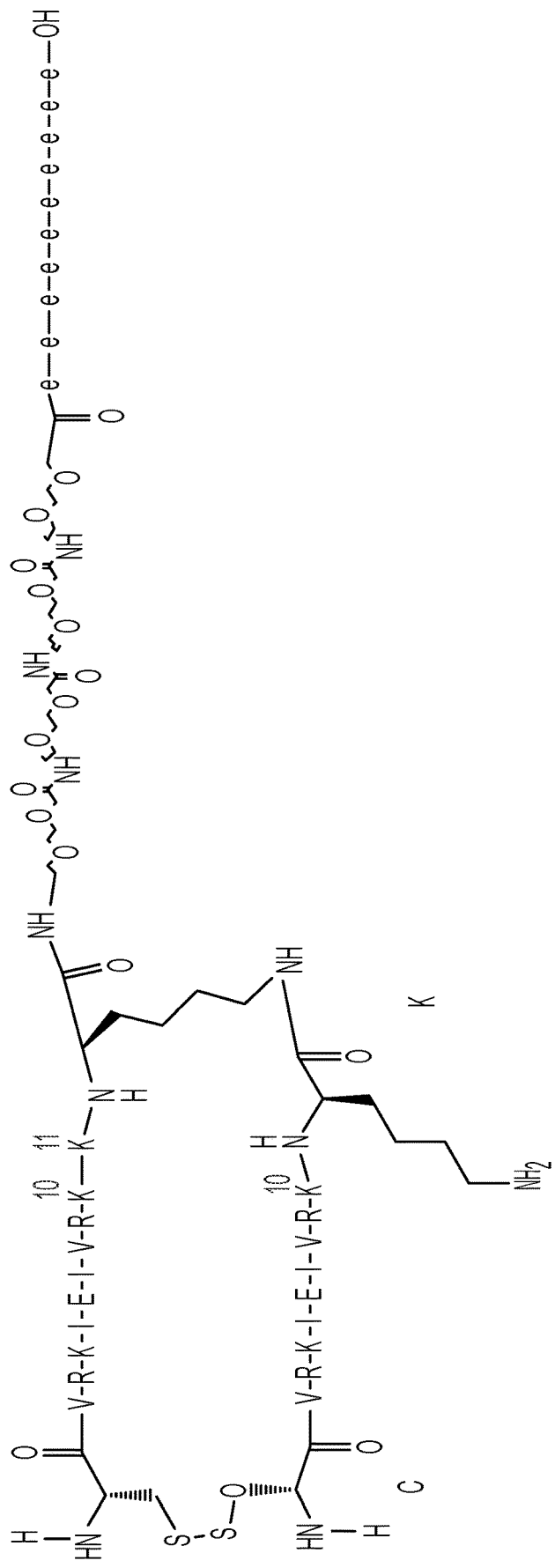
FIG. 65. Structure of P2A-mp4-e10 (SEQ ID NOS: 29, 36, and 45).

Platelet-derived growth factors (PDGFs) are mito-gens for many cells primary of mesenchymal origin and their involvement in wound healing has lead to the therapeutic use of recombinant human PDGF-BB, one of PDGF family. PDGF are released by plates at the site of fractures are chemotactic and mitogenic for osteoblast lineage cells and osteoblasts and therefore may enhance fracture healing by attracting osteoprogenitor cells to the fracture by chemotaxis and amplifying their quantity by mitogenesis. Further, PDGF-3B upregulates the expression of angiogenic vascular endothelial growth factor (VEGF), a key molecule for bone regeneration. PDGF-BB is approved to accelerate ankle fusion. It was found that a Arg160, Lysl61 and Lysl62 in PDGF-BB are required for mitogenic activity and high-affinity receptor. It was shown that a chain containing a branched dimer of VRKIEIVRKK (SEQ ID NO: 33) derived from residues 153-162 of PDGF-BB was almost as active as the full PDGF-BB. The targeted construct of the present disclosure consists of that cyclized branched dimer of VRK-IEIVRKK (SEQ ID NO: 33) derived from residues 153-162 of PDGF-BB, with a 4 mini peg spacer and 10 (D) glutamic acid to localize it to the site of the fracture. The structure of P2A is depicted in FIG. 65.

Preptin(1-34)

Figure 70:
FIG. 70. Structure of Preptin (1-34) mp4_e10 (SEQ ID NOS: 24 and 45).

Preptin is a 34-residue peptide hormone that is secreted by the 13-cells of the pancreatic islets. This peptide corresponds to Asp-69 to Leu-102 of the E-peptide of proinsulin-like growth factor-II (pro-IGF-11). Preptin's anabolic effects on bone are exerted through its ability to stimulating osteoblasts s proliferation, differentiation, and promoting their survival. Preptin's proliferative effect is predicted to be facilitated through a G-protein-coupled receptor triggering phosphorylation of p42/44 MAP kinases. Some of Preptin's anabolic effects are believed to be due to it stimulating an increase in a known bone anabolic connective tissue growth factor. While the native peptide effects glucose metabolism the first 16 amino acids are important for its anabolic effects and have no effects on glucose metabolism. The structure of Preptin(1-34) is depicted in FIG. 70.

QK (Vascular Endothelial Growth Factor (VEGF))

Figure 76:
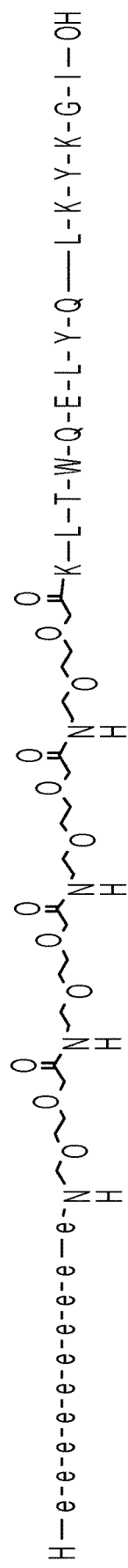
FIG. 76. Structure of QK_mp4_e10 (SEQ ID NOS: 25 and 45).

The vascular endothelial growth factor (VEGF) is the main regulator of angiogenesis. It elicits its proangio-genic activity by binding to two membrane receptors (VEGFR1 and VEGFR2) on the surface of endothelial cells (ECs). The binding of the natural ligand to VEGFR2 induces receptor dimerization and autophosphorylation of the intracellular kinase domain, which activates intracellular pathways ending in proliferation, migration, survival, and definitively triggering of the proangiogenic cellular response. Recently a de novo synthesized VEGF mimetic, named QK that shares the same properties as VEGF. This mimetic is a 15 amino acid peptide which adopts a very stable helical conformation in aqueous solution that resembles the 17-25 a-helical region of VEGF165, and binds both VEGFR-1 and 2. QK recapitulates all of VEGFs properties of angiogenesis, vasodilation and most importantly wound healing. It is well established that VEGF improves the spread at which a wound heals. The quicker the blood supply is returned to normal the faster the body can repair itself Full VEGF is difficult to control and use as drug to treat internal damage. But the targeted construct of the present disclosure takes the power of QK and homes it just to the damage site to control the site of angiogenesis to jus the desired region. The construct of the present disclosure is made up of the bone targeting ligand of the present disclosure attached to a mini-peg spacer and then to QK on its N terminus. The structure of QK is depicted in FIG. 76.

Annexin-1

Figure 81:
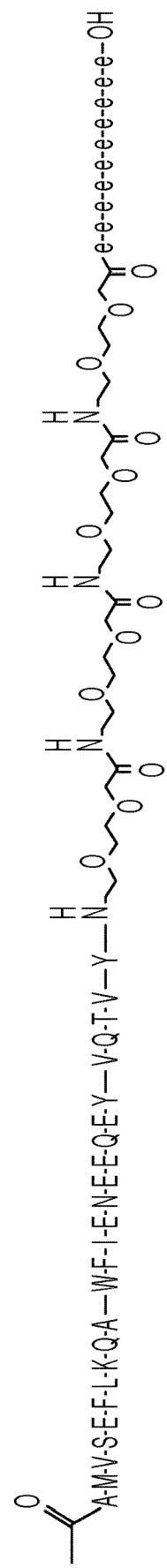
FIG. 81 depicts the structure for Annexin 1 (SEQ ID NOS: 26 and 45).

Annexin-1 is a family of phospholipid-binding proteins found in many tissues including bone marrow.363 The N-terminal fragment of annexin-1, Anx (2-26) is an endogenous ligand agonist of FPRI. Anx (2-26) promotes chemotactic migration and OB differentiation of MSCs via FPR1. The N-formyl peptide receptor (FPR) is a chemoat-tractant receptor belonging to the G-protein coupled receptor family. It is expressed in human bone marrow derived MSCs and is functionally involved in promoting MSC adhesion to extracellular matrix protein-coated surfaces as well as migration to sites of fracture for tissue regeneration. The structure of Annexin-1 is depicted in FIG. 81.

Material and Methods

Solid Phase Peptide Synthesis

Unless noted otherwise, the conjugates of the present disclosure are synthesized using the following synthesis. In a solid phase peptide synthesis vial capable of bubbling nitrogen, Wang resin (0.39 mmol/g) was loaded at 0.39 mmol/g with the first amino acid overnight in dichloromethane (DCM) and diisopropyl ethyl amine (DIPEA). The resin was then capped with acetic anhydride and pyridine for 30 minutes, followed by three washes of DCM and dimethylformamide (DMF), respectively. Following each amino acid coupling reaction, fluoroenylmethyloxycarbonyl (Fmoc) groups were removed by three 10 minute incubations with 20% (v/v) piperidine in DMF. The resin was then washed 3× with DMF prior to the next amino acid being added. Each amino acid was added in a 5-fold excess with N,N,N'N'-Tetramethyl-O-(1H-benzotriazol-1-yl)uronium hexafluorophosphate (HBTU) in DIPEA. Upon completion of the synthesis, peptides were cleaved using 95:2.5:2.5 trifluoroacetic acid:water:triisopropylsilane. Cysteine containing peptides were cleaved using 95:2.5:2.5 trifluoroacetic acid: triisopropylsilane:water; and 10 fold tris(2-carboxyethyl) phosphine (TCEP).

Cyclization Method for Disulfide Bridged Cyclic Peptides

For Amylin(1-8) and CGRP, the standard synthesis of the linear form of the cyclic peptides Fmoc Cystine with Acetamidomethyl protecting group on the sulfur was used. Then, to cyclize the peptide, the Cys(Acm) On-Resin was suspended the linear peptide resin in N,N-dimethylformamide (DMF) (approximately 1 mL/gram of resin). Then, the resin was treated with 10 equiv. of iodine (I2) in DMF/H2O 4:1 (v/v), approximately 1 mL/gram of resin). Then, argon gas was bubbled through the reaction mixture at room temperature for 40 minutes. Then, the resin was filtered and washed 3 times with DMF, 2 times with 2% ascorbic acid in DMF, 5 times with DMF, and 3 times with dichloromethane (DCM). Then, proceeded with normal n terminal fmoc deprotection and cleavage from the resin with normal cleavage solution with no TCEP added to preserve the disulfide bond. The peptides were then as all peptides purified using reverse phase chromatography on an HPLC using a 0-50% 20 mM ammonium acetate:acetonitrile gradient. The product was then identified from the appropriate fraction using LCMS and lyophilized to recover it from the water:acetonitrile mixture. All compounds were dissolved in sterile phosphate buffered saline (PBS) at the appropriate dose concentrations for drug delivery.

General Methods for Obtaining Test Data

The targeted conjugates were synthesized using standard Fmoc solid-phase peptide synthesis, as described above. To ensure the conjugates' activity, mouse pre osteo-blast (MCTC3-1) cells were treated with the targeted and untargeted compounds for three days at concentrations from 1 pM to 100 nM. After three days of treatment, the cells were harvested, and the ribonucleic acid (RNA) was purified from the cells. Expression levels of ALP, RUNx2, OSX, osteopontin (OPN), collagen 1A (Col-1A), OPG, RANKL, sclerostin gene (SOST), and OC were quantified via quantitative reverse transcription polymerase chain reaction (RT-qPCR). Once the biological activity of the conjugates was confirmed, they were tested in vivo in a fracture model. Aseptic surgical techniques were used to place a 23-gage needle as in intramedullary nail in the femur of anesthetized, 12-week-old Swiss Webster mice for internal fixation before fracture. Femur fractures were induced using a drop weight fracture device from RISystem. The mice received buprenorphine for three days post fracture. The mice were dosed subcutaneously each day for two weeks, three weeks, 4 weeks, or 17 days. Fracture healing was assessed using microCT (Scanco Medical Ag). Morphometric parameters were quantified in the 100 widest slices of the fracture callus. Trabecular thickness (TbTh), trabecular spacing (TbSp), total volume (TV), and volume of calcified callus (BV) were calculated. Fractured femurs were tested for strength in a four-point bend to failure using an Electro Force TestBench (TA Instruments). Lower supports were 10 mm apart on the anterior face of the femur in contact with the proximal and distal diaphysis. Upper supports were 4 mm apart and spanned the entire fracture callus on the diaphysis. Force was applied from the posterior face of the femur with a displacement rate of 0.3 mm/sec. Peak load, yield load, stiffness, displacement post yield, work to fracture, and deformation data were generated. Statistical analysis was performed using a two-way analysis of variance (ANOVA) and a Tukey post-hoc analysis with significance reported at the 95% confidence level. All animal experiments were performed in accordance with protocols approved by Purdue University's Institutional Animal Care and Use Committee (IACUC).

EXAMPLES

Figure 2:
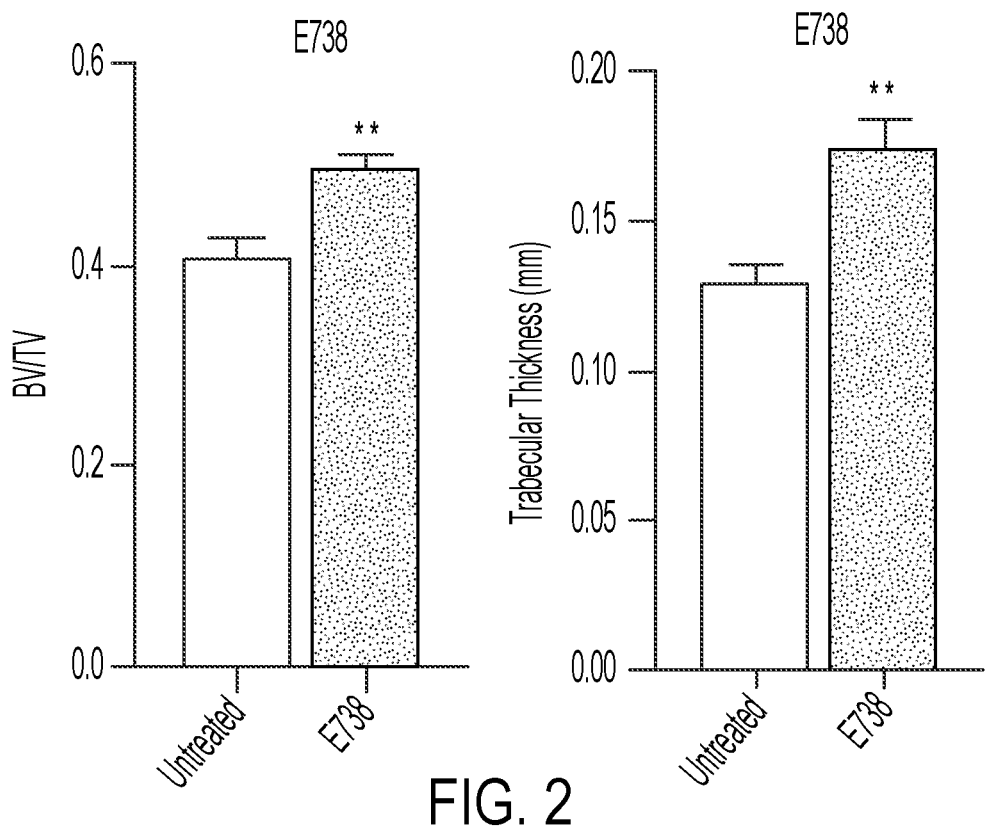
FIG. 2 depicts BV/TV and Trabecular Thickness using targeted E738 conjugate (1 µmol/kg), subcutaneously dosed every-other-day to fracture-bearing Charles River's breed (CFW) of Swiss Webster mice. Targeted E738 conjugate significantly improved the bone density and trabecular thickness at the fracture callus.

Example 1. Targeted Delivery of Src Kinase Inhibitors to Fracture Site for Accelerated Healing Example 1 shows representative Src kinase inhibitors Dasatinib and E738 (structures shown in FIGS. 3-4 respectively) effectively increased the bone density of the fracture callus when they are conjugated with acidic aspartic acids. See FIGS. 1-2, where bone density of the fracture callus from the targeted Dasatinib group is twice as dense as the saline group, and 50% denser than the free Dasatinib group; targeted E738 conjugate has significantly improved the bone density and trabecular thickness at the fracture callus. The structure of CBMD10 is depicted in FIG. 33.

Figure 5:
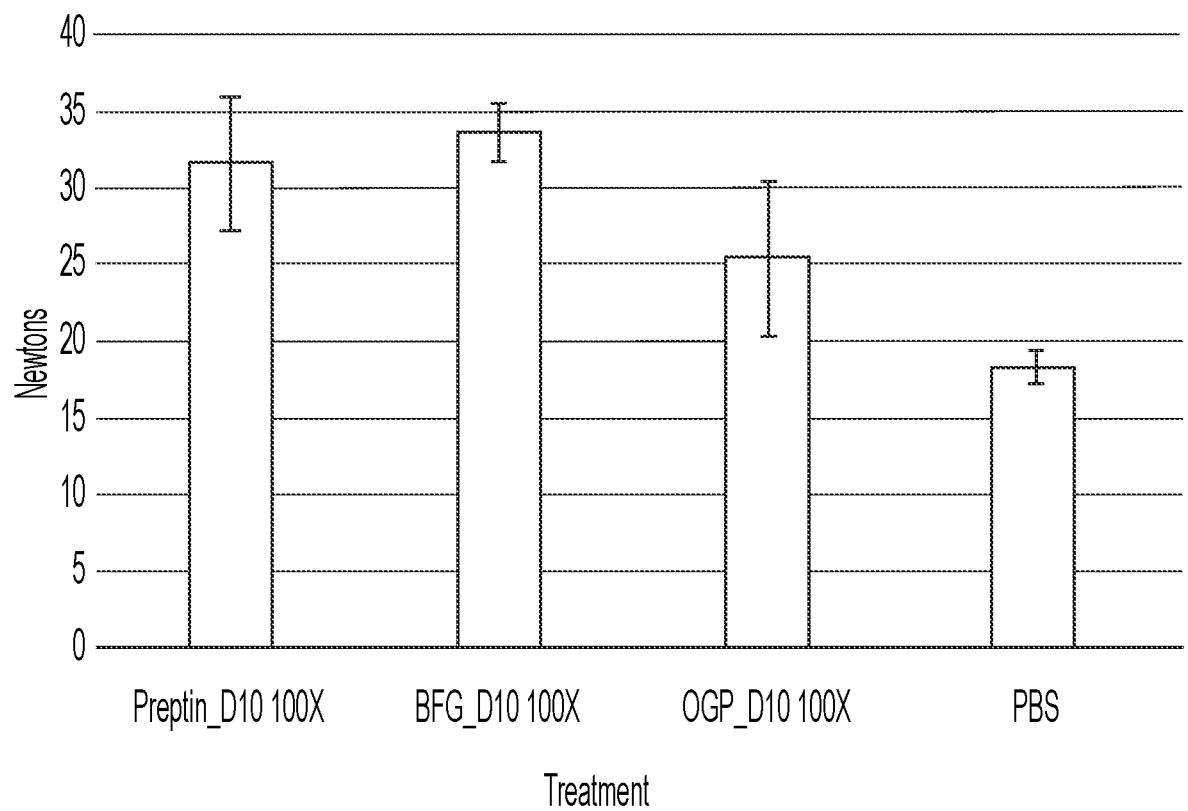
FIG. 5 depicts peak load of Fractured Femurs after 2 weeks.

Example 2. Representative Anabolic Peptides on Peak Load of Fractured Femurs after Two Weeks Example 2 provides the maximum force a representative anabolic peptide induced healed femur can withstand before it refractured. As shown in FIG. 5, bone morphogenetic protein pathway signaling peptide BFP-D10 with 100 nmol/day (100×) treatment obtained the maximum peak load, followed by IGF derived peptide of Preptin-D10 100×, and Osteogenic growth peptide (OGP-D10 100×), as compared to PBS.

Example 3. Preptin(1-16) (Preptin D10) Efficacy on Fracture Healing

Figure 6:
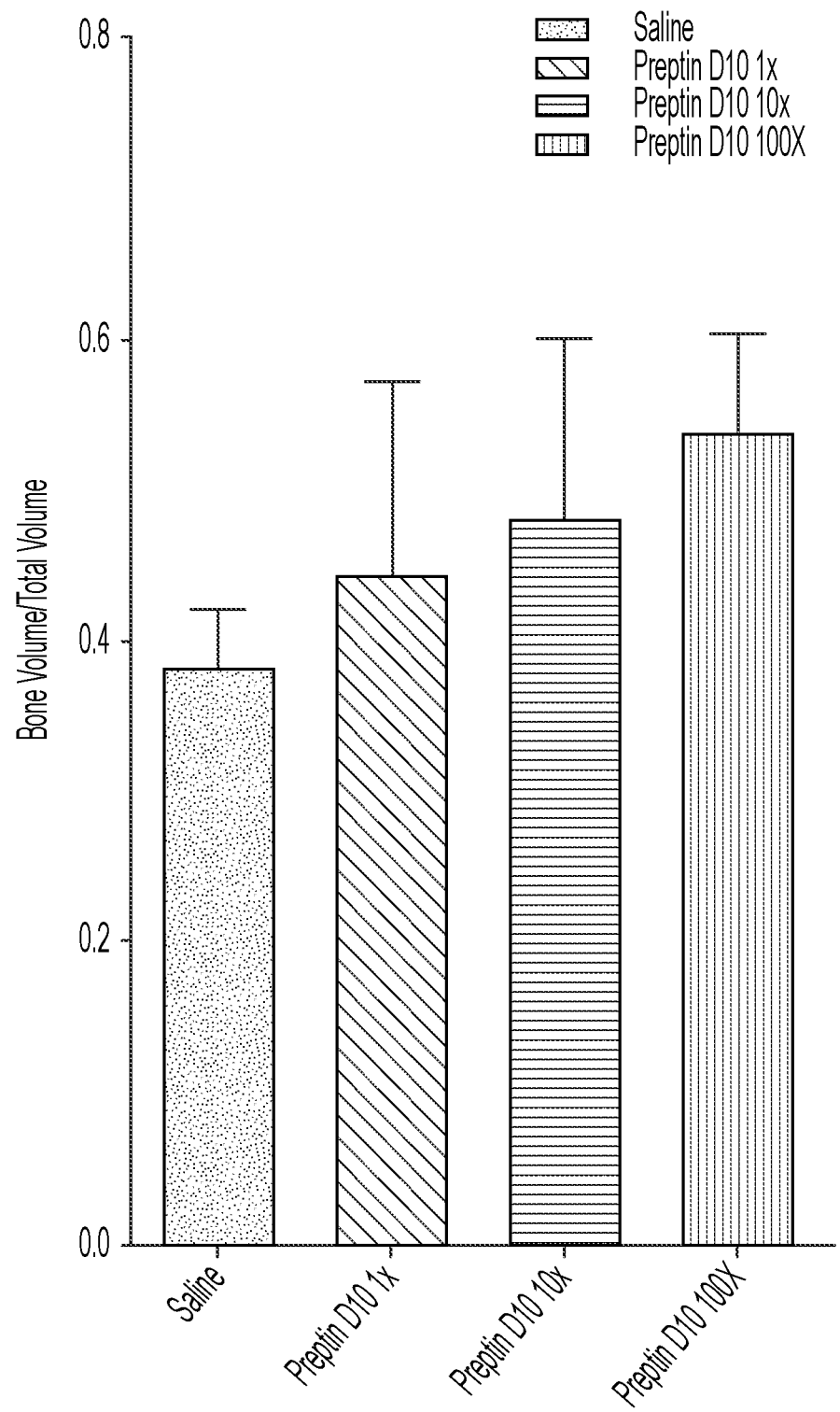
FIG. 6 depicts BV/TV two weeks after fractured femur received various concentration of Preptin D10 treatment.
Figure 7:
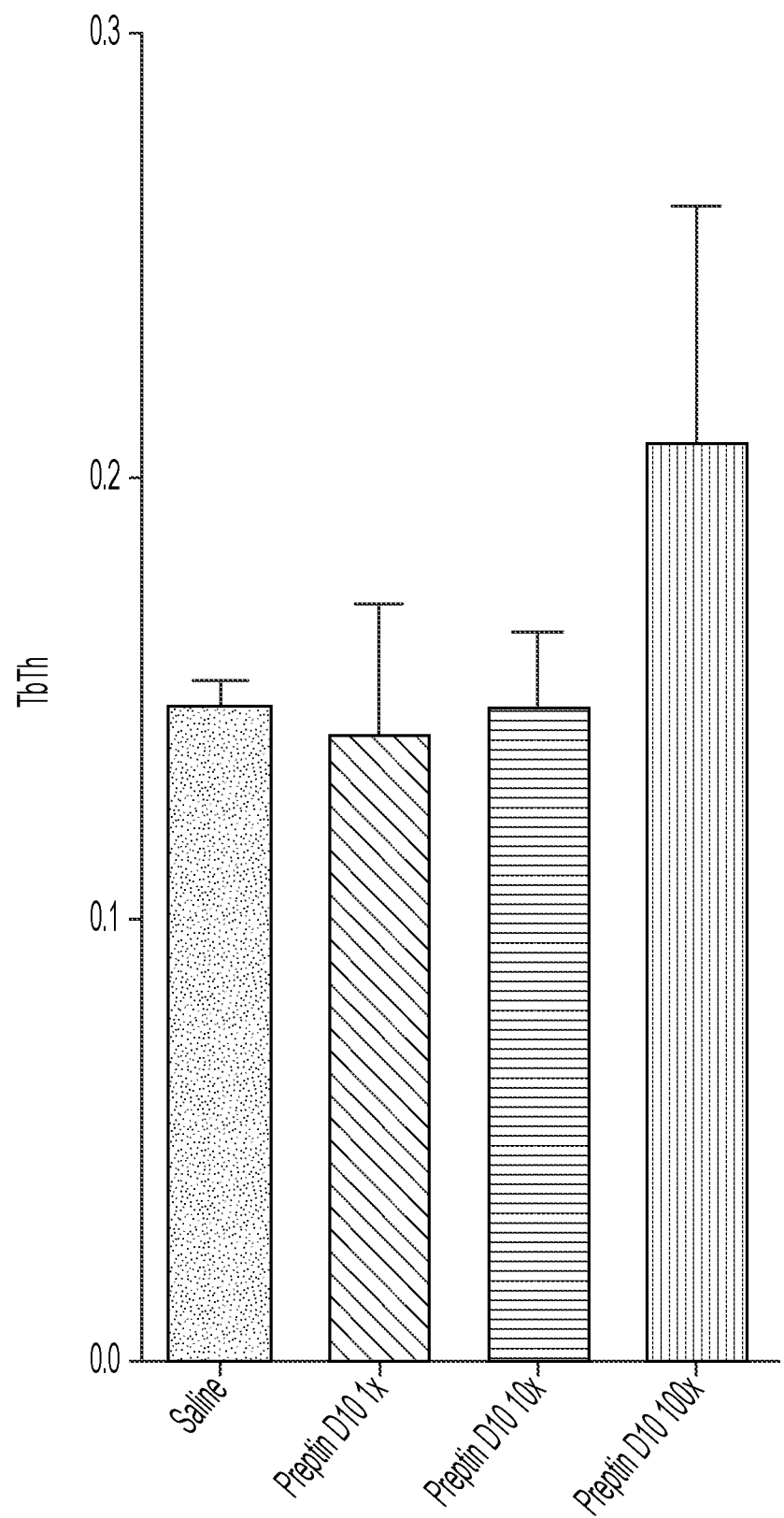
FIG. 7 depicts TbTh (the trabecular thickness of the 100 thickest micro computed tomography (CT) slices of the fracture callus) two weeks after fractured femur received various concentration of Preptin D10 treatment.
Figure 8:
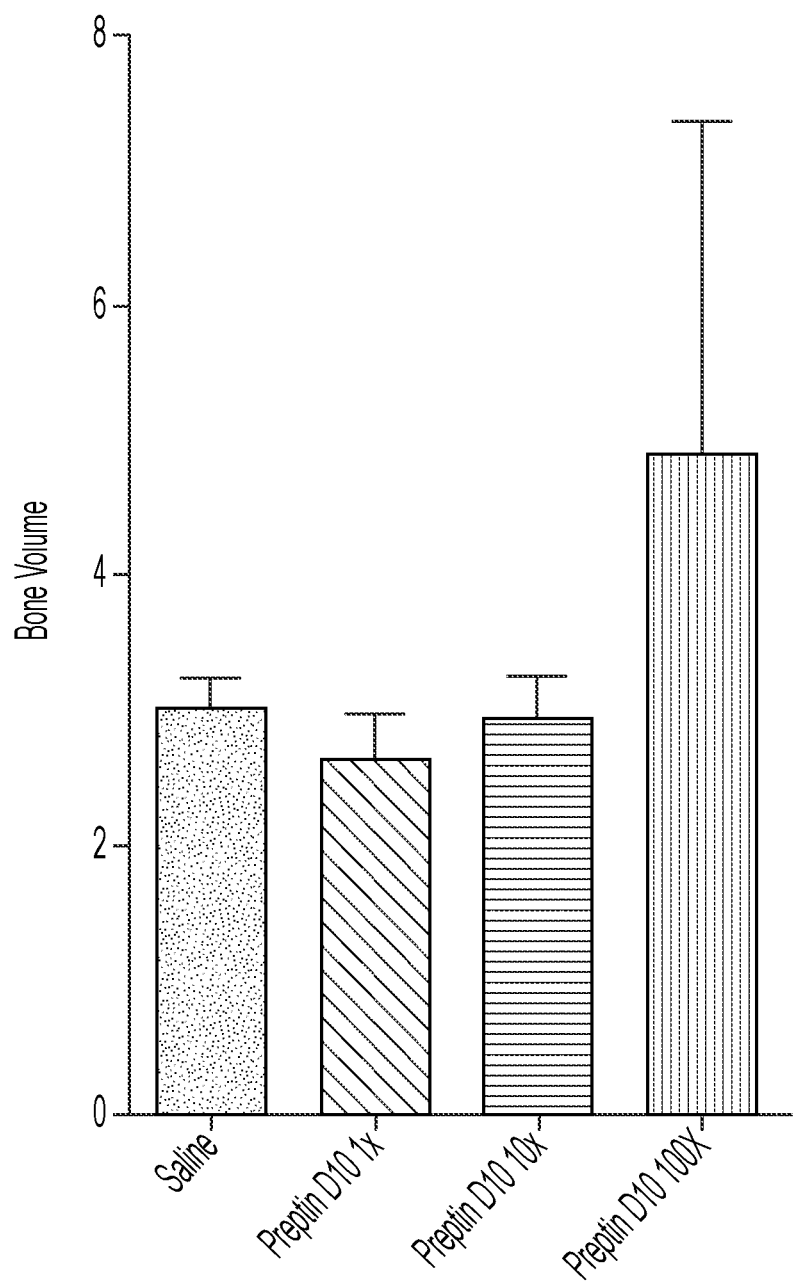
FIG. 8 depicts BV (the overall bone volume of the 100 thickest micro CT slices of the fracture callus) two weeks after fractured femur received various concentration of Preptin DI 0 treatment.

Example 3 indicates Preptin D10 effect on healing fractured bone after 2 weeks of various concentrations application (1 nmol/day, 10 nmol/day and 100 nmol/day, referred as 1×, 10× and 100× respectively). The healing was reflected as BV/TV in FIG. 6, TbTh in FIG. 7 and bone volume in FIG. 8, all in a dose dependent manner.

Example 4. OGP D10 Efficacy on Fracture Healing

Figure 9:
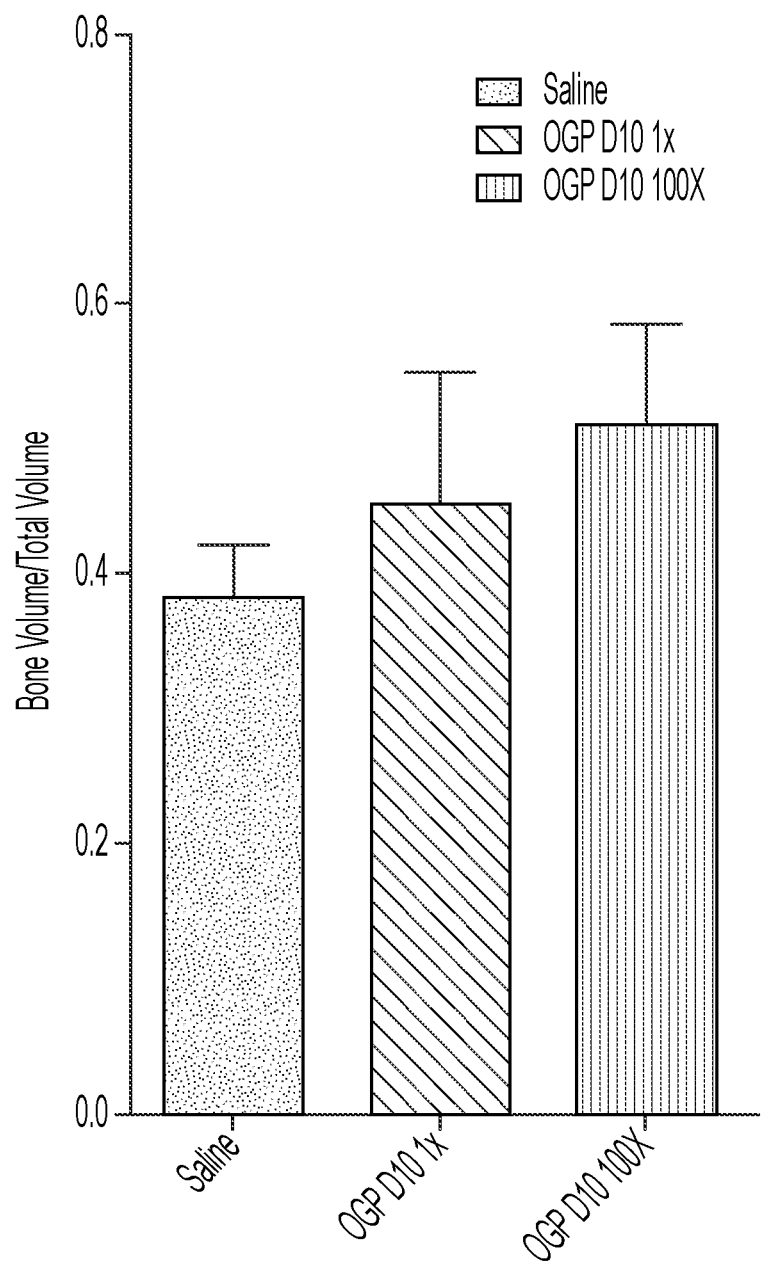
FIG. 9 depicts BV/TV two weeks after fractured femur received various concentration of OGP D10.
Figure 10:
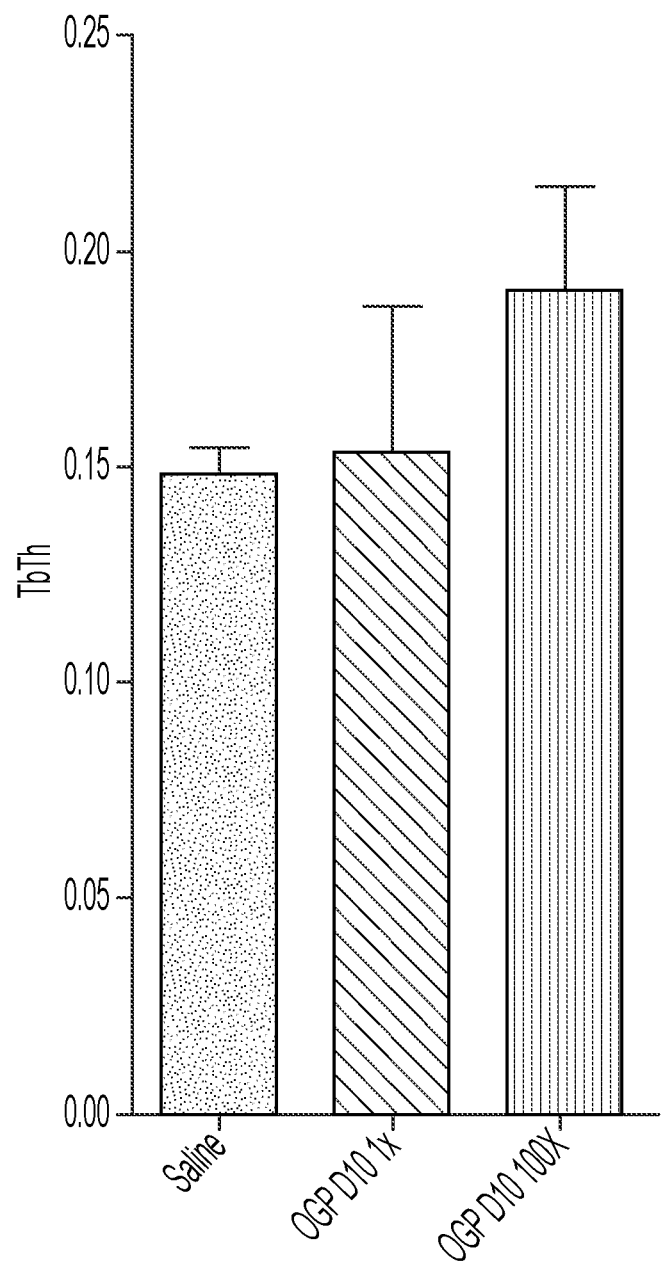
FIG. 10 depicts TbTh two weeks after fractured femur received various concentration of OGP D10.
Figure 11:
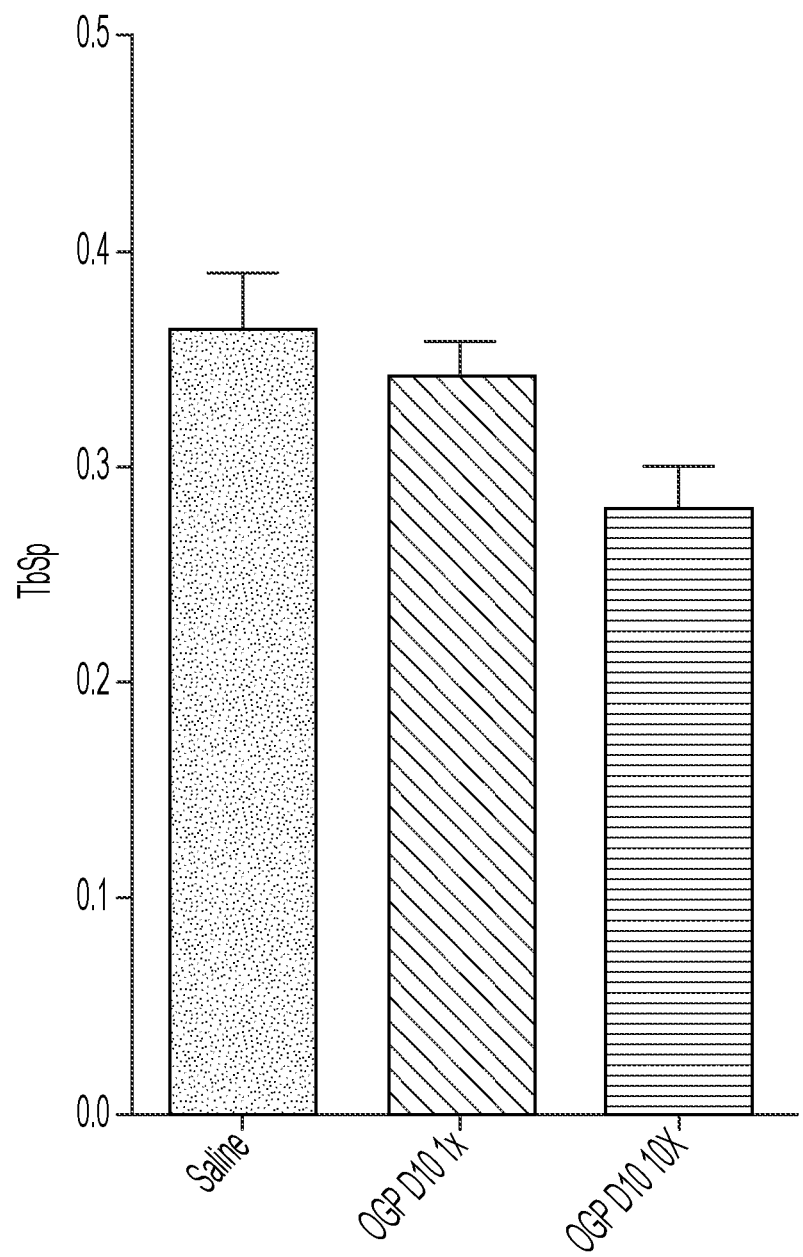
FIG. 11 depicts TbSp (the spacing between the trabecula in the 100 thickest micro CT slices of the fracture callus) two weeks after fractured femur received various concentration of OGP D10.

Example 4 indicates osteogenic growth peptide conjugate (OGP-D10) effect on healing fractured bone after 2 weeks of various concentrations application (1 nmol/day, and 100 nmol/day, referred as 1×, and 100× respectively). The healing was reflected as BV/TV in FIG. 9, TbTh in FIG. 10 and TbSp in FIG. 11, all in a dose dependent manner.

Example 5. BFP D10 Efficacy on Fracture Healing

Figure 12:
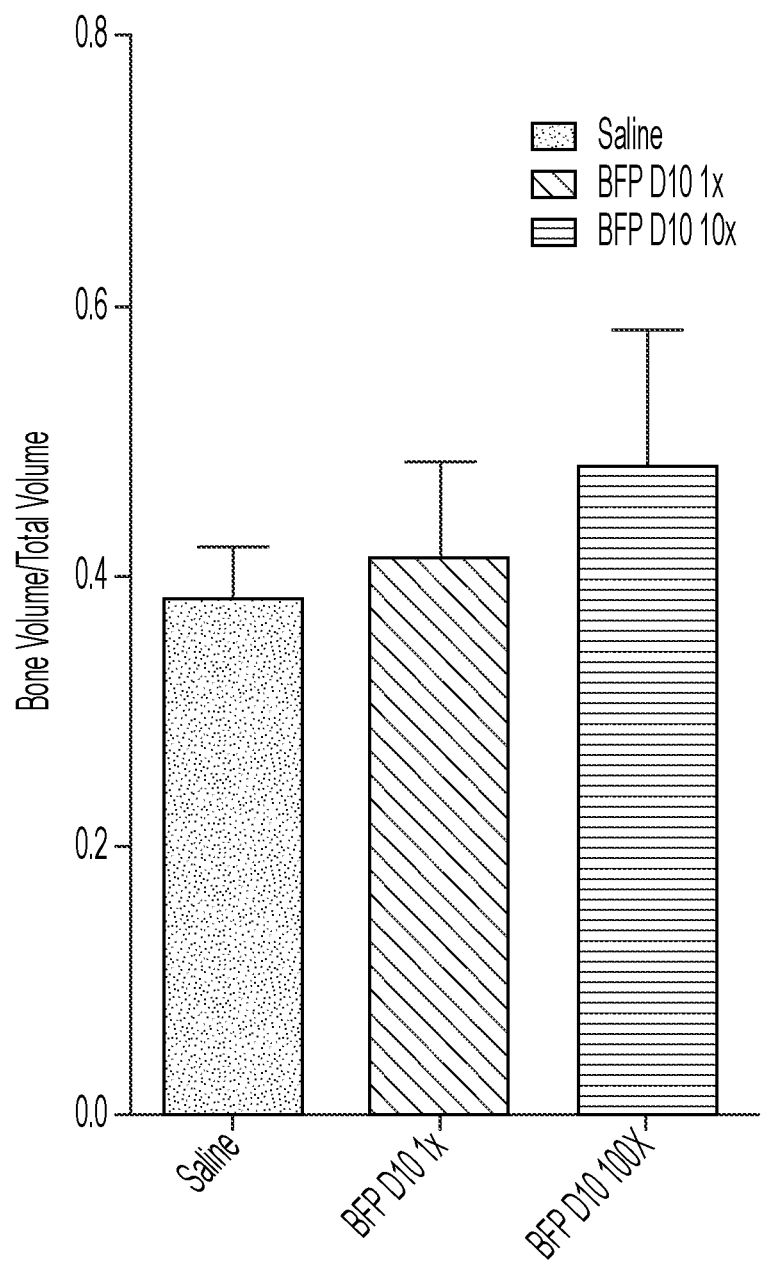
FIG. 12 depicts BV/TV two weeks after fractured femur received various concentration of BFPD10.
Figure 13:
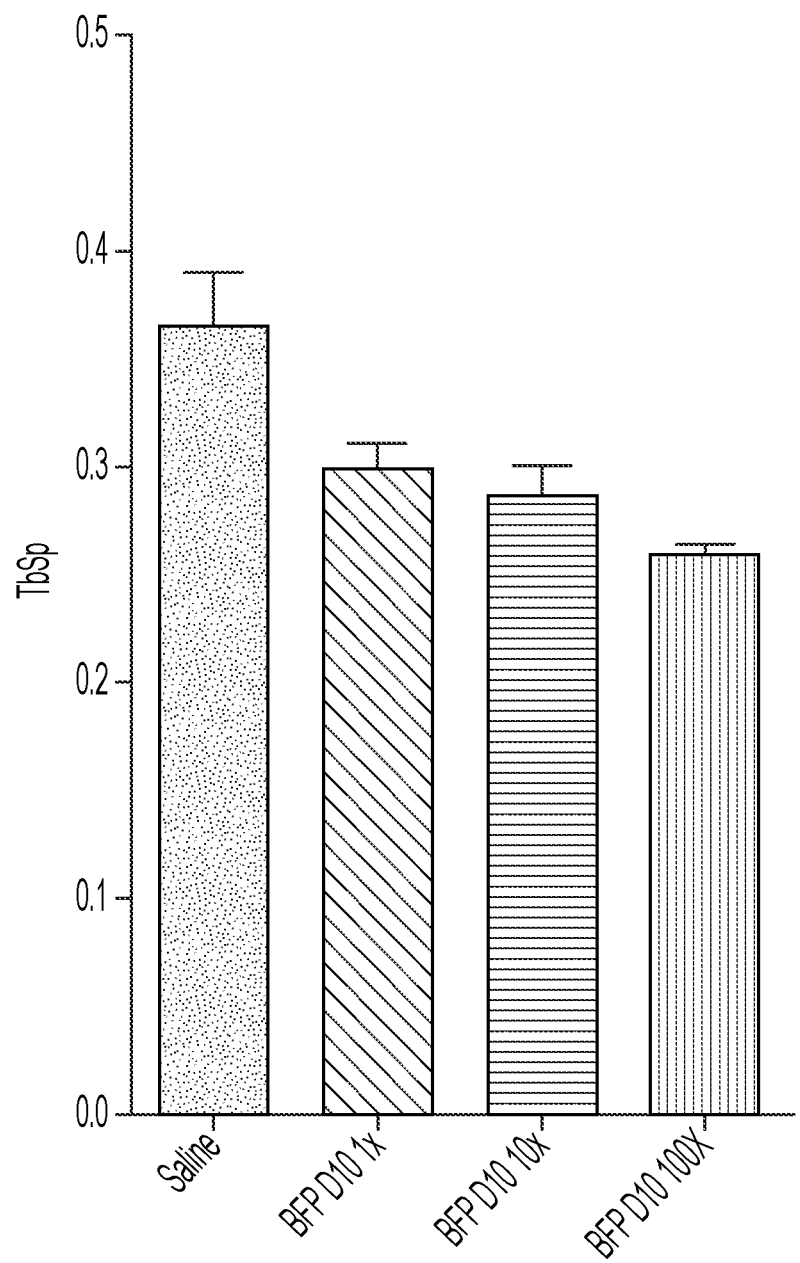
FIG. 13 depicts TbSp two weeks after fractured femur received various concentration of BFPD10.

Example 5 indicates bone forming peptide conjugate (BMP-D10) effect on healing fractured bone after 2 weeks of various concentrations application (1 nmol/day, 10 nmol/day and 100 nmol/day, referred as 1×, 10× and 100× respectively). The healing was reflected as BV/TV in FIG. 12, and TbSp in FIG. 13 in a dose dependent manner.

Example 6. Substance P D10 Effect on Fracture Healing

Figure 14A:
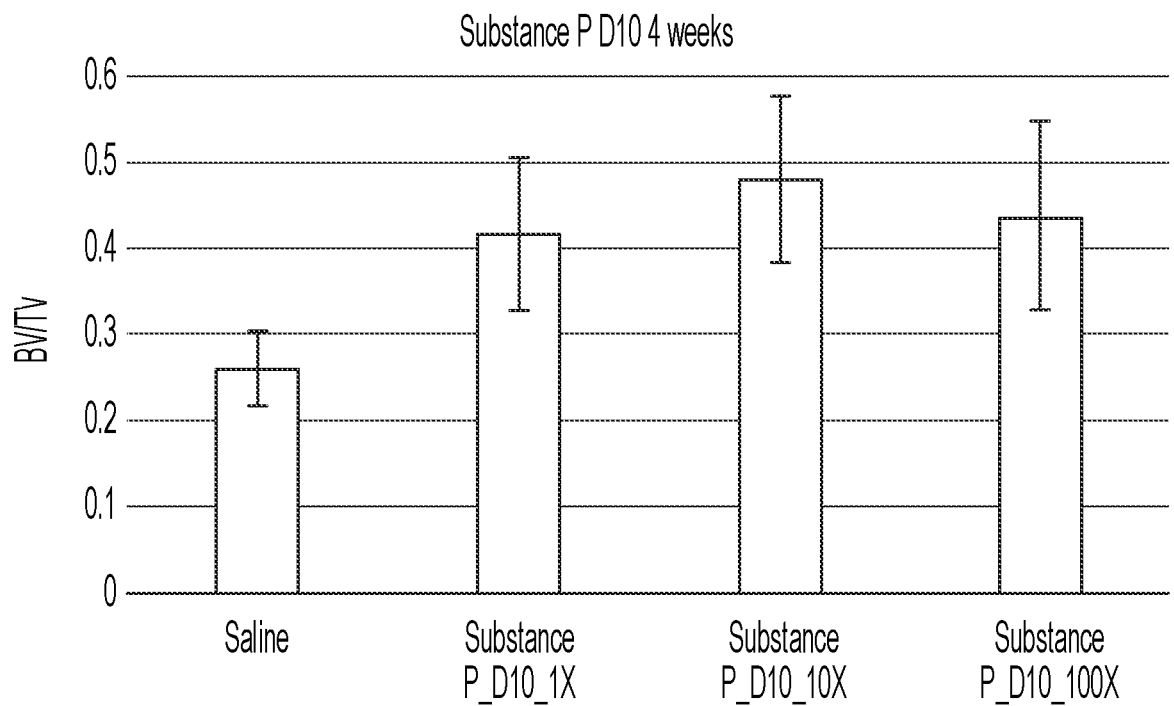
FIG. 14A depicts BV/TV four weeks after a fractured femur received various concentration of substance P4 mini peg D10 (P4 D10)
Figure 14B:
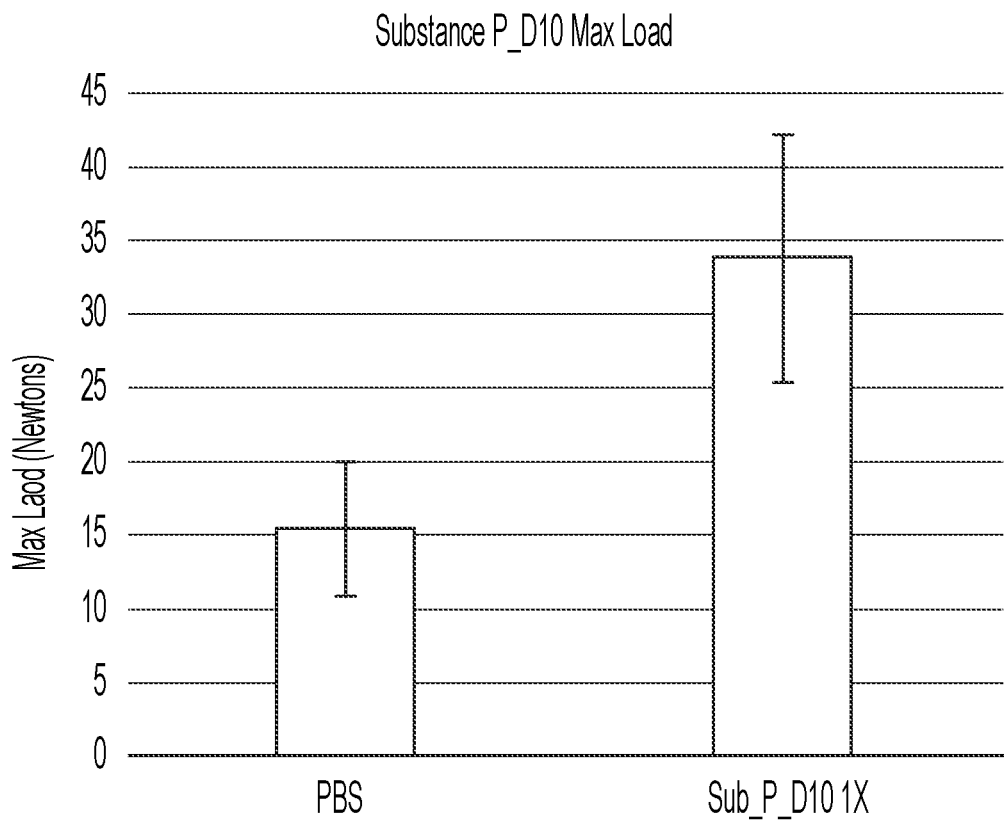
FIG. 14B depicts the max load of substance P4 D10 four weeks after a fractured femur received the max load of substance P4 D10.

Example 6 indicates substance P D10 conjugate effect on healing fractured bone after 4 weeks of various concentrations application (1 nmol/day, 10 nmol/day and 100 nmol/day, referred as 1×, 10× and 100× respectively). The healing was reflected as BV/TV in FIG. 14A in dose dependent manner. FIG. 14B indicates the peak load of substance P D10 10× induced healed femur can withstand between 30-35 Newtons force.

Example 7. Ghrelin-D10 Effect on Fracture Healing

Figure 15:
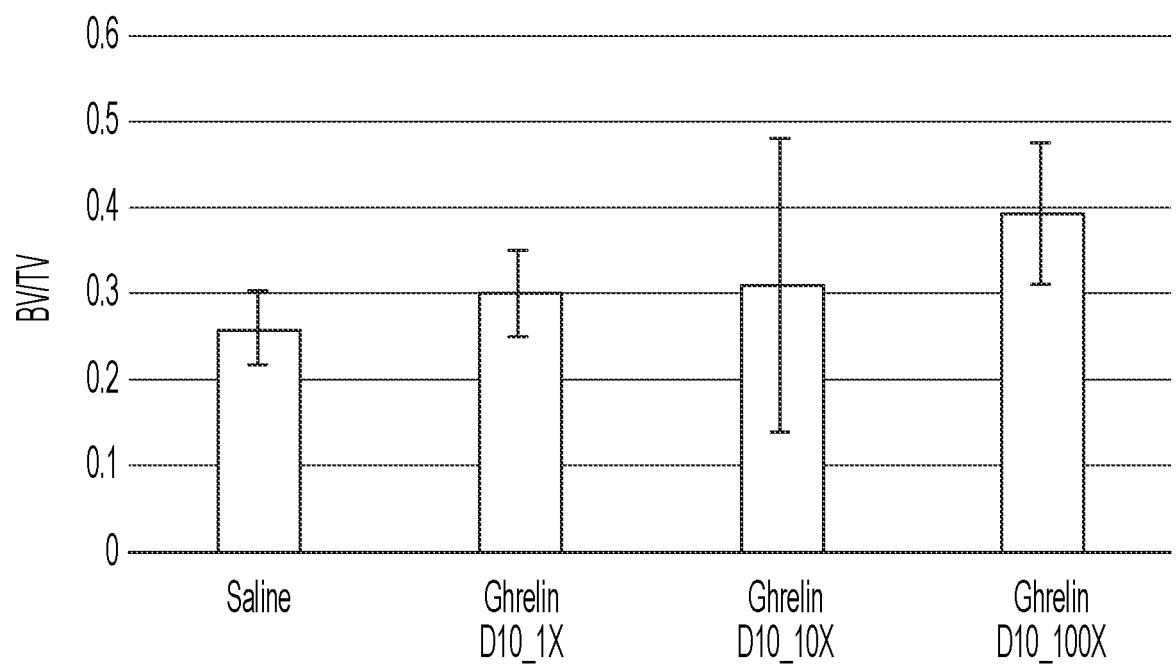
FIG. 15 depicts BV/TV four weeks after fractured femur received various concentration of Ghrelin D10.

Example 7 indicates Ghrelin-D 10 conjugate effect on healing fractured bone after 4 weeks of various concentrations application (nmol/day, 10 nmol/day and 100 nmol/day, referred as 1×, 10× and 100× respectively). The healing was reflected as BV/TV in FIG. 15 in dose dependent manner.

Example 8. pBMP9 D10 Effect on Fracture Healing

Figure 16:
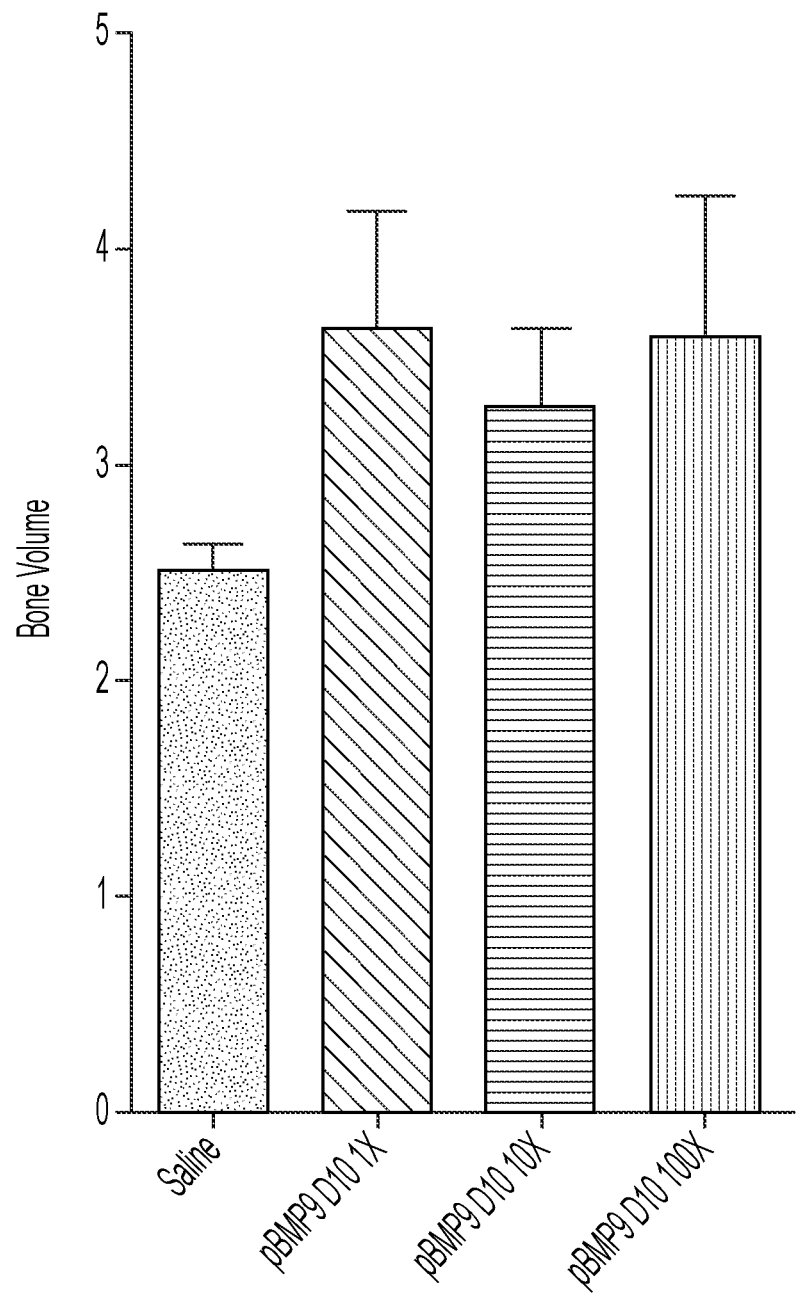
FIG. 16 depicts BV four weeks after fractured femur received various concentration of pBMP9 D10.
Figure 17:
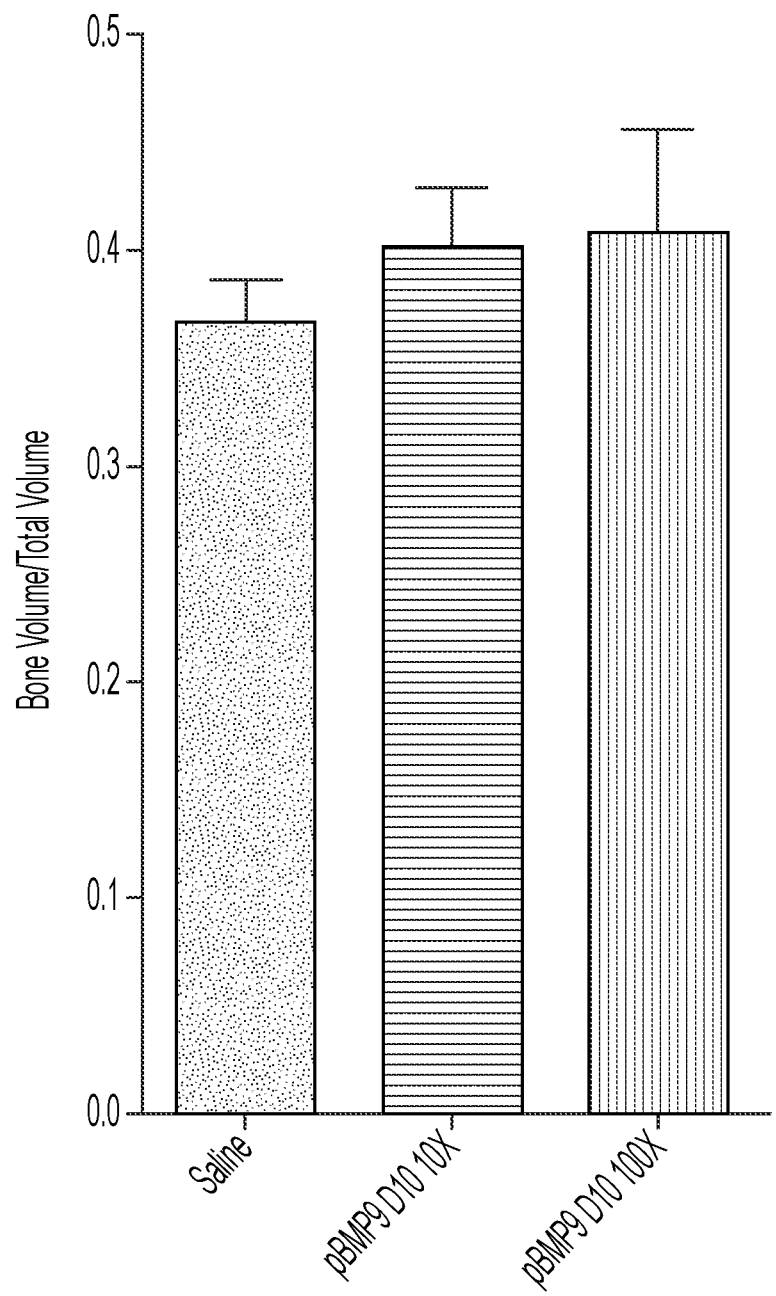
FIG. 17 depicts BV/TV four weeks after fractured femur received various concentration ofpBMP9 D10.

Example 8 indicates pBMP9 D 10 conjugate effect on healing fractured bone after 4 weeks of various concentrations application (1 nmol/day, 10 nmol/day and 100 nmol/day, referred as 1×, 10× and 100× respectively). The healing was reflected as bone volume in FIG. 16 and BV/TV in FIG. 17 in a dose dependent manner.

Example 9. CNP D10 Effect on Fracture Healing

Figure 18:
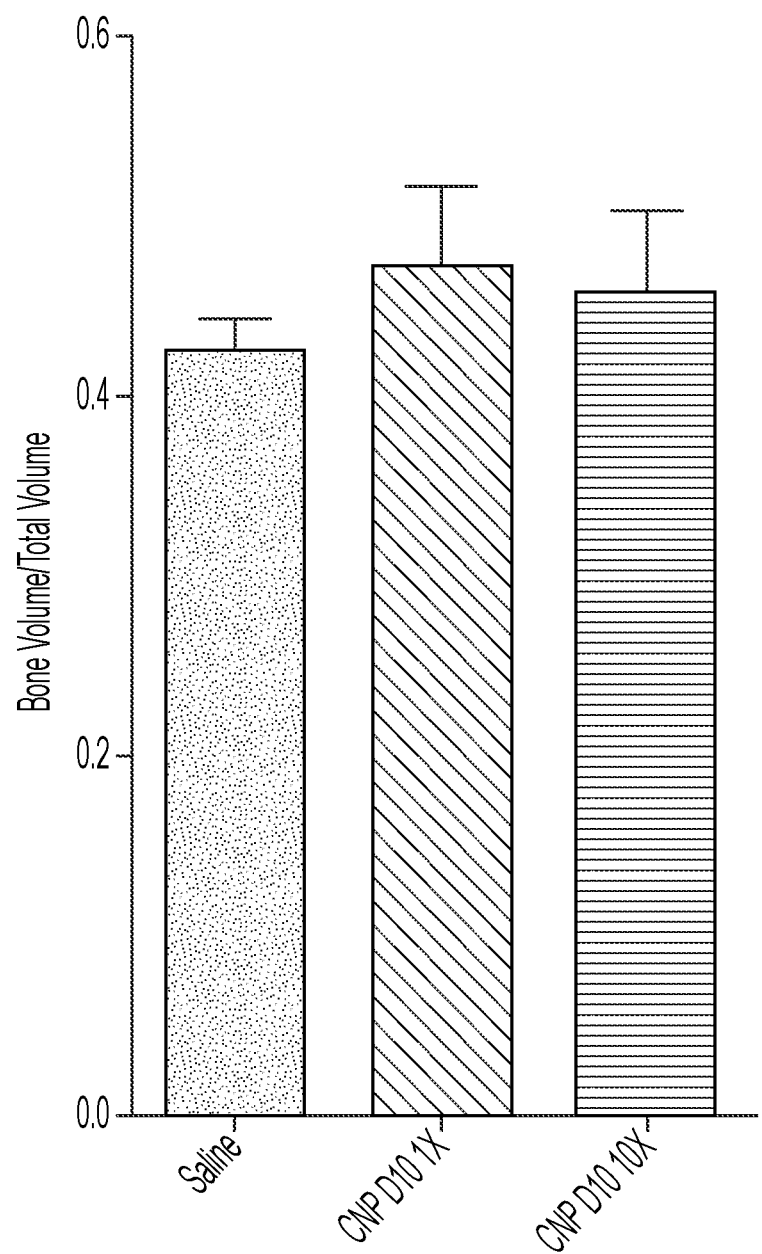
FIG. 18 depicts BV/TV four weeks after fractured femur received various concentration of CNPD10.

Example 9 indicates C-Type Natriuretic Peptide conjugate (CNP D10) effect on healing fractured bone after 4 weeks of various concentrations application (nmol/day and 10 nmol/day referred as 1× and 10× respectively). The healing was reflected as BV/TV in FIG. 18 in a dose dependent manner.

Example 10. ODP D10 Effect on Fracture Healing

Figure 19:
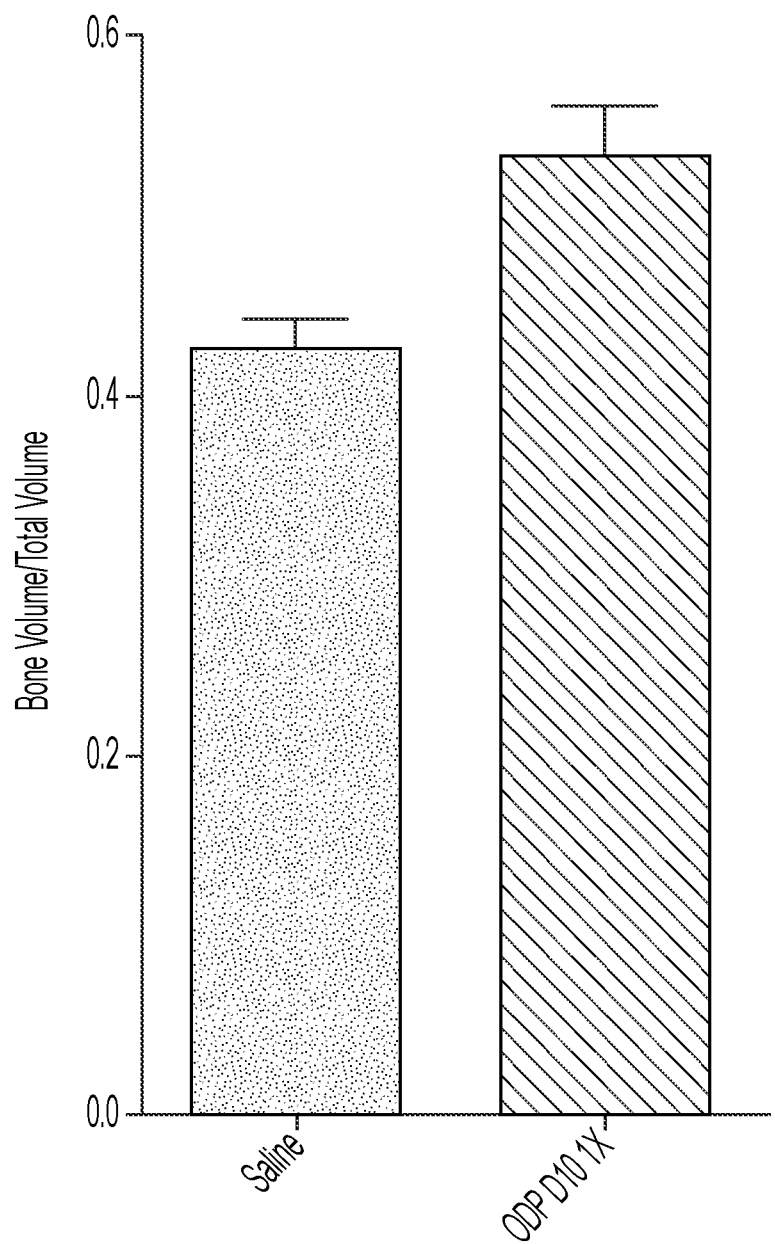
FIG. 19 depicts BV/TV four weeks after fractured femur received 1 nmol/day of ODP D10.

Example 10 indicates osteopontin derived peptide conjugate ODP D10 effect on healing fractured bone after 4 weeks of 1 nmol/day (referred as 1×). The healing was reflected as BV/TV in FIG. 19.

Example 11. CBM DI 0 Effect on Fracture Healing

Figure 20:
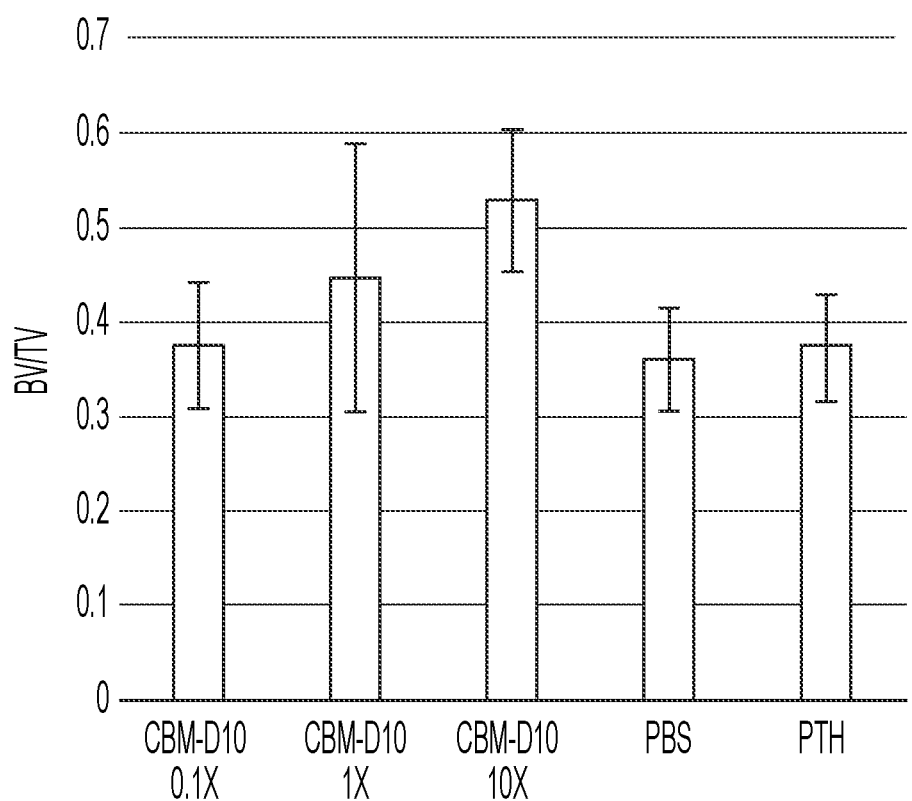
FIG. 20 depicts BV/TV three weeks after fractured femur received various concentrations of CBM D10 as compared to a fractured femur that received parathyroid hormone 1-34 (PTH).

Example 11 indicates collagen binding motif of osteopontin conjugate CBM D10 effect on healing fractured bone after 3 weeks of various concentrations application (0.1 nmol/day, 1 nmol/day and 10 nmol/day, referred as 0.1×, 1× and 10× respectively). The healing was reflected as BV/TV in FIG. 20 in a dose dependent manner. It is worth noting that the lowest does of CBM D10 has the similar effect of free PTH, an anabolic drug without specific bone targeting.

Example 12. P4 DI0 Effect on Fracture Healing

Example 12 indicates P4 D10 conjugate effect on healing fractured bone after 4 weeks of various concentrations application (nmol/day and 10 nmol/day, referred as 1× and 10× respectively).

Figure 21:
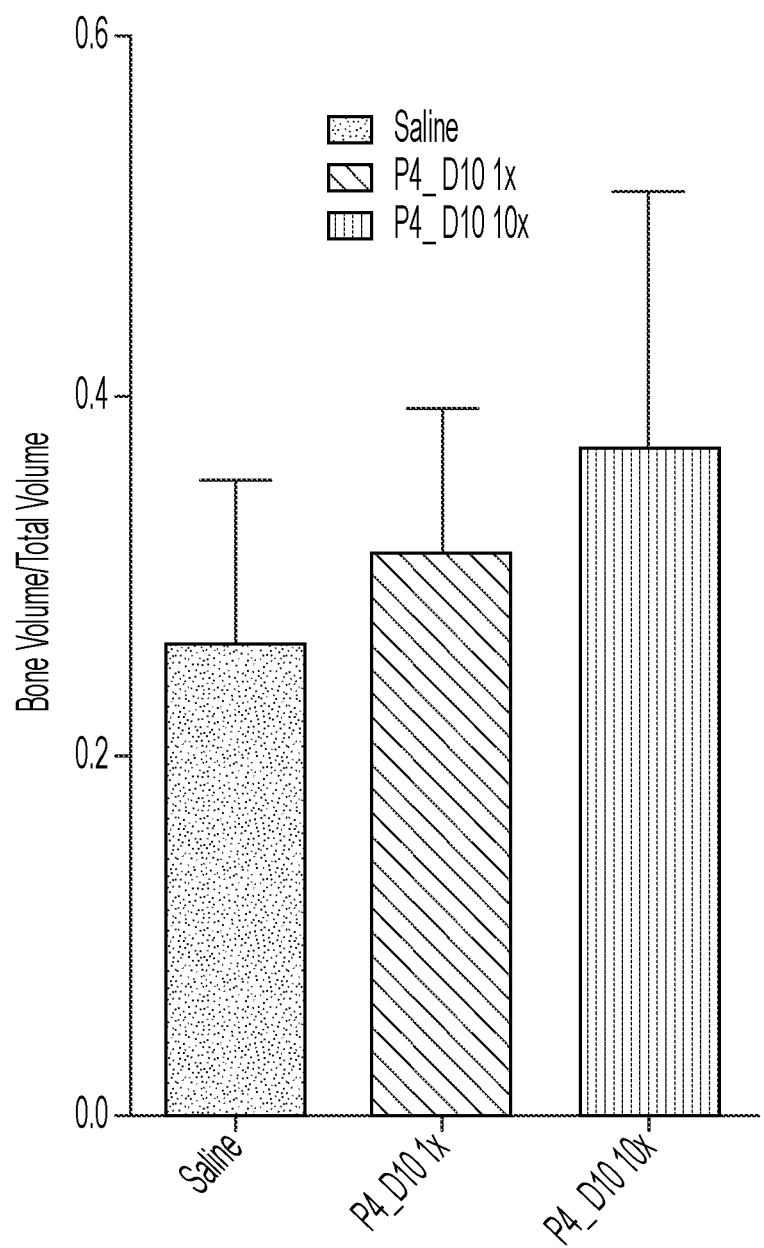
FIG. 21 depicts BV/TV four weeks after fractured femur received various concentrations of P4 D10.
Figure 22:
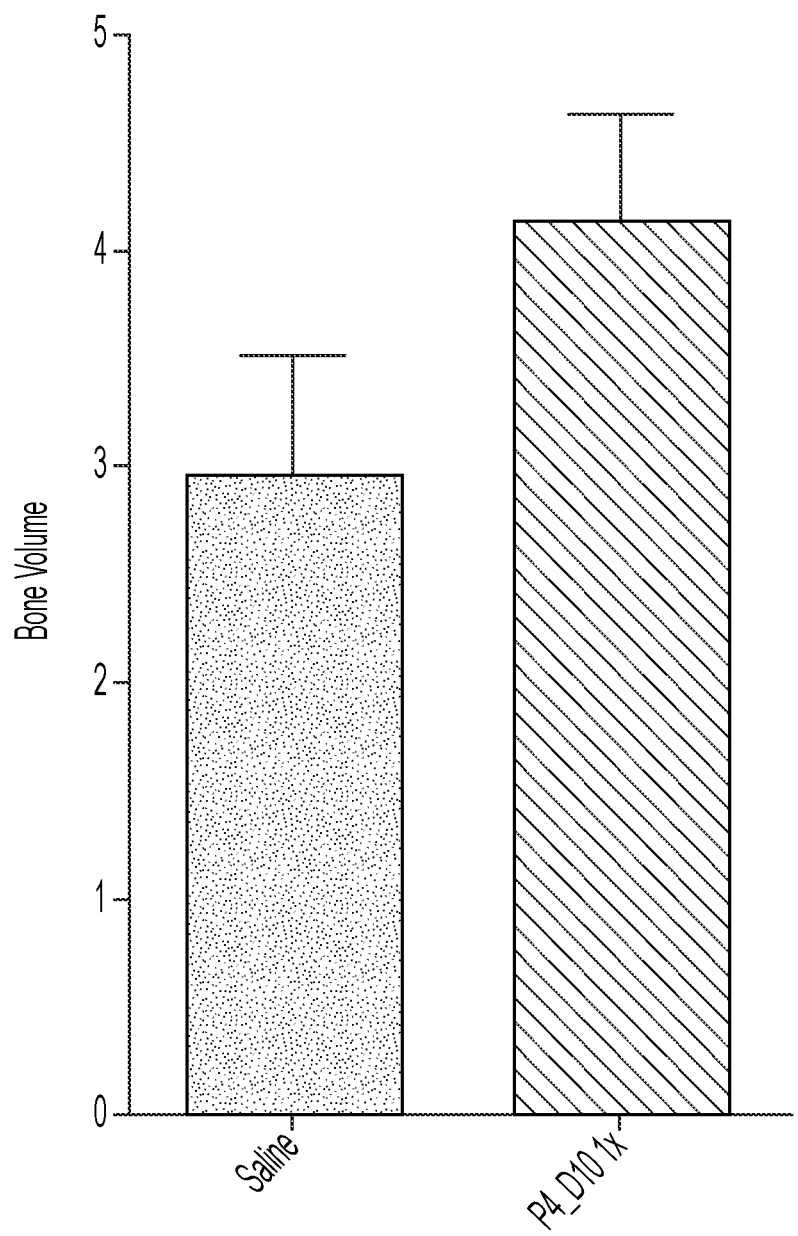
FIG. 22 depicts BV four weeks after fractured femur received 1 nmol/day of P4 D10.

The healing was reflected as BV/TV in FIG. 21 in a dose dependent manner and bone volume in FIG. 22.

Example 13. MGF DI 0 Effect on Fracture Healing

Figure 23:
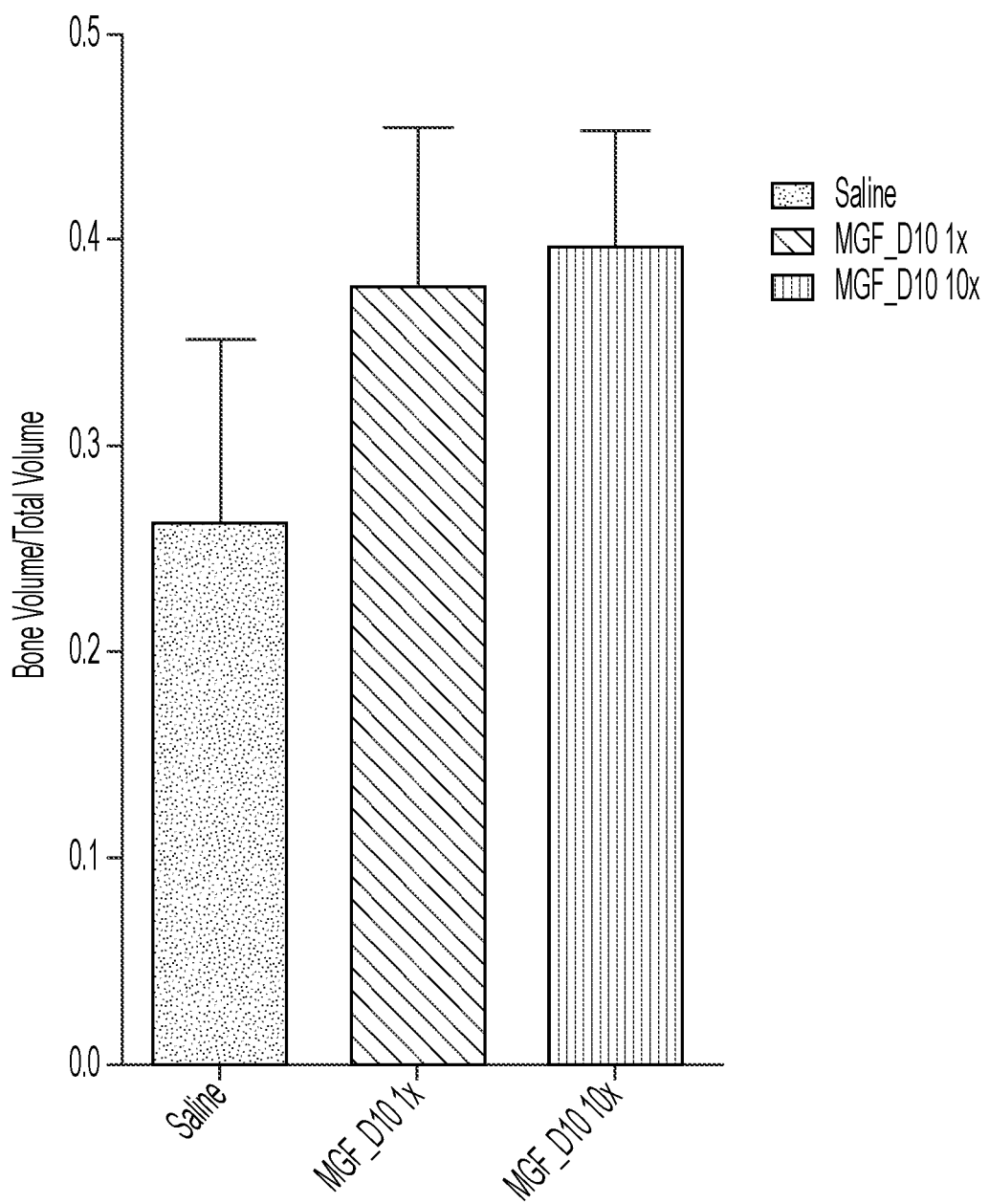
FIG. 23 depicts BV/TV four weeks after fractured femur received various concentrations of MGF D10.

Example 13 indicates mechano growth factor conjugate (MGF D10) effect on healing fractured bone after 4 weeks of various concentrations application (1 nmol/day and 10 nmol/day, referred as 1× and 10× respectively). The healing was reflected as BV/TV in FIG. 23 in a dose dependent manner.

Example 14. TP508 DI0 Effect on Fracture Healing

Figure 24:
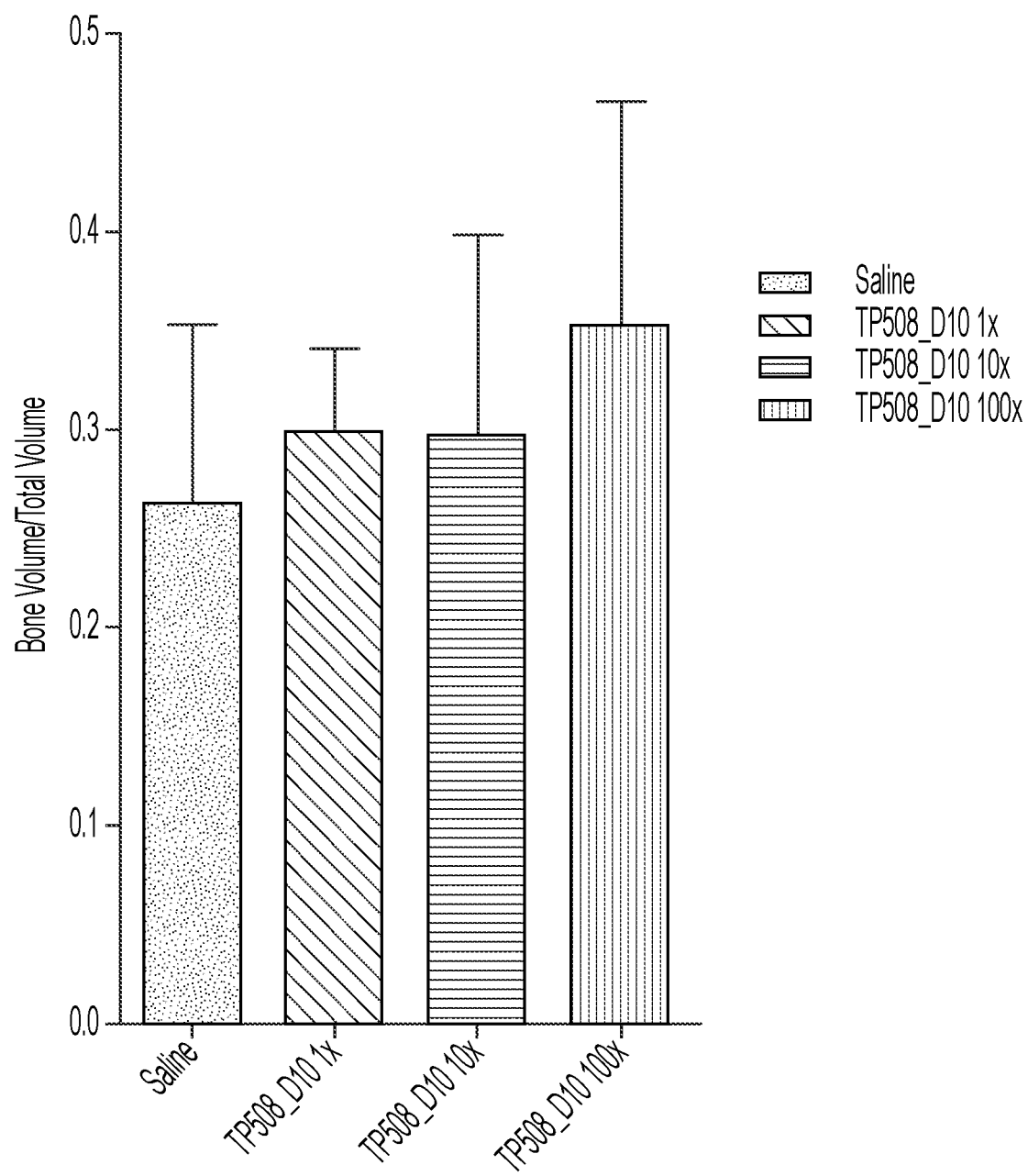
FIG. 24 depicts BV/TV four weeks after fractured femur received various concentrations of TP508 D10.

Example 14 indicates thrombin fragment TP508 conjugate TP508 D10 effect on healing fracture after 4 weeks of various concentrations application (1 nmol/day and 10 nmol/day, referred as 1× and 10× respectively). The healing was reflected as BV/TV in FIG. 24 in a dose dependent manner.

Example 15. VIP DIO Effect on Fracture Healing

Figure 25:
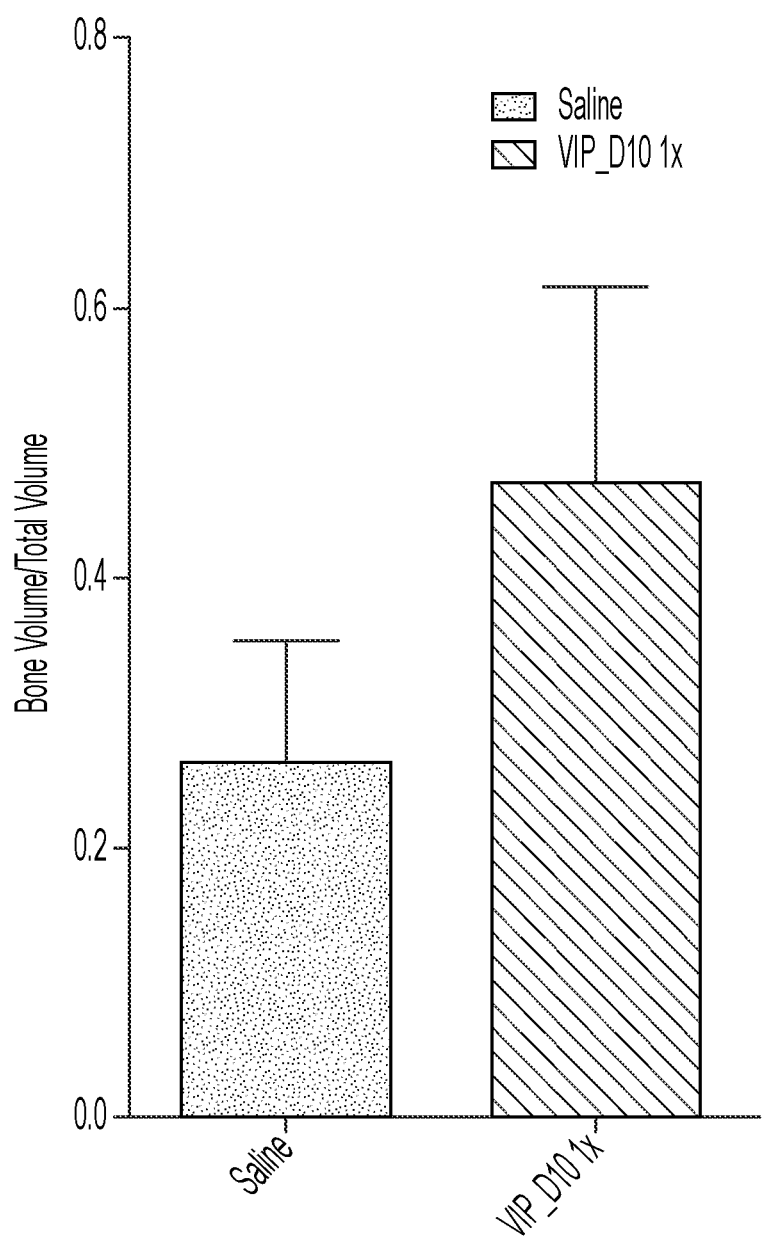
FIG. 25 depicts BV/TV four weeks after fractured femur received 1 nmol/day of VIP_D10.
Figure 26:
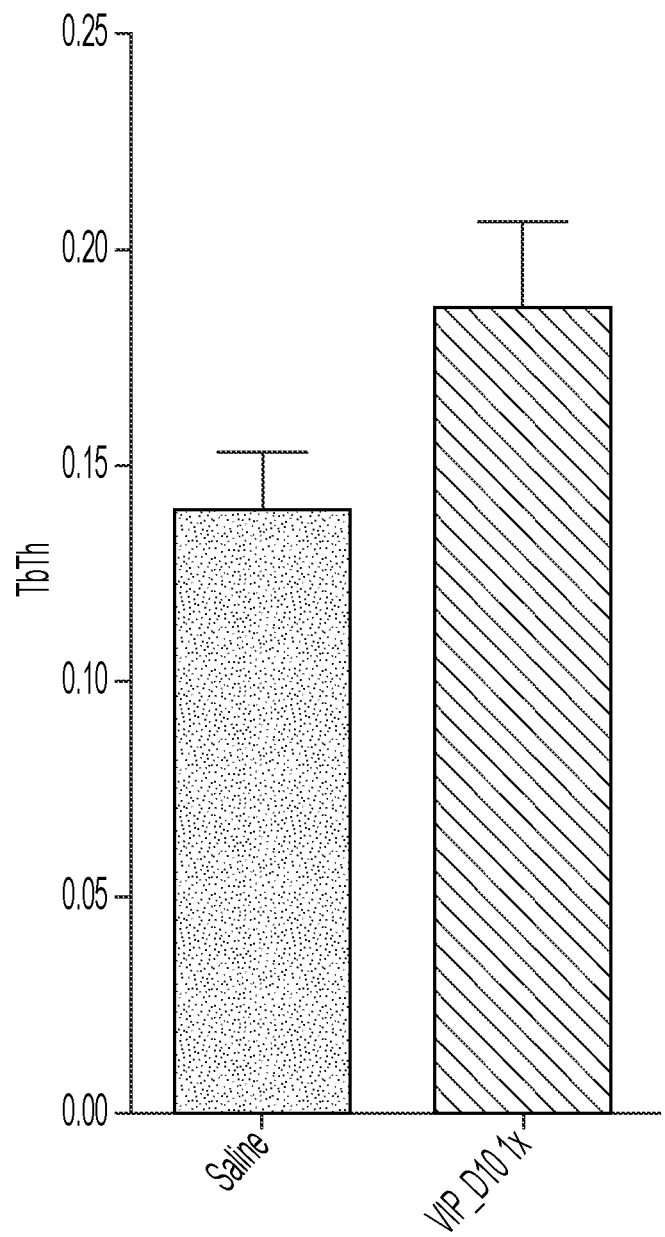
FIG. 26 depicts TbTh four weeks after fractured femur received 1 nmol/day of VIP_D10.

Example 15 indicates vasoactive intestinal peptide conjugate VIP D10 effect on healing fracture after 4 weeks of 1 nmol/day application (lx). The healing was reflected as BV/TV in FIG. 25 and TbTh in FIG. 26.

Example 16. B2A_AHX3_e10 Effect on Fracture Healing

Figure 36:
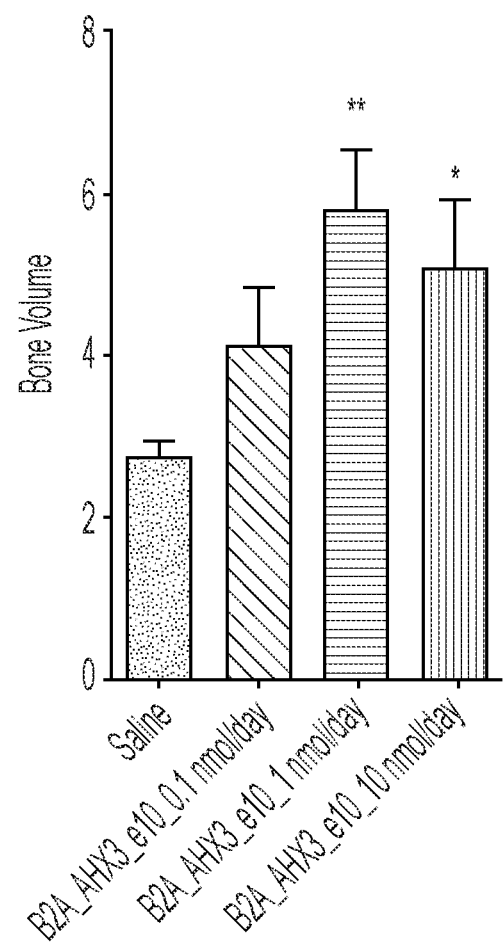
FIG. 36. Bone Volume measured after treatment with saline, or 0.1 nmol/day, 1 nmol/day or 10 nmol/day of B2A_AHX_e10.

Example 16 indicates B2A $(D)E_{10}$ effect on fracture healing. Referring now to FIG. 36, in vivo fracture healing efficacy of B2A_mp4_$(D)E_{10}$ conjugate on Swiss Webster fracture-bearing mice(n=5) after 3 weeks. BV represents the bone volume of the 100 thickest micro CT slices of the fracture callus and is a measure of how much bone has mineralized at the site of fracture repair. 0.1 nmol, 1 nmol, and 10 nmol of the conjugate were delivered daily by subcutaneous injection. B2A_mp4_$(D)E_{10}$ conjugate raises bone mineralization at the fracture calluses three weeks post fracture.

Figure 37:
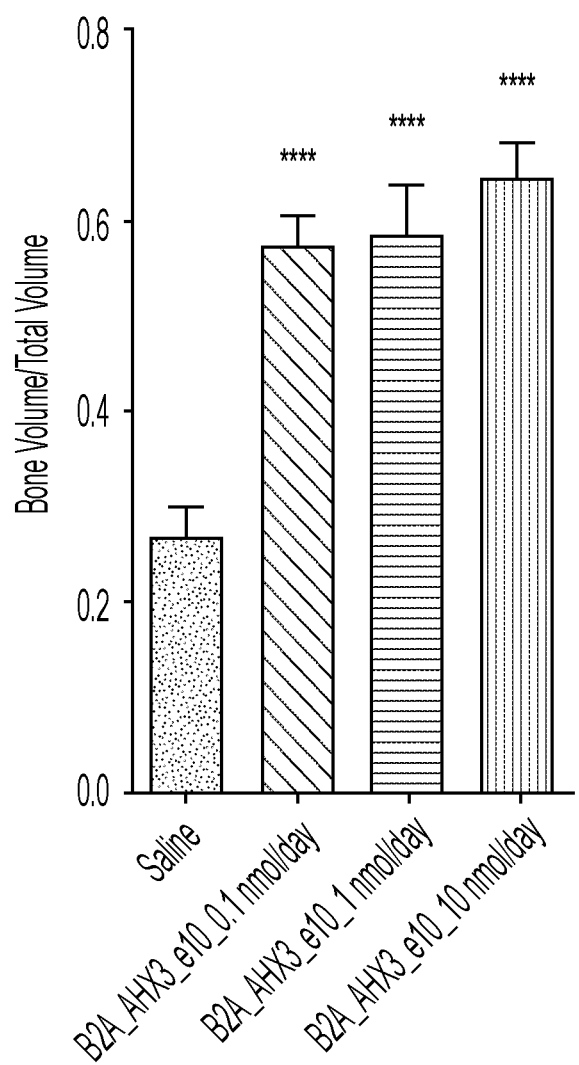
FIG. 37. Bone Volume/Total Volume measured after treatment with saline, or 0.1 nmol/day, 1 nmol/day or 10 nmol/day of B2A_AHX_e10.

Referring now to FIG. 37, in vivo fracture healing efficacy of B2A_mp4_$(D)E_{10}$ conjugate on Swiss Webster fracture-bearing mice(n=5) after 3 weeks. BY/TV-represents the bone volume divided by total volume of the 100 thickest micro CT slices of the fracture callus and is a measure of how dense the bone is at the site of fracture repair. 0.1 nmol, 1 nmol, and 10 nmol of the conjugate were delivered daily by subcutaneous injection. B2A_mp4_(D) $E_{10}$ conjugate raises bone density at the fracture calluses three weeks post fracture.

Figure 38:
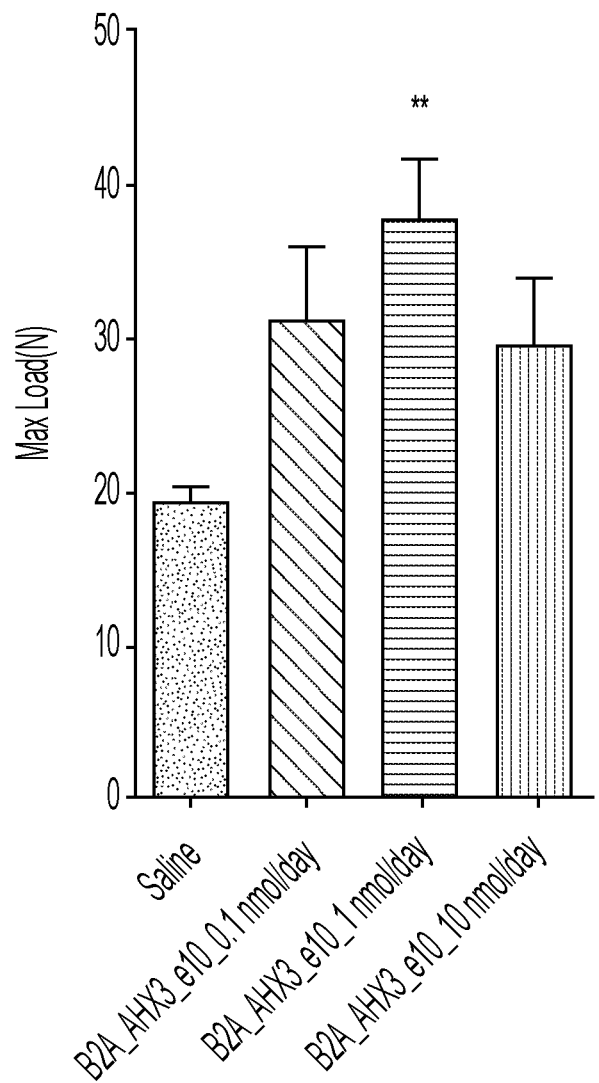
FIG. 38. Max Load (N) measured after treatment with saline, or 0.1 nmol/day, 1 nmol/day or 10 nmol/day of B2A_AHX_e10.

Referring now to FIG. 38, in vivo fracture healing efficacy of B2A_mp4_$(D)E_{10}$ conjugate on Swiss Webster fracture-bearing mice(n=5) after 3 weeks. Max load represents the maximum force the healed femur withstood before it refractured in a postmortem 4 point bend analysis. Peak load is a measure of how strong the bone is at the site of fracture repair. 0.1 nmol, 1 nmol, and 10 nmol of the conjugate were delivered daily by subcutaneous injection. B2A_mp4_(D) $E_{10}$ conjugate raises bone strength at the fracture calluses three weeks post fracture.

Referring now to FIG. 39, in vivo fracture healing efficacy of B2A_mp4_$(D)E_{10}$ conjugate on Swiss Webster fracture-bearing mice(n=5) after 3 weeks. Work to fracture represents the total amount of energy absorbed by the healed femur before it refractured in a postmortem 4 point bend analysis. Work to fracture is a measure of how strong the bone is at the site of fracture repair. 0.1 nmol, 1 nmol, and 10 nmol of the conjugate were delivered daily by subcutaneous injection. B2A_mp4_$(D)E_{10}$ conjugate raises bone strength at the fracture calluses three weeks post fracture.

Example 17. F2A_mp4-e 10 Effect on Fracture Healing

Figure 41:
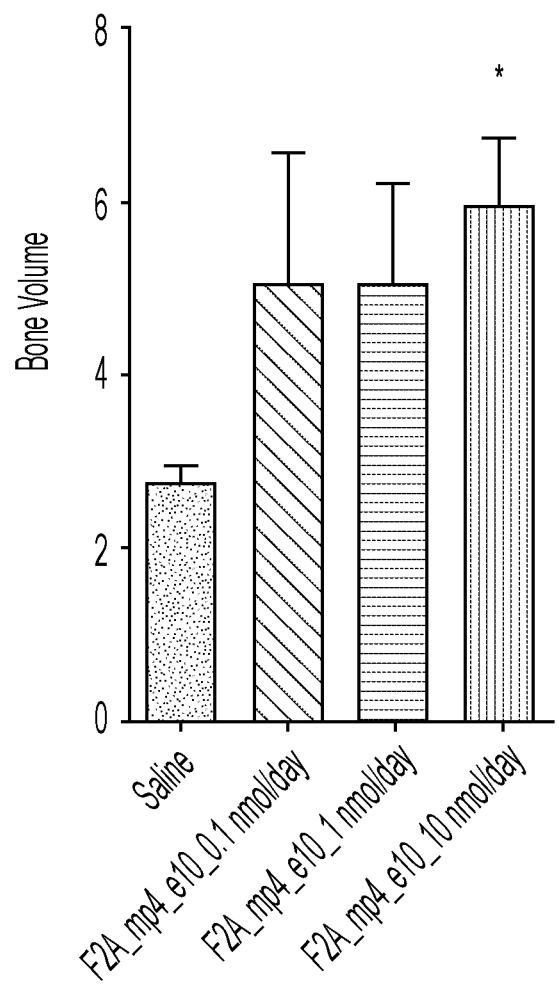
FIG. 41. Bone Volume measured after treatment with saline, or 0.1 nmol/day, 1 nmol/day or 10 nmol/day of F2A_mp4_e10.

Example 17 indicates F2A $(D)E_{10}$ effect on fracture healing. Referring now to FIG. 41, in vivo fracture healing efficacy of F2A_mp4_$(D)E_{10}$ conjugate on Swiss Webster fracture-bearing mice(n=5) after 3 weeks. BV represents the bone volume of the 100 thickest micro CT slices of the fracture callus and is a measure of how much bone has mineralized at the site of fracture repair. 0.1 nmol, 1 nmol, and 10 nmol of the conjugate were delivered daily by subcutaneous injection. F2A_mp4_$(D)E_{10}$ conjugate raises bone mineralization at the fracture calluses three weeks post fracture.

Figure 42:
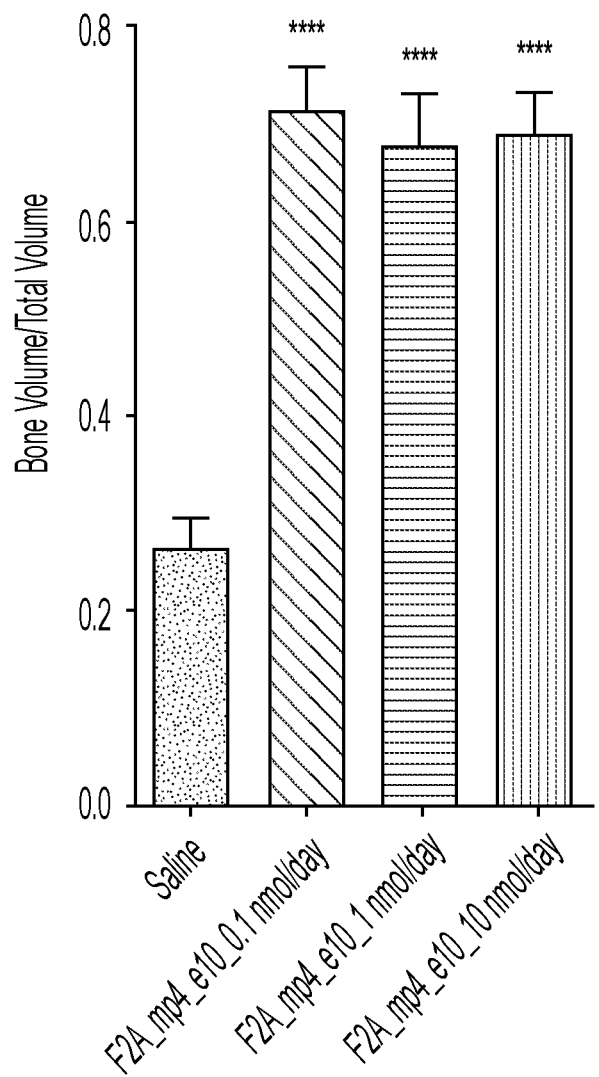
FIG. 42. Bone Volume/Total Volume measured after treatment with saline, or 0.1 nmol/day, 1 nmol/day or 10 nmol/day of F2A_mp4_e10.

Referring now to FIG. 42, in vivo fracture healing efficacy of F2A_mp4_$(D)E_{10}$ conjugate on Swiss Webster fracture-bearing mice(n=5) after 3 weeks. BY/TV-represents the bone volume divided by total volume of the 100 thickest micro CT slices of the fracture callus and is a measure of how dense the bone is at the site of fracture repair. 0.1 nmol, I nmol, and 10 nmol of the conjugate were delivered daily by subcutaneous injection. F2A mp4_(D) $E_{10}$ conjugate raises bone density at the fracture calluses three weeks post fracture.

Figure 43:
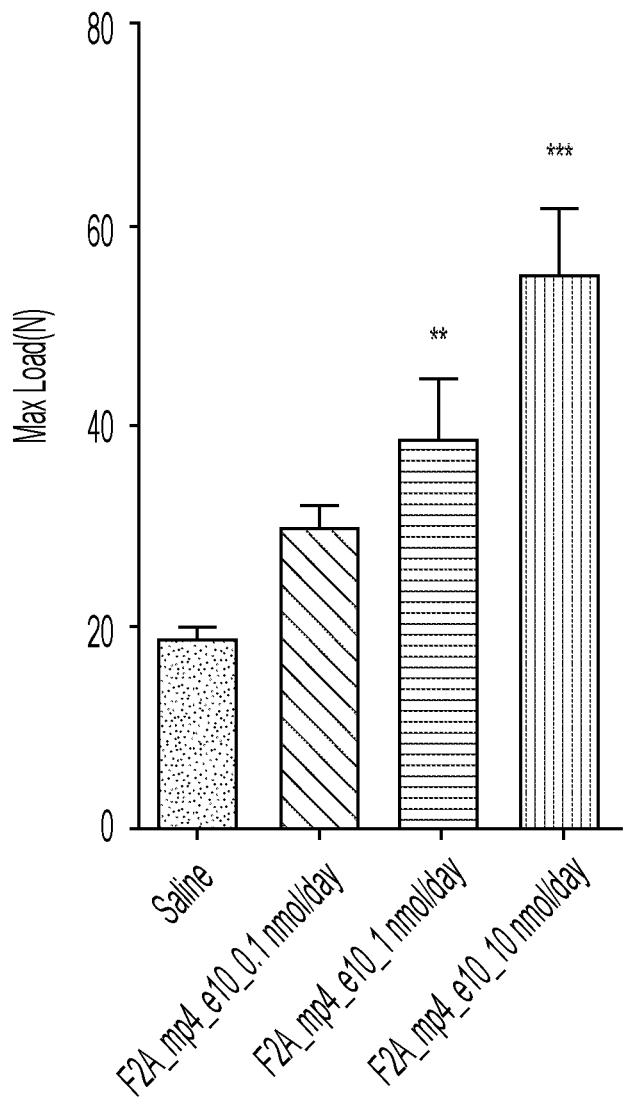
FIG. 43. Max Load (N) measured after treatment with saline, or 0.1 nmol/day, 1 nmol/day or 10 nmol/day of F2A_mp4e10.

Referring now to FIG. 43, in vivo fracture healing efficacy of F2A_mp4_$(D)E_{10}$ conjugate on Swiss Webster fracture-bearing mice(n=5) after 3 weeks. Max load represents the maximum force the healed femur withstood before it refractured in a postmortem 4 point bend analysis. Peak load is a measure of how strong the bone is at the site of fracture repair. 0.1 nmol, 1 nmol, and 10 nmol of the conjugate were delivered daily by subcutaneous injection. F2A_mp4 $(D)E_{10}$ conjugate raises bone strength at the fracture calluses three weeks post fracture.

Figure 44:
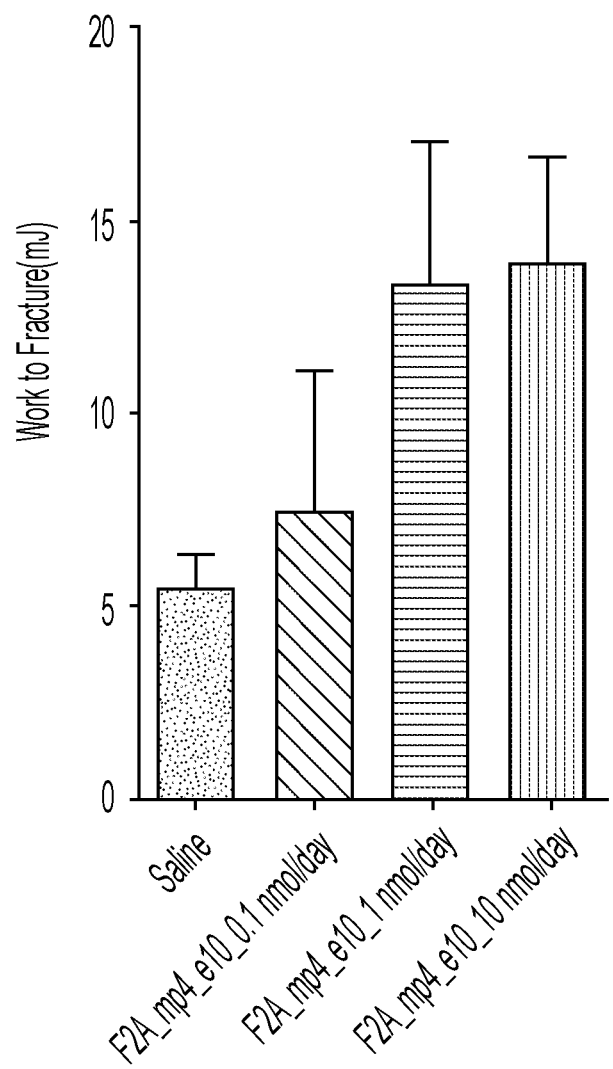
FIG. 44. Work to Fracture (mJ) measured after treatment with saline, or 0.1 nmol/day, 1 nmol/day or 10 nmol/day of F2A_mp4_e10.

Referring now to FIG. 44, in vivo fracture healing efficacy of F2A_mp4_$(D)E_{10}$ conjugate on Swiss Webster fracture-bearing mice(n=5) after 3 weeks. Work to fracture represents the total amount of energy absorbed by the healed femur before it refractured in a postmortem 4 point bend analysis. Work to fracture is a measure of how strong the bone is at the site of fracture repair. 0.1 nmol, 1 nmol, and 10 nmol of the conjugate were delivered daily by subcutaneous injection. F2A mp4 $(D)E_{10}$ conjugate raises bone strength at the fracture calluses three weeks post fracture.

Example 18. Fl 19: Effect on Fracture Healing

Figure 45:
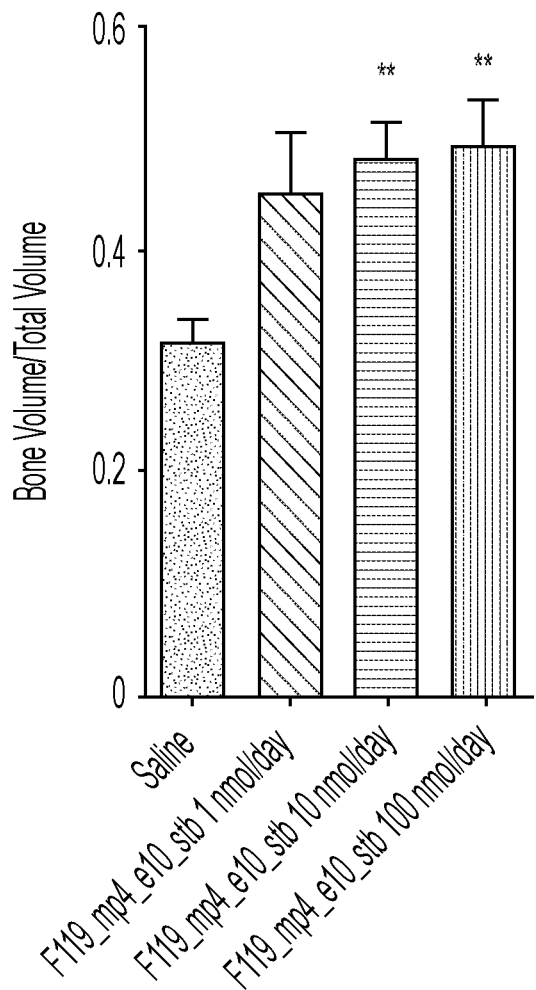
FIG. 45. Bone Volume/Total Volume measured after treatment with saline, or 0.1 nmol/day, 1 nmol/day or 10 nmol/day of F119_mp4_e10_stb.

Example 18 indicates F119 effect on fracture healing. Referring now to FIG. 45, in vivo fracture healing efficacy of F119_mp4 $(D)E_{10}$ conjugate on Swiss Webster fracture-bearing mice (n=5) after 3 weeks is reflected as BV/TV. BV/TV represents the bone volume of the total volume of 100 thickest micro CT slices of the fracture callus and is a measure of bone density at the site of fracture repair. 1×, 10× and 100× are respectively 1 nmol, 10 nmol, and 100 nmol of the conjugate delivered daily by subcutaneous injection. F119_mp4 $(D)E_{10}$ conjugate raises bone density at the fracture calluses three weeks post fracture.

Figure 46:
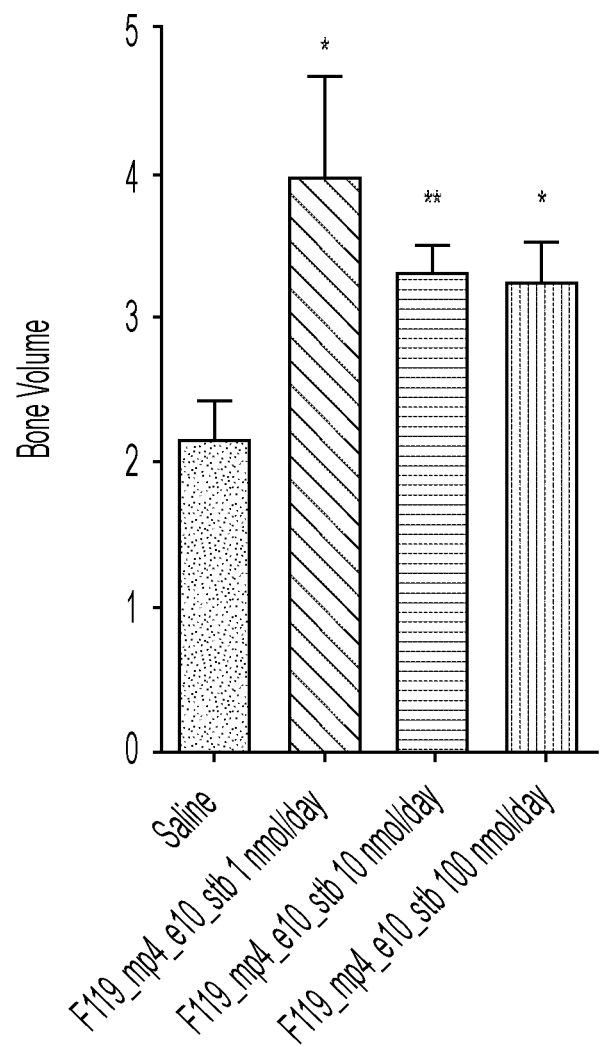
FIG. 46. Bone Volume measured after treatment with saline, or 0.1 nmol/day, 1 nmol/day or 10 nmol/day of F119_mp4_e10_stb.

Referring now to FIG. 46, in vivo fracture healing efficacy of F119_mp4_$(D)E_{10}$ conjugate on Swiss Webster fracture-bearing mice (n=5) after 3 weeks is reflected as By. BV represents the bone volume of the I 00 thickest micro CT slices of the fracture callus and is a measure of how much bone has mineralized at the site of fracture repair. 1×, 10× and 100× are respectively 1 nmol, 10 nmol, and 100 nmol of the conjugate delivered daily by subcutaneous injection. F119_mp4 $(D)E_{10}$ conjugate raises bone mineralization at the fracture calluses three weeks post fracture.

Figure 47:
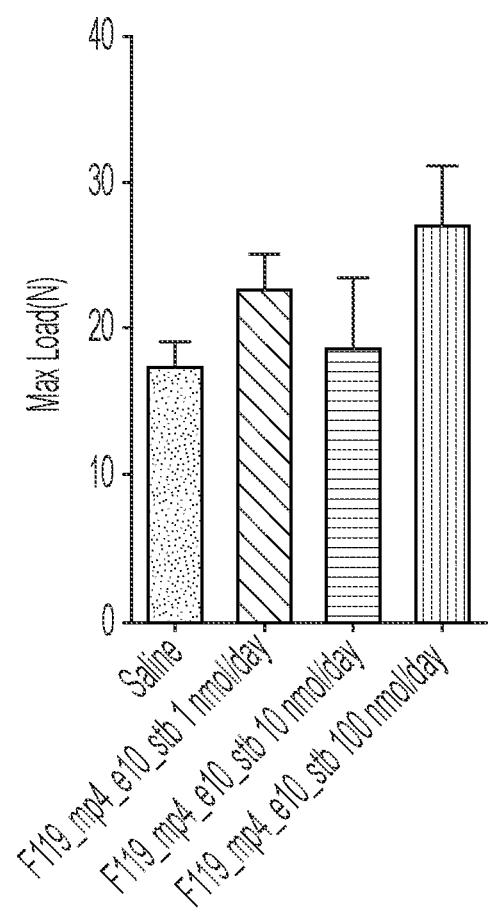
FIG. 47. Max Load (N) measured after treatment with saline, or 0.1 nmol/day, 1 nmol/day or 10 nmol/day of F119_mp4_e10_stb.

Referring now to FIG. 47, in vivo fracture healing efficacy of F119_mp4 $(D)E_{10}$ conjugate on Swiss Webster fracture-bearing mice (n=5) after 3 weeks is reflected as max load. Max load represents the maximum force the healed femur withstood before it refractured in a postmortem 4 point bend analysis. Peak load is a measure of how strong the bone is at the site of fracture repair. 1 nmol, 10 nmol, and 100 nmol of the conjugate were delivered daily by subcutaneous injection. F119_mp4 $(D)E_{10}$ conjugate raises bone strength at the fracture calluses three weeks post fracture.

Figure 48:
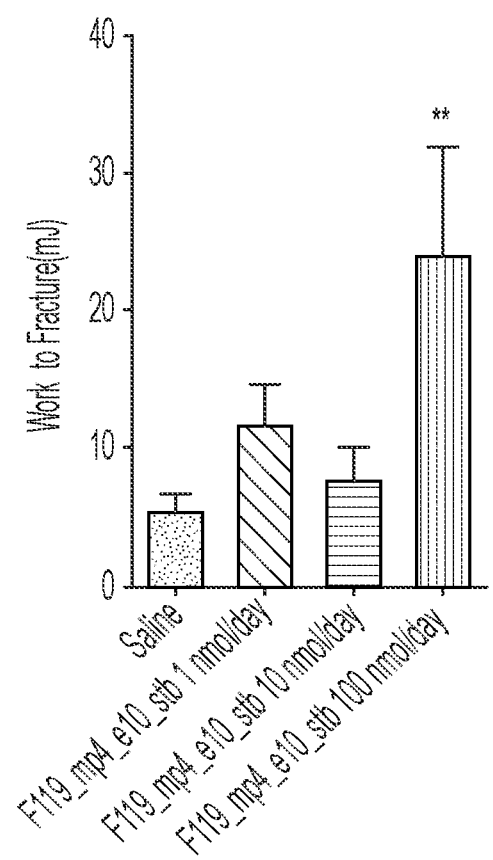
FIG. 48. Work to Fracture (mJ) measured after treatment with saline, or 0.1 nmol/day, 1 nmol/day or 10 nmol/day of F119_mp4_e10_stb.

Referring now to FIG. 48, in vivo fracture healing efficacy of F119_mp4 (D)$E_{10}$ conjugate on Swiss Webster fracture-bearing mice (n=5) after 3 weeks is reflected as work to fracture. Work to fracture represents the total amount of energy absorbed by the healed femur before it refractured in a postmortem 4 point bend analysis. Work to fracture is a measure of how strong the bone is at the site of fracture repair. 1 nmol, 10 nmol, and 100 nmol of the conjugate were delivered daily by subcutaneous injection. F119_mp4 (D)$E_{10}$ conjugate raises bone strength at the fracture calluses three weeks post fracture.

Example 19. JNK3_Mp4_e10 Effect on Fracture Healing

Figure 50:
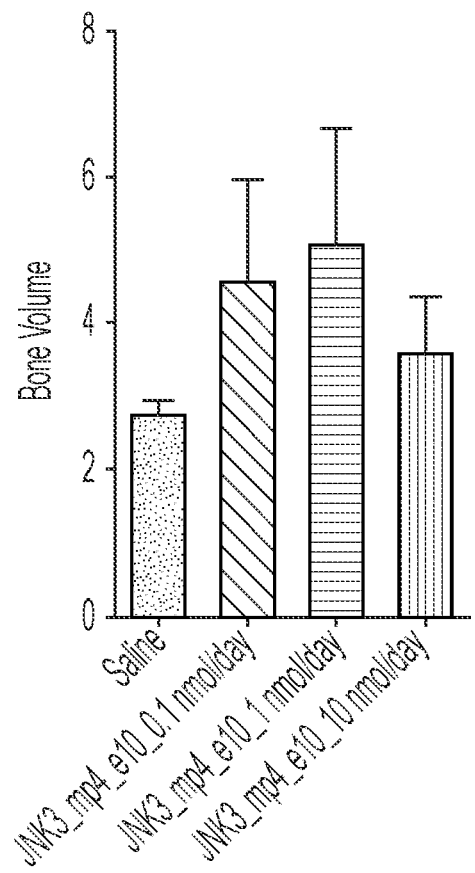
FIG. 50. Bone Volume measured after treatment with saline, or 0.1 nmol/day, 1 nmol/day or 10 nmol/day of JNK3_mp4_e10.

Example 19 indicates JNK3 effect on fracture healing. Referring now to FIG. 50, in vivo fracture healing efficacy of JNK3_Mp4_(D)$E_{10}$ conjugate on Swiss Webster fracture-bearing mice (n=5) after 3 weeks is reflected as By. BV represents the bone volume of the 100 thickest micro CT slices of the fracture callus and is a measure of how much bone has mineralized at the site of fracture repair. 0.1 nmol, 1 nmol, and 10 nmol of the conjugate were delivered daily by subcutaneous injection. JNK3_Mp4_(D)$E_{10}$ conjugate raises bone mineralization at the fracture calluses three weeks post fracture.

Figure 51:
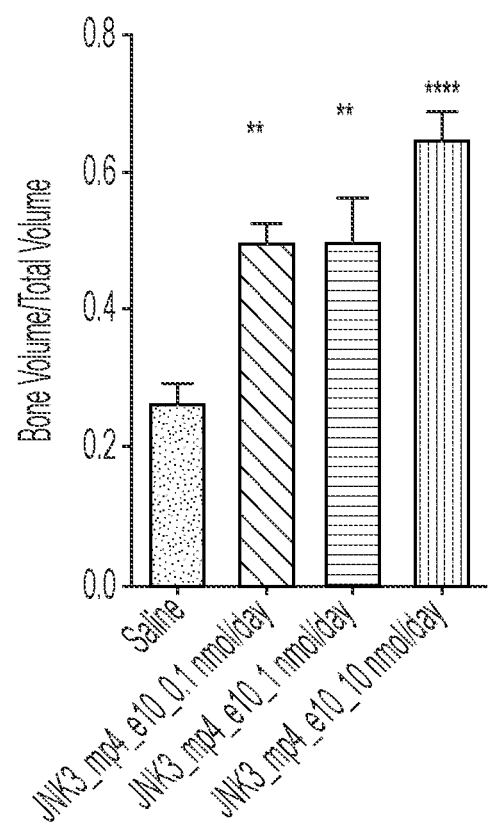
FIG. 51. Bone Volume/Total Volume measured after treatment with saline, or 0.1 nmol/day, 1 nmol/day or 10 nmol/day of JNK3_mp4_e10.

Referring now to FIG. 51, in vivo fracture healing efficacy of JNK3_Mp4_(D)$E_{10}$ conjugate on Swiss Webster fracture-bearing mice (n=5) after 3 weeks is reflected as BV/TV. BV/TV represents the bone volume divided by total volume of the 100 thickest micro CT slices of the fracture callus and is a measure of how dense the bone is at the site of fracture repair. 0.1 nmol, 1 nmol, and 10 nmol of the conjugate were delivered daily by subcutaneous injection. JNK3_Mp4_(D)$E_{10}$ conjugate raises bone density at the fracture calluses three weeks post fracture.

Figure 52:
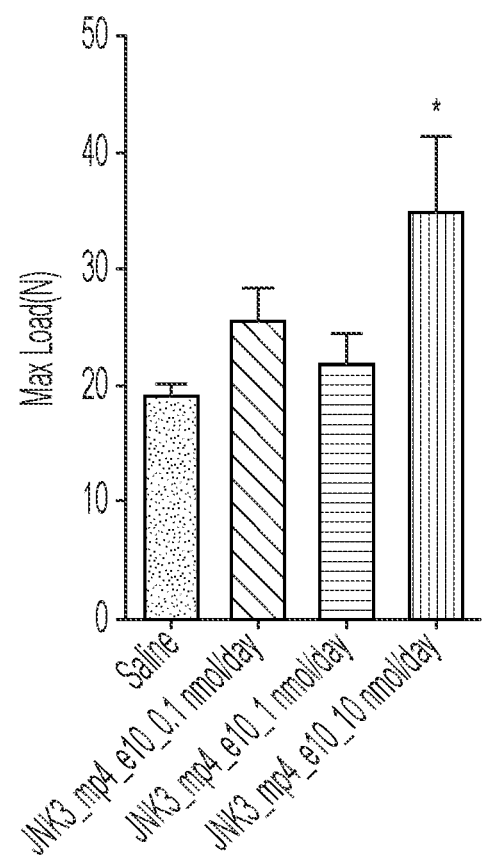
FIG. 52. Max Load (N) measured after treatment with saline, or 0.1 nmol/day, 1 nmol/day or 10 nmol/day of JNK3_mp4_e10.

Referring now to FIG. 52, in vivo fracture healing efficacy of JNK3_Mp4_(D)$E_{10}$ conjugate on Swiss Webster fracture-bearing mice (n=5) after 3 weeks is reflected as max load. Max load represents the maximum force the healed femur withstood before it refractured in a postmortem 4 point bend analysis. Peak load is a measure of how strong the bone is at the site of fracture repair. 0.1 nmol, 1 nmol, and 10 nmol of the conjugate were delivered daily by subcutaneous injection. JNK3_Mp4_(D)$E_{10}$ conjugate raises bone strength at the fracture calluses three weeks post fracture.

Figure 53:
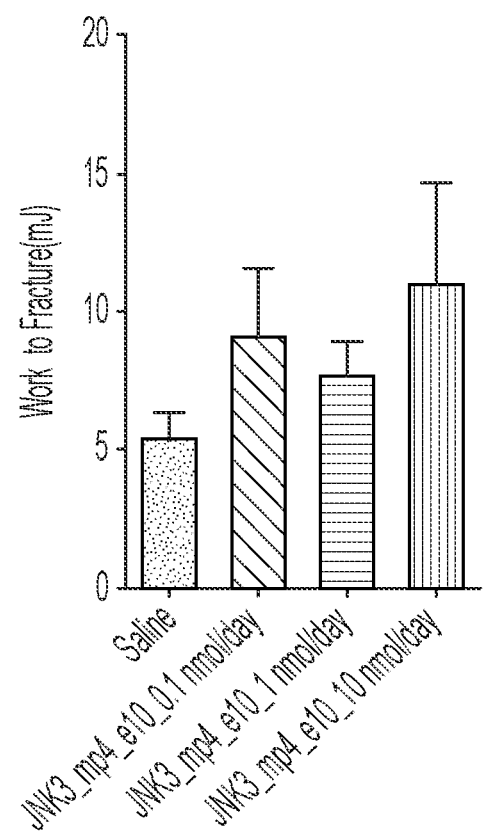
FIG. 53. Work to Fracture (mJ) after treatment with saline, or 0.1 nmol/day, 1 nmol/day or 10 nmol/day of JNK3_mp4_e10.

Referring now to FIG. 53, in vivo fracture healing efficacy of JNK3_mp4_(D)$E_{10}$ conjugate on Swiss Webster fracture-bearing mice (n=5) after 3 weeks is reflected as work to fracture. Work to fracture represents the total amount of energy absorbed by the healed femur before it refractured in a postmortem 4 point bend analysis. Work to fracture is a measure of how strong the bone is at the site of fracture repair. 0.1 nmol, 1 nmol, and 10 nmol of the conjugate were delivered daily by subcutaneous injection. JNK3_mp4_(D)$E_{10}$ conjugate raises bone strength at the fracture calluses three weeks post fracture.

Example 20. Lactoferrin_mp4_e10 Effect on Fracture Healing

Figure 55:
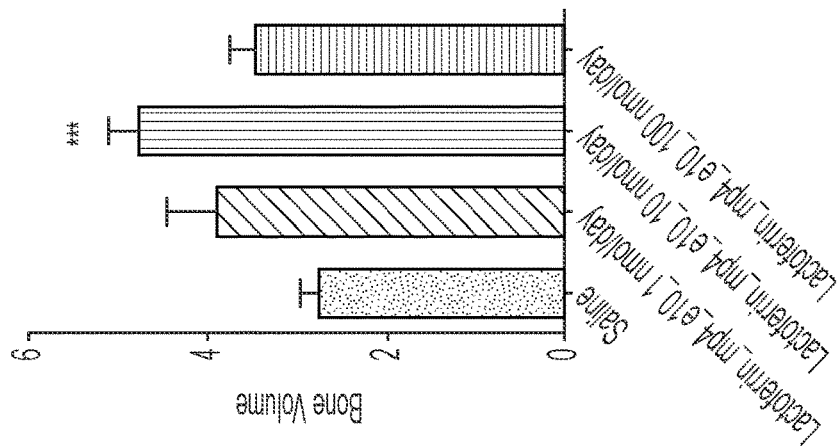
FIG. 55. Bone Volume measured after treatment with saline, or 0.1 nmol/day, 1 nmol/day or 10 nmol/day of Lactoferrin_mp4_e10.

Example 20 indicates Lactoferrin effect on fracture healing. Referring now to FIG. 55, in vivo fracture healing efficacy of Lactoferrin_mp4_(D)$E_{10}$ conjugate on Swiss Webster fracture-bearing mice (n=5) after 3 weeks is reflected as By. BV represents the bone volume of the 100 thickest micro CT slices of the fracture callus and is a measure of how much bone has mineralized at the site of fracture repair. 1 nmol, 10 nmol, and 100 nmol of the conjugate were delivered daily by subcutaneous injection. Lactoferrin_mp4_(D)$E_{10}$ conjugate raises bone mineralization at the fracture calluses three weeks post fracture.

Figure 56:
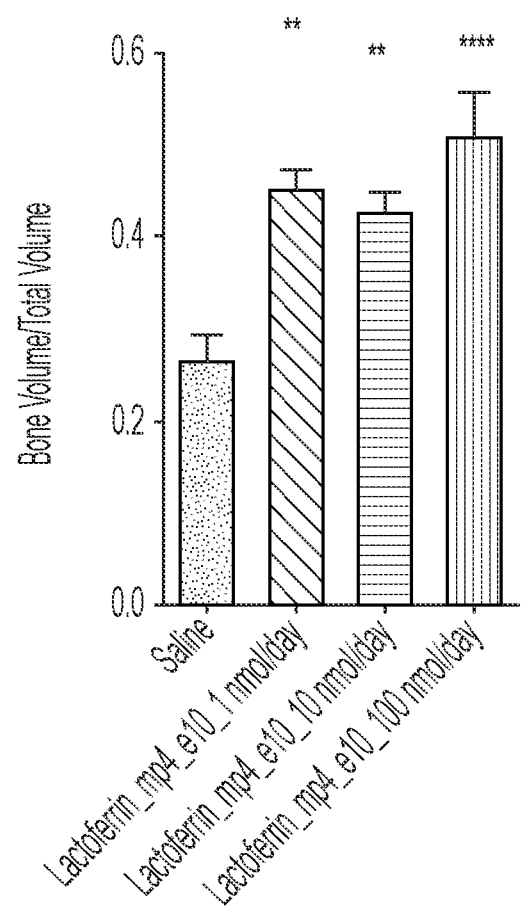
FIG. 56. Bone Volume measured after treatment with saline, or 0.1 nmol/day, 1 nmol/day or 10 nmol/day of Lactoferrin_mp4_e10.

Referring now to FIG. 56, in vivo fracture healing efficacy of Lactoferrin_mp4_(D)$E_{10}$ conjugate on Swiss Webster fracture-bearing mice (n=5) after 3 weeks is reflected as BV/TV. BV/TV represents the bone volume divided by total volume of the 100 thickest micro CT slices of the fracture callus and is a measure of how dense the bone is at the site of fracture repair. 1 nmol, 10 nmol, and 100 nmol of the conjugate were delivered daily by subcutaneous injection. Lactoferrin_mp4_(D)$E_{10}$ conjugate raises bone density at the fracture calluses three weeks post fracture.

Figure 57:
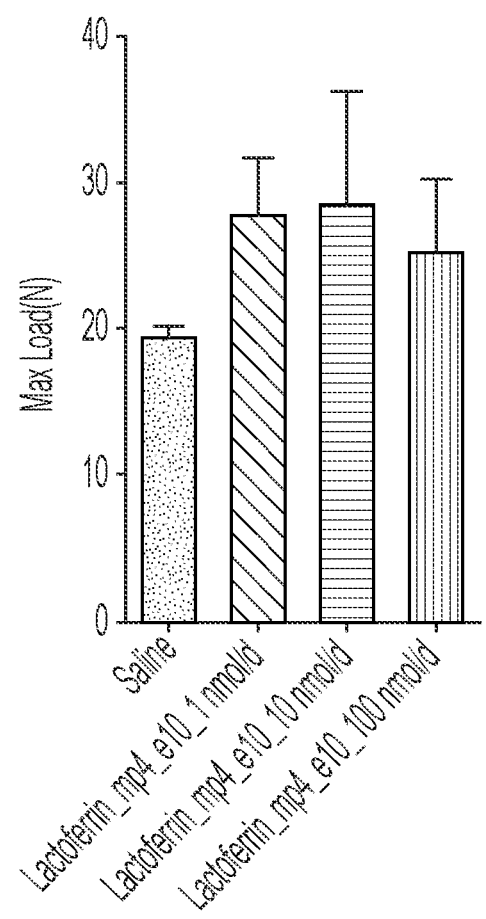
FIG. 57. Max Load (N) measured after treatment with saline, or 0.1 nmol/day, 1 nmol/day or 10 nmol/day of Lactoferrin_mp4_e10.

Referring now to FIG. 57, in vivo fracture healing efficacy of Lactoferrin_mp4_(D)$E_{10}$ conjugate on Swiss Webster fracture-bearing mice (n=5) after 3 weeks is reflected as work to fracture. Work to fracture represents the total amount of energy absorbed by the healed femur before it refractured in a postmortem 4 point bend analysis. Work to fracture is a measure of how strong the bone is at the site of fracture repair. 1 nmol, 10 nmol, and 100 nmol of the conjugate were delivered daily by subcutaneous injection. Lactoferrin_mp4_(D)$E_{10}$ conjugate raises bone strength at the fracture calluses three weeks post fracture.

Figure 58:
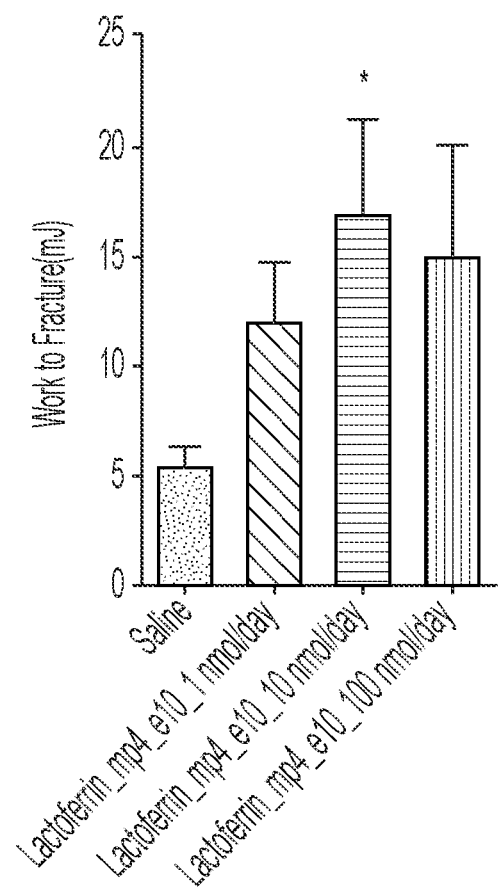
FIG. 58. Work to Fracture (mJ) measured after treatment with saline, or 0.1 nmol/day, 1 nmol/day or 10 nmol/day of Lactoferrin_mp4_e10.

Referring now to FIG. 58, in vivo fracture healing efficacy of Lactoferrin_mp4_(D)$E_{10}$ conjugate on Swiss Webster fracture-bearing mice (n=5) after 3 weeks is reflected as work to fracture. Work to fracture represents the total amount of energy absorbed by the healed femur before it refractured in a postmortem 4 point bend analysis. Work to fracture is a measure of how strong the bone is at the site of fracture repair. 1 nmol, 10 nmol, and 100 nmol of the conjugate were delivered daily by subcutaneous injection. Lactoferrin_mp4_(D)$E_{10}$ conjugate raises bone strength at the fracture calluses three weeks post fracture.

Figure 60:
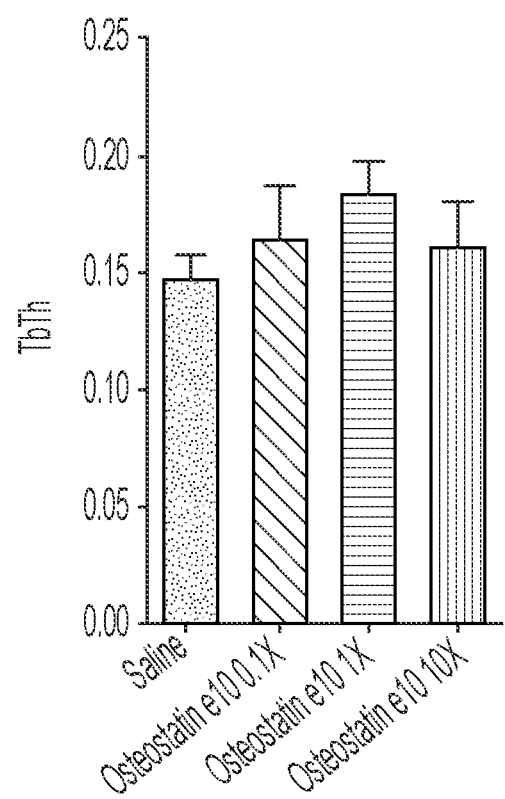
FIG. 60. TbTh measured after treatment with saline, or 0.1 nmol/day, 1 nmol/day or 10 nmol/day of Osteostatin_mp4_(D)E$_{10}$.

Example 21. Osteostatin: Osteostatin (PTHrP[107-139])_e 10 Effect on Fracture Healing Example 21 indicates Osteostatin effect of fracture healing. Referring now to FIG. 60, in vivo fracture healing efficacy of Osteostatin_mp4_(D)$E_{10}$ conjugate on Swiss Webster fracture-bearing mice (n=5) after 3 weeks is reflected as Tbth. Tbth represents the trabecular thickness of the 100 thickest micro CT slices of the fracture callus and is a measure the quality of the bone at the site of fracture repair. 0.1×, 1× and 10× are respectively 0.1 nmol, 1 nmol, and 10 nmol of the conjugate delivered daily by subcutaneous injection. Theof Osteostatin_mp4_(D)$E_{10}$ conjugate raises bone quality at the fracture calluses three weeks post fracture.

Figure 61:
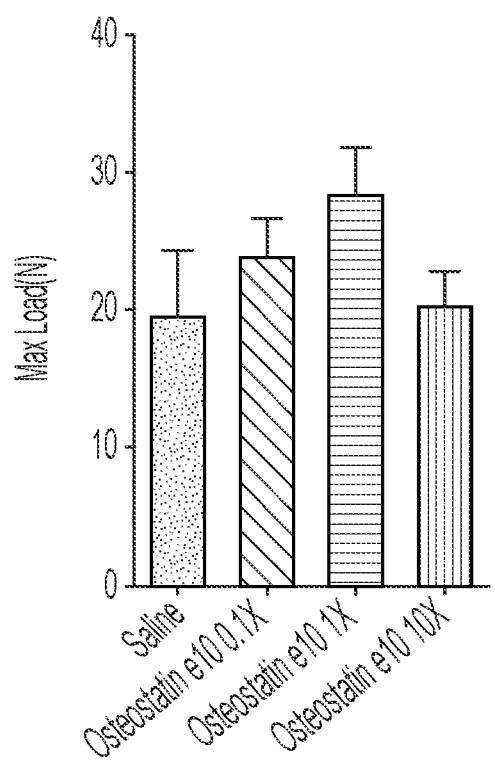
FIG. 61. Max Load_(N) measured after treatment with saline, or 0.1 nmol/day, 1 nmol/day or 10 nmol/day of Osteostatin_mp4_(D)E$_{10}$.

Referring now to FIG. 61, in vivo fracture healing efficacy of Osteostatin_mp4_(D)$E_{10}$ conjugate on Swiss Webster fracture-bearing mice(n=5) after 3 weeks is reflected as max load. Max load represents the maximum force the healed femur withstood before it refractured in a postmortem 4 point bend analysis. Peak load is a measure of how strong the bone is at the site of fracture repair. 0.1×, 1× and 10× are respectively 0.1 nmol, 1 nmol, and 10 nmol of the conjugate delivered daily by subcutaneous injection. Osteostatin_mp4_(D)$E_{10}$ conjugate raises bone strength at the fracture calluses three weeks post fracture.

Figure 62:
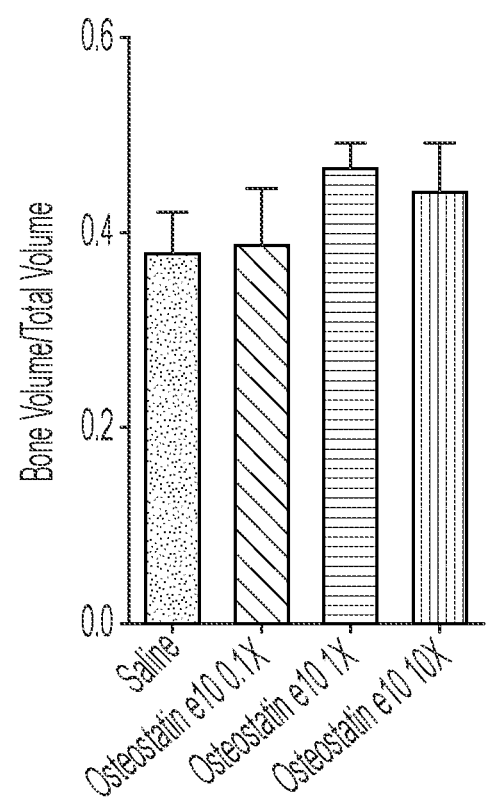
FIG. 62. Bone Volume/Total Volume measured after treatment with saline, or 0.1 nmol/day, 1 nmol/day or 10 nmol/day of Osteostatin_mp4_(D)E$_{10}$.

Referring now to FIG. 62, in vivo fracture healing efficacy of Osteostatin_mp4_(D)$E_{10}$ conjugate on Swiss Webster fracture-bearing mice(n=5) after 3 weeks is reflected as BV/TV. BV/TV-represents the bone volume divided by total volume of the 100 thickest micro CT slices of the fracture callus and is a measure of how dense the bone is at the site of fracture repair. 0.1×, 1× and 10× are respectively 0.1 nmol, 1 nmol, and 10 nmol of the conjugate delivered daily by subcutaneous injection. Osteostatin_mp4_(D)$E_{10}$ conjugate raises bone density at the fracture calluses three weeks post fracture.

Figure 63:
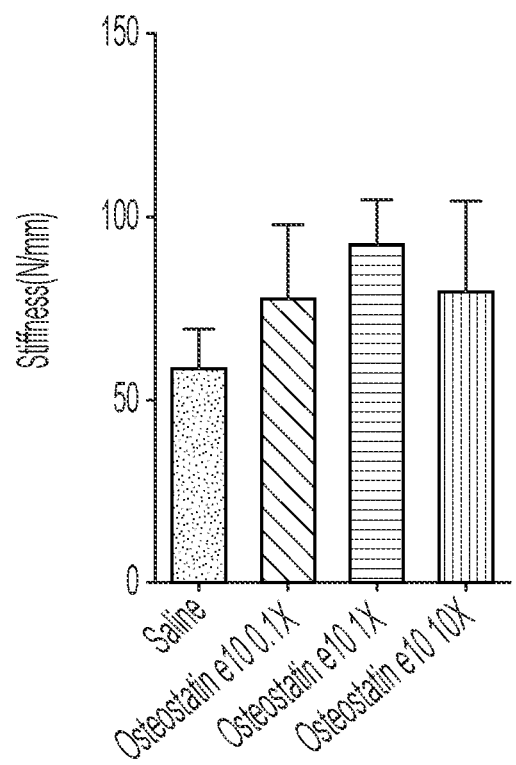
FIG. 63. Stiffness (N/mm) measured after treatment with saline, or 0.1 nmol/day, 1 nmol/day or 10 nmol/day of Osteostatin_mp4_(D)E$_{10}$.

Referring now to FIG. 63, in vivo fracture healing efficacy of Osteostatin_mp4_(D)$E_{10}$ conjugate on Swiss Webster fracture-bearing mice(n=5) after 3 weeks is reflected as stiffness. Stiffness represents the Youngs modulus of the healed femur as it was measured before it refractured in a postmortem 4 point bend analysis. Peak load is a measure of how stiff the bone is at the site of fracture repair. 0.1×, 1× and 10× are respectively 0.1 nmol, 1 nmol, and 10 nmol of the conjugate delivered daily by subcutaneous injection. The of Osteostatin_mp4_(D)$E_{10}$ conjugate raises bone stiffness at the fracture calluses three weeks post fracture.

Figure 64:
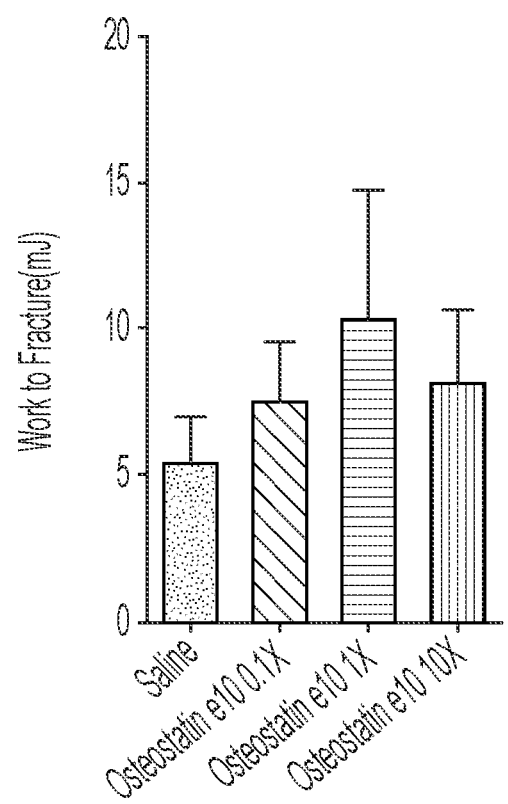
FIG. 64. Work to Fracture (mJ) measured after treatment with saline, or 0.1 nmol/day, 1 nmol/day or 10 nmol/day of Osteostatin_mp4_(D)E$_{10}$.

Referring now to FIG. 64, in vivo fracture healing efficacy of Osteostatin_mp4_(D)$E_{10}$ conjugate on Swiss Webster fracture-bearing mice(n=5) after 3 weeks is reflected as work to fracture. Work to fracture represents the total amount of energy absorbed by the healed femur before it refractured in a postmortem 4 point bend analysis. Work to fracture is a measure of how strong the bone is at the site of fracture repair. 0. 1×, 1× and 10× are respectively 0.1 nmol, 1 nmol, and 10 nmol of the conjugate delivered daily by subcutaneous injection. Osteostatin_mp4_(D)$E_{10}$ conjugate raises bone strength at the fracture calluses three weeks post fracture.

Example 22. P2A-Mp4-e10 Effect on Fracture Healing

Figure 66:
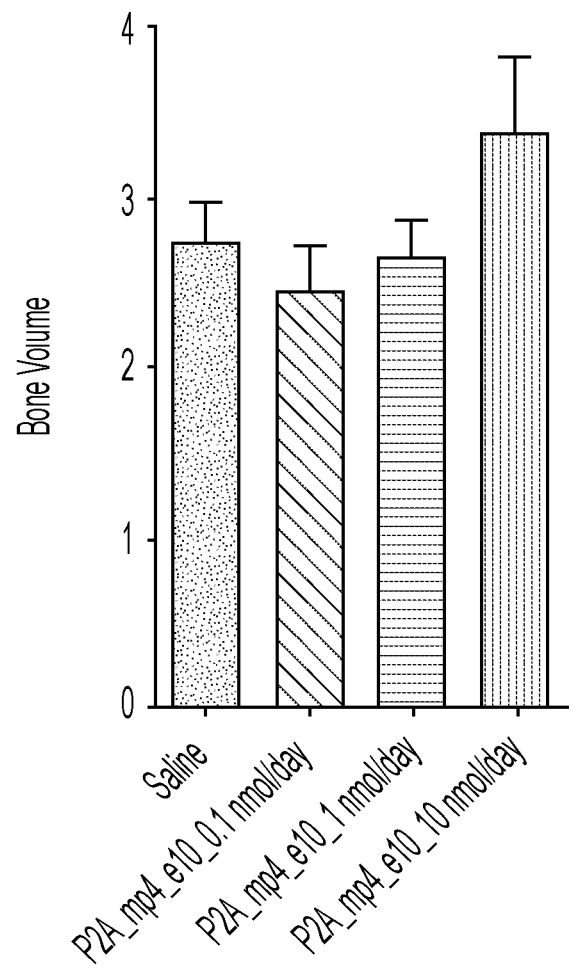
FIG. 66. Bone Volume measured after treatment with saline, or 0.1 nmol/day, 1 nmol/day or 10 nmol/day of P2A-mp4-e10.

Example 22 indicates P2A effect on fracture healing. Referring now to FIG. 66, in vivo fracture healing efficacy of P2A_mp4_(D)$E_{10}$ conjugate on Swiss Webster fracture-bearing mice(n=5) after 3 weeks. BV represents the bone volume of the 100 thickest micro CT slices of the fracture callus and is a measure of how much bone has mineralized at the site of fracture repair. 0.1 nmol, 1 nmol, and 10 nmol of the conjugate were delivered daily by subcutaneous injection. P2A_mp4_(D)$E_{10}$ conjugate raises bone mineralization at the fracture calluses three weeks post fracture.

Figure 67:
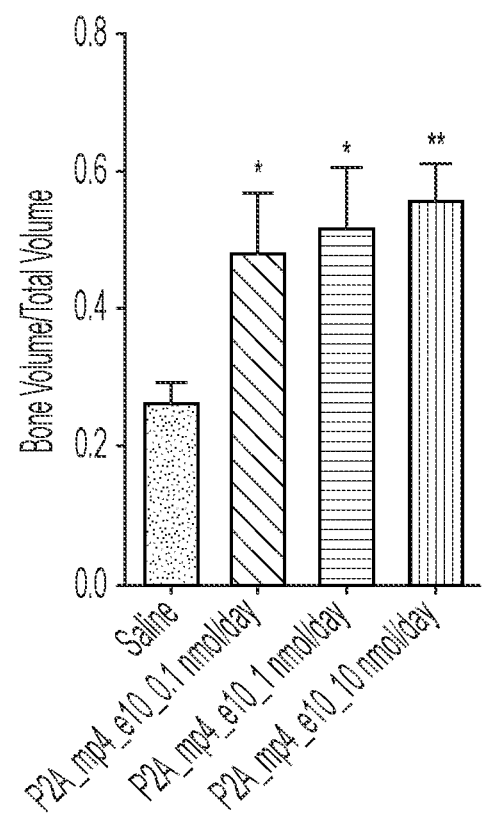
FIG. 67. Bone Volume/Total Volume measured after treatment with saline, or 0.1 nmol/day, 1 nmol/day or 10 nmol/day of P2A-mp4-e10.

Referring now to FIG. 67, in vivo fracture healing efficacy of P2A_mp4_(D)$E_{10}$ conjugate on Swiss Webster fracture-bearing mice(n=5) after 3 weeks. BY/TV-represents the bone volume divided by total volume of the 100 thickest micro CT slices of the fracture callus and is a measure of how dense the bone is at the site of fracture repair. 0.1 nmol, 1 nmol, and 10 nmol of the conjugate were delivered daily by subcutaneous injection. P2A_mp4_(D)$E_{10}$ conjugate raises bone density at the fracture calluses three weeks post fracture.

Figure 68:
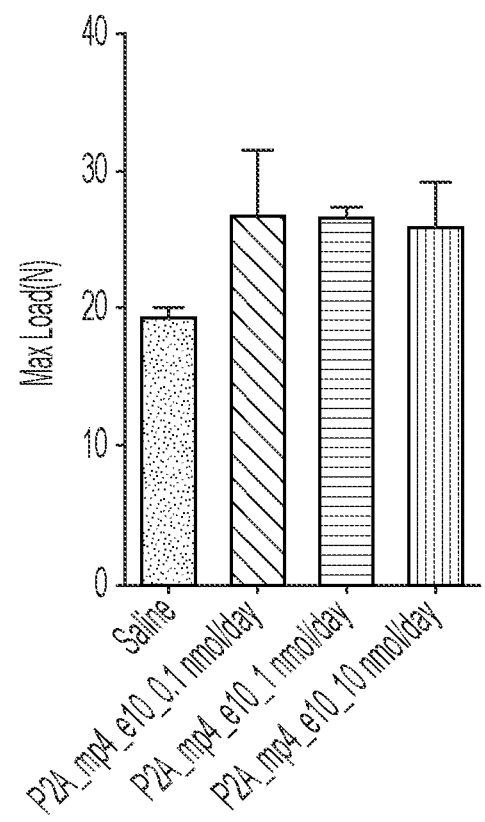
FIG. 68. Max Load (N) measured after treatment with saline, or 0.1 nmol/day, 1 nmol/day or 10 nmol/day of P2A-mp4-e10.

Referring now to FIG. 68, in vivo fracture healing efficacy of P2A_mp4_(D)$E_{10}$ conjugate on Swiss Webster fracture-bearing mice(n=5) after 3 weeks. Max load represents the maximum force the healed femur withstood before it refractured in a postmortem 4 point bend analysis. Peak load is a measure of how strong the bone is at the site of fracture repair. 0.1 nmol, 1 nmol, and 10 nmol of the conjugate were delivered daily by subcutaneous injection. P2A_mp4_(D)$E_{10}$ conjugate raises bone strength at the fracture calluses three weeks post fracture.

Figure 69:
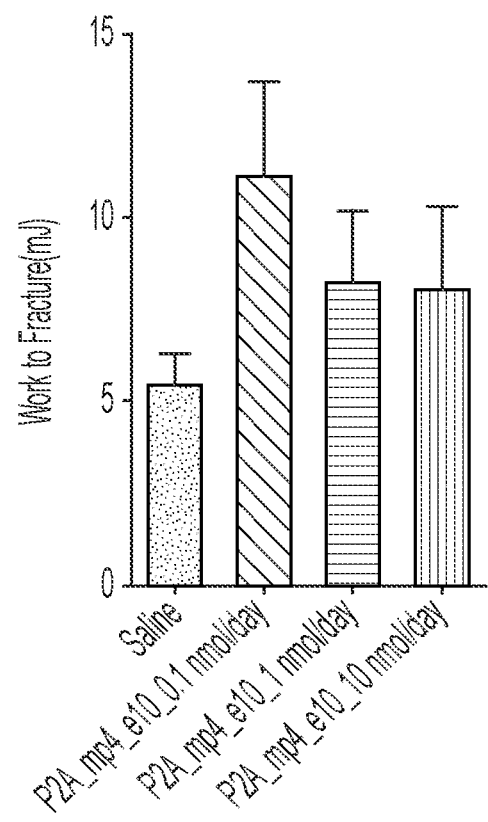
FIG. 69. Work to Fracture (mJ) after treatment with saline, or 0.1 nmol/day, 1 nmol/day or 10 nmol/day of P2A-mp4-e10.

Referring now to FIG. 69, in vivo fracture healing efficacy of P2A_mp4_(D)$E_{10}$ conjugate on Swiss Webster fracture-bearing mice(n=5) after 3 weeks. Work to fracture represents the total amount of energy absorbed by the healed femur before it refractured in a postmortem 4 point bend analysis. Work to fracture is a measure of how strong the bone is at the site of fracture repair. 0.1 nmol, 1 nmol, and 10 nmol of the conjugate were delivered daily by subcutaneous injection. P2A_mp4_(D)$E_{10}$ conjugate raises bone strength at the fracture calluses three weeks post fracture.

Example 23. Preptin (1-34) Mp4_e10 Effect on Fracture Healing

Figure 71:
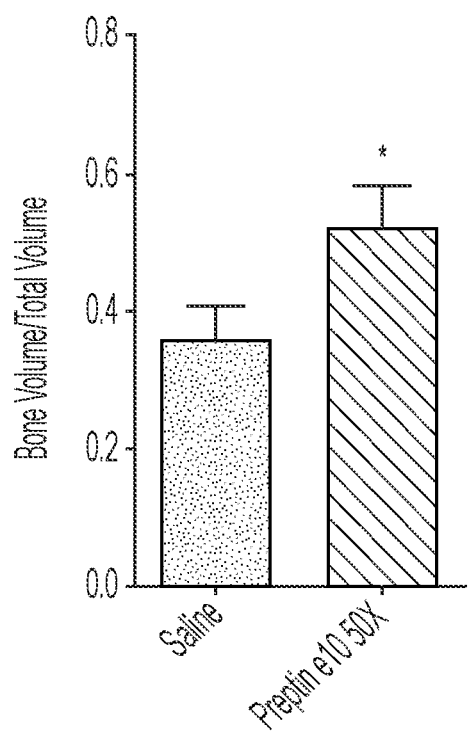
FIG. 71. Bone Volume/Total Volume measured after treatment with saline, or Preptin (1-34)_mp4_e10_50x.

Example 23 indicates Preptin (1-34) effect on fracture healing. Referring now to FIG. 71, in vivo fracture healing efficacy of Preptin(1-34)_mp4_(D)$E_{10}$ conjugate on cluster of differentiation-1 (CD-1) male mice fracture-bearing mice (n=10) after 4 weeks is reflected as BV/TV. BV/TV represents the bone volume of the total volume of 100 thickest micro CT slices of the fracture callus and is a measure of bone density at the site of fracture repair. 50× represents 50 nmol of the conjugate delivered daily by subcutaneous injection. Preptin(1-34)_mp4_(D)$E_{10}$ conjugate significantly raises bone density at the fracture calluses four weeks post fracture.

Figure 72:
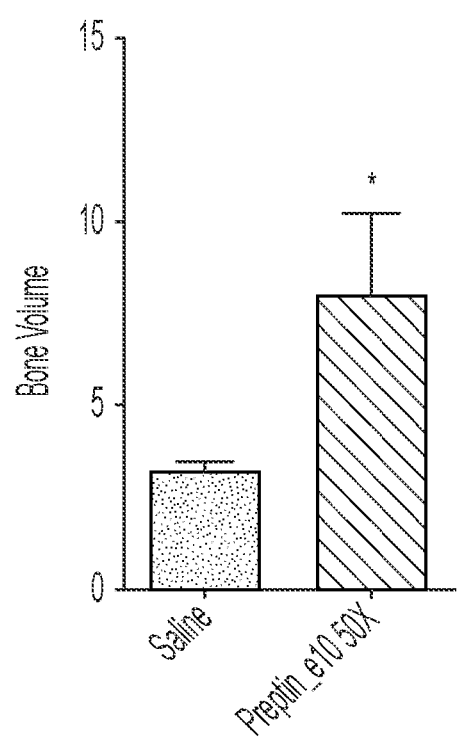
FIG. 72. Bone Volume measured after treatment with saline, or Preptin (1-34)_mp4_e10_50x.

Referring now to FIG. 72, in vivo fracture healing efficacy of Preptin(1-34)_mp4_(D)$E_{10}$ conjugate on CD-1 male mice fracture-bearing mice (n=10) after 4 weeks is reflected as By. BV represents the bone volume of the 100 thickest micro CT slices of the fracture callus and is a measure of how much bone has mineralized at the site of fracture repair 50× represents 50 nmol of the conjugate delivered daily by subcutaneous injection. Preptin(1-34)_mp4_(D)$E_{10}$ conjugate significantly raises bone mineralization at the fracture calluses four weeks post fracture.

Figure 73:
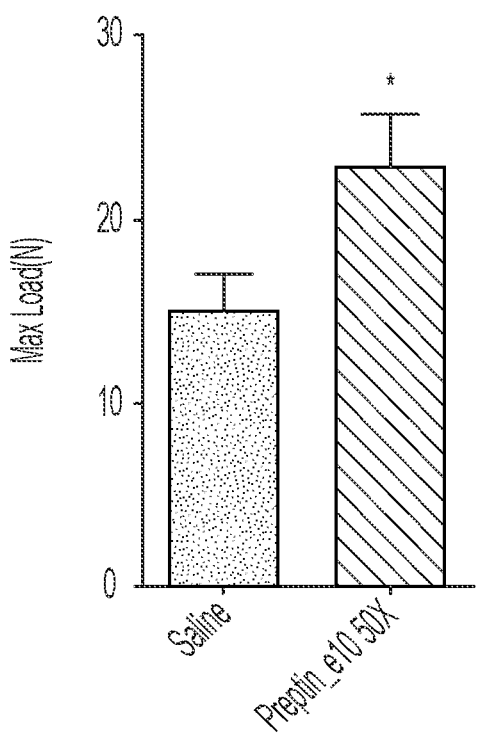
FIG. 73. Max Load (N) measured after treatment with saline, or Preptin (1-34)_mp4_e10_50x.

Referring now to FIG. 73, in vivo fracture healing efficacy of Preptin(1-34)_mp4_(D)$E_{10}$ conjugate on CD-1 Male mice fracture-bearing mice(n=10) after 4 weeks is reflected as max load.

Max load represents the maximum force the healed femur withstood before it refractured in a postmortem 4 point bend analysis. Peak load is a measure of how strong the bone is at the site of fracture repair. 50× represents 50 nmol of the conjugate delivered daily by subcutaneous injection. Preptin (1-34)_mp4_(D)$E_{10}$ conjugate significantly raises bone strength at the fracture calluses four weeks post fracture.

Figure 74:
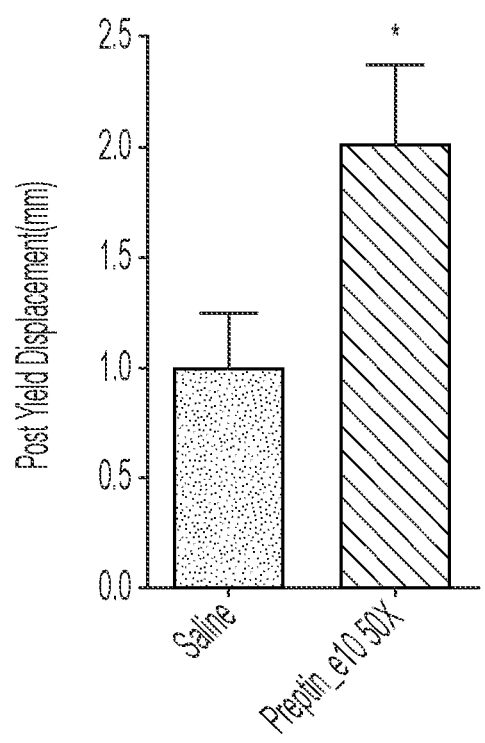
FIG. 74. Post Yield Displacement (mm) measured after treatment with saline, or Preptin (1-34)_mp4_e10_50x.

Referring now to FIG. 74, in vivo fracture healing efficacy of Preptin(1-34)_mp4_(D)$E_{10}$ conjugate on CD-1 Male mice fracture-bearing mice(n=10) after 4 weeks is reflected as post yield displacement. Post yield displacement represents the total displacement of the healed femur after the yield point has been reached in a postmortem 4 point bend analysis Post yield displacement is a measure of how elastic a material is. 50× represents 50 nmol of the conjugate delivered daily by subcutaneous injection. Preptin(1-34)_mp4_(D)$E_{10}$ conjugate significantly reduces the bone brittleness at the fracture calluses four weeks post fracture.

Figure 75:
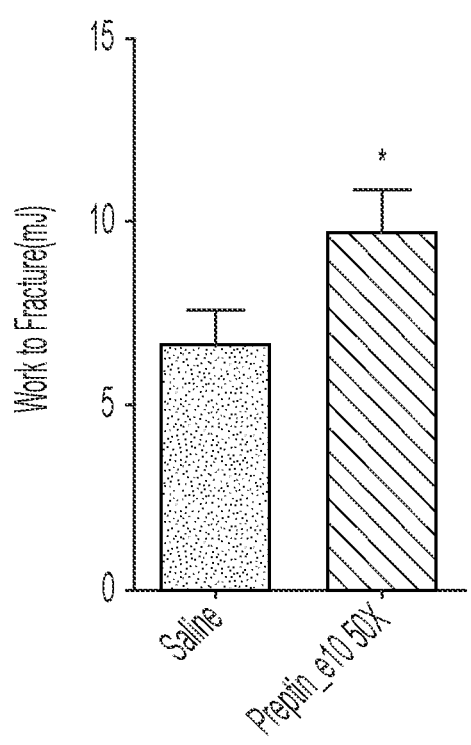
FIG. 75. Work to Fracture (mJ) measured after treatment with saline, or Preptin (1-34)_mp4_e10_50x.

Referring now to FIG. 75, in vivo fracture healing efficacy of Preptin(1-34)_mp4_(D)$E_{10}$ conjugate on CD-1 Male mice fracture-bearing mice(n=10) after 4 weeks is reflected as work to fracture. Work to fracture represents the total amount of energy absorbed by the healed femur before it refractured in a postmortem 4 point bend analysis. Work to fracture is a measure of how strong the bone is at the site of fracture repair. 50× represents 50 nmol of the conjugate delivered daily by subcutaneous injection. Preptin(1-34)

_mp4_(D)E$_{10}$ conjugate significantly raises bone strength at the fracture calluses four weeks post fracture.

Example 24. QK_mp4_e10 Effect on Fracture Healing

Figure 77:
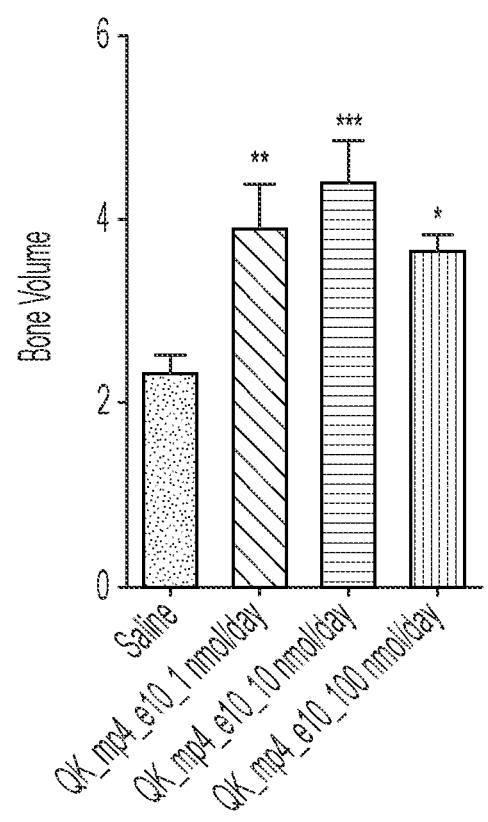
FIG. 77. Bone Volume measured after treatment with saline, or 1.0 nmol/day, or 10 nmol/day or 100 nmol/day of QK_mp4_e10.

Example 24 indicates QK effect on fracture healing. Referring now to FIG. 77, in vivo fracture healing efficacy of QK_mp4_(D)E$_{10}$ conjugate on Swiss Webster fracture-bearing mice(n=5) after 17 days is reflected as By. BV represents the bone volume of the 100 thickest micro CT slices of the fracture callus and is a measure of how much bone has mineralized at the site of fracture repair. 1 nmol, 10 nmol, and 100 nmol of the conjugate were delivered daily by subcutaneous injection. QK_mp4_(D)E$_{10}$ conjugate raises bone mineralization at the fracture calluses 17 days post fracture.

Figure 78:
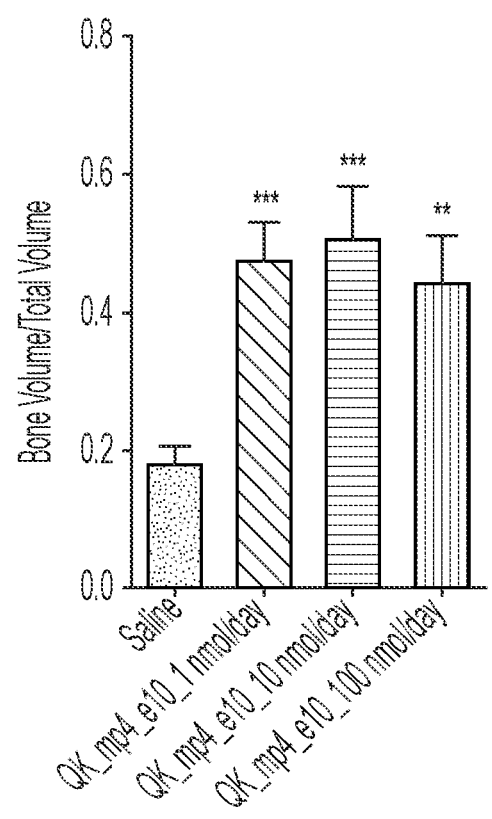
FIG. 78. Bone Volume/Total Volume measured after treatment with saline, or 1.0 nmol/day, or 10 nmol/day or 100 nmol/day of QK_mp4_e10.

Referring now to FIG. 78, in vivo fracture healing efficacy of QK_mp4_(D)E$_{10}$ conjugate on Swiss Webster fracture-bearing mice(n=5) after 17 days is reflected as BV/TV. BY/TV-represents the bone volume divided by total volume of the 100 thickest micro CT slices of the fracture callus and is a measure of how dense the bone is at the site of fracture repair. 1 nmol, 10 nmol, and 100 nmol of the conjugate were delivered daily by subcutaneous injection. QK_mp4_(D)E$_{10}$ conjugate raises bone density at the fracture calluses 17 days post fracture.

Figure 79:
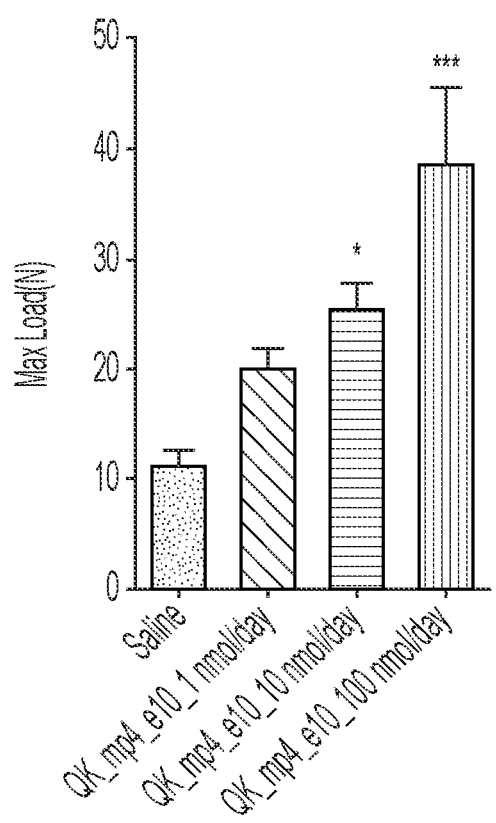
FIG. 79. Max Load (N) measured after treatment with saline, or 1.0 nmol/day, or 10 nmol/day or 100 nmol/day of QK_mp4_e10.

Referring now to FIG. 79, in vivo fracture healing efficacy of QK_mp4_(D)E$_{10}$ conjugate on Swiss Webster fracture-bearing mice(n=5) after 17 days is reflected as max load (N). Max load represents the maximum force the healed femur withstood before it refractured in a postmortem 4 point bend analysis. Peak load is a measure of how strong the bone is at the site of fracture repair. 1 nmol, 10 nmol, and 100 nmol of the conjugate were delivered daily by subcutaneous injection. QK_mp4_(D)E$_{10}$ conjugate raises bone strength at the fracture calluses 17 days post fracture.

Figure 80:
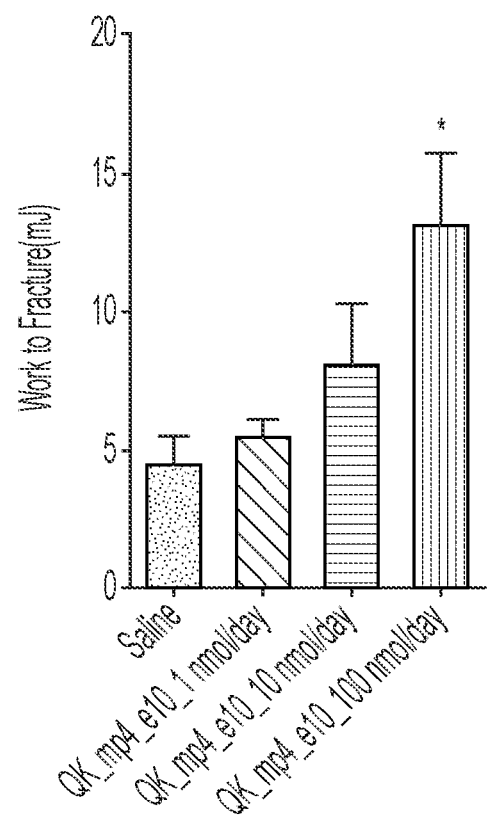
FIG. 80. Work to Fracture (mJ) measured after treatment with saline, or 1.0 nmol/day, or 10 nmol/day or 100 nmol/day of QK_mp4_e10.

Referring now to FIG. 80, in vivo fracture healing efficacy of QK_mp4_(D)E$_{10}$ conjugate on Swiss Webster fracture-bearing mice (n=5) after 17 days is reflected as work to fracture. Work to fracture represents the total amount of energy absorbed by the healed femur before it refractured in a postmortem 4 point bend analysis. Work to fracture is a measure of how strong the bone is at the site of fracture repair. 1 nmol, 10 nmol, and 100 nmol of the conjugate were delivered daily by subcutaneous injection. QK_mp4_(D)E$_{10}$ conjugate raises bone strength at the fracture calluses 17 days post fracture.

Example 25. Effect of Annexin-1 on Fracture Healing

Figure 82:
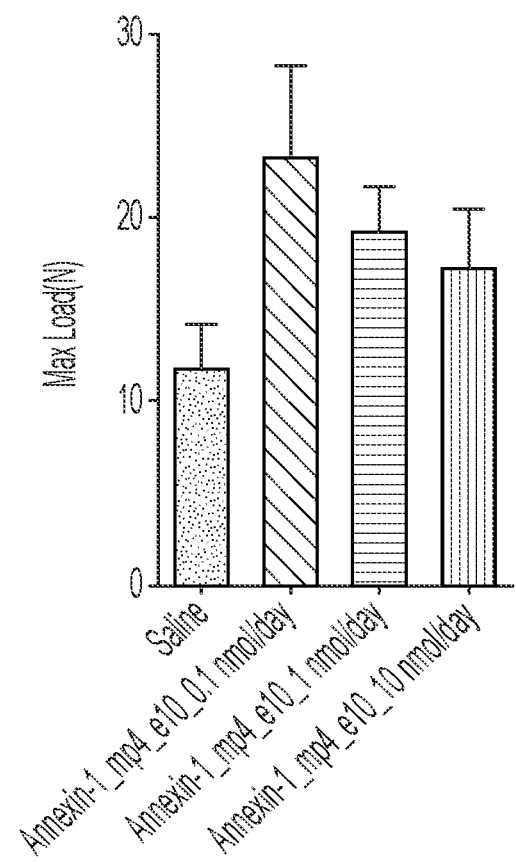
FIG. 82 Max Load (N) measured after treatment with saline, or 1.0 nmol/day, or 10 nmol/day or 100 nmol/day of Annexin 1.

Example 25 indicates Annexin-1 effect on fracture healing. Referring now to FIG. 82, in vivo fracture healing efficacy of Annexin_mp4_(D)E$_{10}$ conjugate on Swiss Webster fracture bearing mice (n=5) after 16 days is reflected as max load (N). Max load represents the maximum force the healed femur withstood before it refractured in a postmortem 4 point bend analysis. Max load is a measure of how strong the bone is at the site of fracture repair. 0.1 nmol, 1 nmol, and 10 nmol of the conjugate were delivered daily by subcutaneous injection. Annexin_mp4_(D)E$_{10}$ conjugate raises bone strength at the fracture calluses three weeks post fracture.

Figure 83:
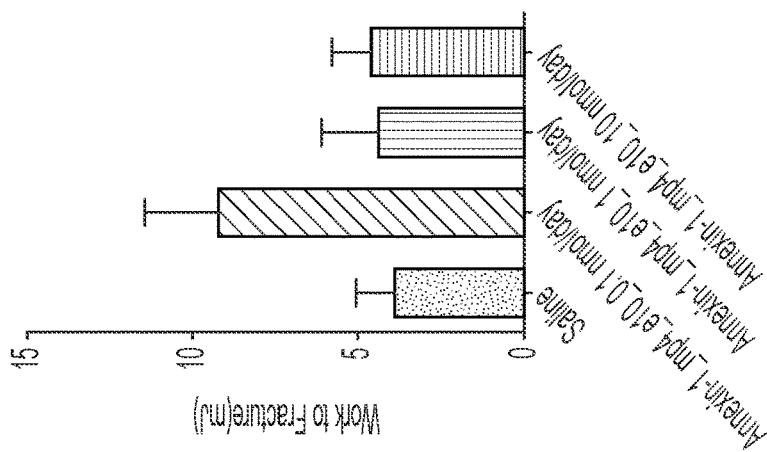
FIG. 83 Work to Fracture (mJ) measured after treatment with saline, or 1.0 nmol/day, or 10 nmol/day or 100 nmol/day of Annexin 1.

Referring now to FIG. 83, in vivo fracture healing efficacy of Annexin_mp4_(D)E$_{10}$ conjugate on Swiss Webster fracture-bearing mice (n=5) after 16 days is reflected as work to fracture (mJ). Work to fracture represents the total amount of energy absorbed by the healed femur before it refractured in a postmortem 4 point bend analysis. Work to fracture is a measure of how strong the bone is at the site of fracture repair. 0.1 nmol, 1 nmol, and 10 nmol of the conjugate were delivered daily by subcutaneous injection. Annexin_mp4_(D)E$_{10}$ conjugate raises bone strength at the fracture calluses three weeks post fracture.

The invention claimed is:

1. A compound having a structure of:

X-Y-Z wherein:
X comprises a fibroblast growth factor (FGF) receptor targeting sequence;
Y is a releasable linker; and
Z is a bone-targeting molecule,
or a pharmaceutically acceptable salt thereof.

2. The compound of claim 1, wherein X comprises a targeting sequence of native FGF-2.

3. The compound of claim 2, wherein X comprises two copies of the targeting sequence of native FGF-2.

4. The compound of claim 2, wherein the targeting sequence of native FGF-2 is YRSRKYSSWYVALKR (SEQ ID NO: 42).

5. The compound of claim 1, wherein Z comprises a polypeptide.

6. The compound of claim 1, wherein Z comprises not less than 4 and not more than 40 amino acid residues.

7. The compound of claim 6, wherein at least one amino acid is aspartic acid or glutamic acid.

8. The compound of claim 1, wherein Z comprises not less than 6 and not more than 20 glutamic acid residues or not less than 6 and not more than 20 aspartic acid residues.

9. The compound of claim 1, wherein Z is 10 D-glutamic acid residues or 10 D-aspartic acid residues.

10. The compound of claim 1, wherein Y comprises 2-8 oxyethylene units.

11. The compound of claim 1, wherein the releasable linker comprises at least one releasable linker group, each releasable linker group being independently selected from the group consisting of a disulfide (S-S), an ester, and a protease-specific amide bond.

12. A compound having a structure of:

X-Y-Z wherein:
X comprises a fibroblast growth factor (FGF) receptor targeting sequence;
Y comprises mp4; and
Z is a bone-targeting molecule,
or a pharmaceutically acceptable salt thereof.

13. The compound of claim 1, wherein Z is e10.

14. The compound of claim 12, wherein Z is e10.

15. The compound of claim 12, wherein the compound is SEQ ID NO: 28.

16. A compound having a structure represented by

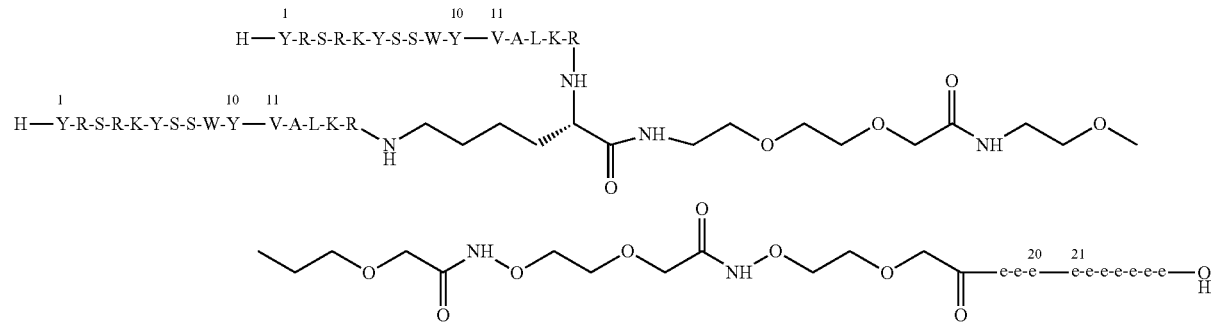

(SEQ ID NOS: 28, 32, and 45).

* * * * *

```
                          SEQUENCE LISTING

Sequence total quantity: 45
SEQ ID NO: 1            moltype = AA  length = 25
FEATURE                 Location/Qualifiers
source                  1..25
                        mol_type = protein
                        organism = synthetic construct
SEQUENCE: 1
DDDDDDDDDD GQGFSYPYKA VFSTQ                                           25

SEQ ID NO: 2            moltype = AA  length = 24
FEATURE                 Location/Qualifiers
source                  1..24
                        mol_type = protein
                        organism = synthetic construct
SEQUENCE: 2
DDDDDDDDDD ALKRQGRTLY GFGG                                            24

SEQ ID NO: 3            moltype = AA  length = 26
FEATURE                 Location/Qualifiers
source                  1..26
                        mol_type = protein
                        organism = synthetic construct
SEQUENCE: 3
DVSTSQAVLP DDFPRYDDDD DDDDDD                                          26

SEQ ID NO: 4            moltype = AA  length = 11
FEATURE                 Location/Qualifiers
source                  1..11
                        mol_type = protein
                        organism = synthetic construct
```

```
SITE                      1
                          note = N-term Arginine modified with (Aspartic acid)10-4
                           mini-PEG moiety
SEQUENCE: 4
RPKPQQFFGL M                                                              11

SEQ ID NO: 5              moltype = AA  length = 38
FEATURE                   Location/Qualifiers
source                    1..38
                          mol_type = protein
                          organism = synthetic construct
SITE                      3
                          note = X is diaminopropinoic acid modified with an
                           octanoylgroup sidechain
SEQUENCE: 5
GSXFLSPEHQ KAQQRKESKK PPAKLQPRDD DDDDDDDD                                 38

SEQ ID NO: 6              moltype = AA  length = 23
FEATURE                   Location/Qualifiers
source                    1..23
                          mol_type = protein
                          organism = synthetic construct
SITE                      23
                          note = C-term modified Lysine with 4 mini PEG-(Glutamic
                           acid)10
SEQUENCE: 6
CGGKVGKACC VPTKLSPISV LYK                                                 23

SEQ ID NO: 7              moltype = AA  length = 32
FEATURE                   Location/Qualifiers
source                    1..32
                          mol_type = protein
                          organism = synthetic construct
DISULFID                  16..32
                          note = Thioester crosslink between residues
SEQUENCE: 7
DDDDDDDDDD GLSKGCFGLK LDRIGSMSGL GC                                       32

SEQ ID NO: 8              moltype = AA  length = 38
FEATURE                   Location/Qualifiers
source                    1..38
                          mol_type = protein
                          organism = synthetic construct
SEQUENCE: 8
HSDAVFTDNY TRLRKQMAVK KYLNSILNDD DDDDDDDD                                 38

SEQ ID NO: 9              moltype = AA  length = 38
FEATURE                   Location/Qualifiers
source                    1..38
                          mol_type = protein
                          organism = synthetic construct
SEQUENCE: 9
DDDDDDDDDD GLRSKSKKFR RPDIQYPDAT DEDITSHM                                 38

SEQ ID NO: 10             moltype = AA  length = 31
FEATURE                   Location/Qualifiers
source                    1..31
                          mol_type = protein
                          organism = synthetic construct
SEQUENCE: 10
HKIPKASSVP TELSAISTLY LDDDDDDDDD D                                        31

SEQ ID NO: 11             moltype = AA  length = 34
FEATURE                   Location/Qualifiers
source                    1..34
                          mol_type = protein
                          organism = synthetic construct
SEQUENCE: 11
DDDDDDDDDD YQPPSTNKNT KSQRRKGSTF EEHK                                     34

SEQ ID NO: 12             moltype = AA  length = 33
FEATURE                   Location/Qualifiers
source                    1..33
                          mol_type = protein
                          organism = synthetic construct
SEQUENCE: 12
DDDDDDDDDD AGYKPDEGKR GDACEGDSGG PFV                                      33

SEQ ID NO: 13             moltype = AA  length = 25
```

-continued

```
FEATURE                 Location/Qualifiers
source                  1..25
                        mol_type = protein
                        organism = synthetic construct
SITE                    10..11
                        note = 4 mini-PEG moiety
SEQUENCE: 13
DDDDDDDDDD DVDVPDGRGD SLAYG                                              25

SEQ ID NO: 14           moltype = AA  length = 23
FEATURE                 Location/Qualifiers
source                  1..23
                        mol_type = protein
                        organism = synthetic construct
SITE                    1
                        note = Acetylated Cysteine
SITE                    14
                        note = C-term Lysine modified with 4 mini-PEG (Aspartic
                         acid)10 moiety
SEQUENCE: 14
CGGKVGKACC VPTKLSPISV LVK                                                23

SEQ ID NO: 15           moltype = AA  length = 32
FEATURE                 Location/Qualifiers
source                  1..32
                        mol_type = protein
                        organism = synthetic construct
SEQUENCE: 15
DDDDDDDDDD GLSKGCFGLK LDRIGSMSGL GC                                      32

SEQ ID NO: 16           moltype = AA  length = 32
FEATURE                 Location/Qualifiers
source                  1..32
                        mol_type = protein
                        organism = synthetic construct
DISULFID                16..32
                        note = Thioester crosslink between residues
SEQUENCE: 16
DDDDDDDDDD GLSKGCFGLK LDRIGSMSGL GC                                      32

SEQ ID NO: 17           moltype = AA  length = 38
FEATURE                 Location/Qualifiers
source                  1..38
                        mol_type = protein
                        organism = synthetic construct
SEQUENCE: 17
HSDAVFTDNY TRLRKQMAVK KYLNSILNDD DDDDDDDD                                 38

SEQ ID NO: 18           moltype = AA  length = 10
FEATURE                 Location/Qualifiers
source                  1..10
                        mol_type = protein
                        organism = synthetic construct
SITE                    10
                        note = C-term modified Aspartic acid with 4 mini PEG moiety
SEQUENCE: 18
DDDDDDDDDD                                                               10

SEQ ID NO: 19           moltype = AA  length = 16
FEATURE                 Location/Qualifiers
source                  1..16
                        mol_type = protein
                        organism = synthetic construct
MOD_RES                 4
                        note = norleucine
SITE                    16
                        note = C-term Lysine modified with Lys-aminohexanoic
                         acid-aminohexanoic acid-aminohexanoic acid-d(Glutamic
                         acid)10 moiety and a second branch of SEQ ID NO: 44
SEQUENCE: 19
AISXLYLDEN EKVVLK                                                        16

SEQ ID NO: 20           moltype = AA  length = 17
FEATURE                 Location/Qualifiers
source                  1..17
                        mol_type = protein
                        organism = synthetic construct
```

```
SITE                      17
                          note = C-term Lysine modified with 4 mini PEG
                              linker-d(Glutamic acid)10 moiety
SEQUENCE: 20
KRTGQYKLGS KTGPGQK                                                        17

SEQ ID NO: 21             moltype = AA  length = 25
FEATURE                   Location/Qualifiers
source                    1..25
                          mol_type = protein
                          organism = synthetic construct
SITE                      25
                          note = C-term Lysine modified with 4 mini PEG
                              linker-d(Glutamic acid)10 moiety
SEQUENCE: 21
MGEKPGTRVF KKSSPNCKLT VYLGK                                               25

SEQ ID NO: 22             moltype = AA  length = 15
FEATURE                   Location/Qualifiers
source                    1..15
                          mol_type = protein
                          organism = synthetic construct
SITE                      15
                          note = C-term Lysine modified with 4 mini PEG
                              linker-d(Glutamic acid)10 moiety
SEQUENCE: 22
FKCRRWQWRM KKLGA                                                          15

SEQ ID NO: 23             moltype = AA  length = 33
FEATURE                   Location/Qualifiers
source                    1..33
                          mol_type = protein
                          organism = synthetic construct
SITE                      33
                          note = C-term Lysine modified with 4 mini PEG
                              linker-d(Glutamic acid)10 moiety
SEQUENCE: 23
TRSAWLDSGV TGSGLEGDHL SDTSTTSLEL DSR                                      33

SEQ ID NO: 24             moltype = AA  length = 32
FEATURE                   Location/Qualifiers
source                    1..32
                          mol_type = protein
                          organism = synthetic construct
SITE                      1
                          note = N-term Valine modified with 4 mini PEG
                              linker-d(Glutamic acid)10 moiety
SEQUENCE: 24
VRGASQRWTD YQFFGVPYRP FDPLVAQSTS VD                                       32

SEQ ID NO: 25             moltype = AA  length = 15
FEATURE                   Location/Qualifiers
source                    1..15
                          mol_type = protein
                          organism = synthetic construct
SITE                      1
                          note = N-term Lysine modified with 4 mini PEG
                              linker-d(Glutamic acid)10 moiety
SEQUENCE: 25
KLTWQELYQL KYKGI                                                          15

SEQ ID NO: 26             moltype = AA  length = 25
FEATURE                   Location/Qualifiers
source                    1..25
                          mol_type = protein
                          organism = synthetic construct
SITE                      1
                          note = Acetylated Alanine
SITE                      25
                          note = C-term Tyrosine modified with 4 mini PEG
                              linker-d(Glutamic acid)10 moiety
SEQUENCE: 26
AMVSEFLKQA WFIENEEQEY VQTVY                                               25

SEQ ID NO: 27             moltype =   length =
SEQUENCE: 27
000

SEQ ID NO: 28             moltype = AA  length = 16
```

```
FEATURE              Location/Qualifiers
source               1..16
                     mol_type = protein
                     organism = synthetic construct
SITE                 16
                     note = C-term Lysine modified with 4 mini PEG
                      linker-d(Glutamic acid)10 moiety
SEQUENCE: 28
YRSRKYSSWY VALKRK                                                   16

SEQ ID NO: 29        moltype = AA  length = 12
FEATURE              Location/Qualifiers
source               1..12
                     mol_type = protein
                     organism = synthetic construct
SITE                 1
                     note = Cysteine with thioester crosslink
SITE                 12
                     note = C-term Lysine modified with 4 mini PEG
                      linker-d(Glutamic acid)10 moeity
SEQUENCE: 29
CVRKIEIVRK KK                                                       12

SEQ ID NO: 30        moltype = AA  length = 10
FEATURE              Location/Qualifiers
source               1..10
                     mol_type = protein
                     organism = synthetic construct
SEQUENCE: 30
DDDDDDDDDD                                                          10

SEQ ID NO: 31        moltype = AA  length = 10
FEATURE              Location/Qualifiers
source               1..10
                     mol_type = protein
                     organism = synthetic construct
SEQUENCE: 31
EEEEEEEEEE                                                          10

SEQ ID NO: 32        moltype = AA  length = 15
FEATURE              Location/Qualifiers
source               1..15
                     mol_type = protein
                     organism = synthetic construct
SITE                 15
                     note = C-term Arginine modified to Lysine side chain
SEQUENCE: 32
YRSRKYSSWY VALKR                                                    15

SEQ ID NO: 33        moltype = AA  length = 10
FEATURE              Location/Qualifiers
source               1..10
                     mol_type = protein
                     organism = synthetic construct
SEQUENCE: 33
VRKIEIVRKK                                                          10

SEQ ID NO: 34        moltype = AA  length = 17
FEATURE              Location/Qualifiers
source               1..17
                     mol_type = protein
                     organism = synthetic construct
SEQUENCE: 34
KRTGQYKLGS KTGPGQK                                                  17

SEQ ID NO: 35        moltype = AA  length = 10
FEATURE              Location/Qualifiers
source               1..10
                     mol_type = protein
                     organism = synthetic construct
SITE                 1..10
                     note = D-Glutamic acid
SITE                 1
                     note = N-term D-Glutamic acid modified with 4 mini PEG
                      moiety
SEQUENCE: 35
EEEEEEEEEE                                                          10

SEQ ID NO: 36        moltype = AA  length = 11
```

```
FEATURE                 Location/Qualifiers
source                  1..11
                        mol_type = protein
                        organism = synthetic construct
SITE                    1
                        note = Cysteine with thioester crosslink
SITE                    11
                        note = C-term Lysine linked via side chain to Lysine
                         modified with 4 mini PEG linker-d(Glutamic acid)10 moiety
SEQUENCE: 36
CVRKIEIVRK K                                                                11

SEQ ID NO: 37           moltype = AA  length = 10
FEATURE                 Location/Qualifiers
source                  1..10
                        mol_type = protein
                        organism = synthetic construct
SITE                    1..10
                        note = D-Glutamic acid
SITE                    10
                        note = C-term D-Glutamic acid modified with 4 mini PEG
                         moiety
SEQUENCE: 37
EEEEEEEEEE                                                                  10

SEQ ID NO: 38           moltype = AA  length = 5
FEATURE                 Location/Qualifiers
source                  1..5
                        mol_type = protein
                        note = targeting polypeptide
                        organism = synthetic construct
SEQUENCE: 38
DDDDD                                                                       5

SEQ ID NO: 39           moltype = AA  length = 5
FEATURE                 Location/Qualifiers
source                  1..5
                        mol_type = protein
                        note = targeting polypeptide
                        organism = synthetic construct
SEQUENCE: 39
EEEEE                                                                       5

SEQ ID NO: 40           moltype = AA  length = 20
FEATURE                 Location/Qualifiers
source                  1..20
                        mol_type = protein
                        note = targeting polypeptide
                        organism = synthetic construct
SEQUENCE: 40
DDDDDDDDDD DDDDDDDDDD                                                       20

SEQ ID NO: 41           moltype = AA  length = 20
FEATURE                 Location/Qualifiers
source                  1..20
                        mol_type = protein
                        note = targeting polypeptide
                        organism = synthetic construct
SEQUENCE: 41
EEEEEEEEEE EEEEEEEEEE                                                       20

SEQ ID NO: 42           moltype = AA  length = 15
FEATURE                 Location/Qualifiers
source                  1..15
                        mol_type = protein
                        note = targeting sequence for F2A's receptor
                        organism = synthetic construct
SEQUENCE: 42
YRSRKYSSWY VALKR                                                            15

SEQ ID NO: 43           moltype = AA  length = 21
FEATURE                 Location/Qualifiers
source                  1..21
                        mol_type = protein
                        organism = synthetic construct
SITE                    10
                        note = modified with 4 mini PEG moiety
SEQUENCE: 43
DDDDDDDDDD RPKPQQFFGL M                                                     21
```

```
SEQ ID NO: 44          moltype = AA  length = 16
FEATURE                Location/Qualifiers
source                 1..16
                       mol_type = protein
                       note = single branch of B2A
                       organism = synthetic construct
SEQUENCE: 44
AISXLYLDEN EKVVLK                                                           16

SEQ ID NO: 45          moltype = AA  length = 10
FEATURE                Location/Qualifiers
source                 1..10
                       mol_type = protein
                       organism = synthetic construct
MOD_RES                1..10
                       note = D-glutamic acid
SEQUENCE: 45
EEEEEEEEEE                                                                  10
```